United States Patent
Luo et al.

(10) Patent No.: US 10,947,350 B2
(45) Date of Patent: Mar. 16, 2021

(54) FUNCTIONAL, SEGREGATED, CHARGED TELODENDRIMERS AND NANOCARRIERS AND METHODS OF MAKING AND USING SAME

(71) Applicant: The Research Foundation for the State University of New York, Syracuse, NY (US)

(72) Inventors: Juntao Luo, Jamesville, NY (US); Xu Wang, Syracuse, NY (US); Changying Shi, Jamesville, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 28 days.

(21) Appl. No.: 15/759,665

(22) PCT Filed: Sep. 12, 2016

(86) PCT No.: PCT/US2016/051266
§ 371 (c)(1),
(2) Date: Mar. 13, 2018

(87) PCT Pub. No.: WO2017/044933
PCT Pub. Date: Mar. 16, 2017

(65) Prior Publication Data
US 2019/0292328 A1 Sep. 26, 2019

Related U.S. Application Data

(60) Provisional application No. 62/217,951, filed on Sep. 13, 2015.

(51) Int. Cl.
*A61K 47/50* (2017.01)
*A61K 9/51* (2006.01)
*A61K 9/107* (2006.01)
*C08G 83/00* (2006.01)
*A61K 47/60* (2017.01)
*A61P 37/08* (2006.01)
*C08G 65/329* (2006.01)

(52) U.S. Cl.
CPC ............ *C08G 83/002* (2013.01); *A61K 9/107* (2013.01); *A61K 9/5146* (2013.01); *A61K 47/60* (2017.08); *A61P 37/08* (2018.01); *C08G 65/329* (2013.01); *C08G 83/00* (2013.01); *C08G 2650/32* (2013.01)

(58) Field of Classification Search
None
See application file for complete search history.

(56) References Cited

U.S. PATENT DOCUMENTS

| | | | | |
|---|---|---|---|---|
| 10,406,233 B2 * | 9/2019 | Luo | ........................ | A61K 47/60 |
| 10,463,694 B2 * | 11/2019 | Luo | ........................ | A61K 47/34 |
| 2010/0278750 A1 * | 11/2010 | Krippner | ............... | A61K 49/124 |
| | | | | 424/9.34 |
| 2012/0276158 A1 | 11/2012 | Fraser et al. | | |
| 2013/0164369 A1 | 6/2013 | Lam et al. | | |
| 2014/0004196 A1 * | 1/2014 | Yang | ........................ | B82Y 5/00 |
| | | | | 424/489 |
| 2014/0363371 A1 | 12/2014 | Luo et al. | | |
| 2015/0056139 A1 * | 2/2015 | Luo | ...................... | A61K 9/5146 |
| | | | | 424/9.1 |

FOREIGN PATENT DOCUMENTS

| | | | | |
|---|---|---|---|---|
| EP | 2322227 A1 | 5/2011 | | |
| WO | 2013096388 A1 | 6/2013 | | |
| WO | WO-2013096388 A1 * | 6/2013 | ....... | C08G 65/33303 |
| WO | 2016/057657 A1 | 4/2016 | | |

OTHER PUBLICATIONS

Huang et al., Mol. Pharmaceutics, 2015, vol. 12, pp. 1216-1229. (Year: 2015).*
Sliwkowski et al., Science, 2013, vol. 341, pp. 1192-1198. (Year: 2013).*
Yuanpei Li et al., Well-Defined, Reversible Boronate Crosslinked Nanocarriers for Targeted Drug Delivery in Response to Acidic pH Values and cis-Diols, Angewandte Chemie International Edition, vol. 51, No. 12, pp. 2864-2869 Jan. 17, 2012.
Kou Okuro et al., Molecular Glues Carrying Multiple Guanidinium Ion Pendants via an Oligoether Spacer: Stabilization of Microtubes against Depolymerization, Journal of the American Chemical Society, vol. 131, No. 5, pp. 1626-1627 Feb. 11, 2009.

* cited by examiner

*Primary Examiner* — Brian Gulledge
(74) *Attorney, Agent, or Firm* — Michael Krenicky; Garrett Smith; Steven A. Wood, Jr.

(57) ABSTRACT

Provided are multiply functional charged telodendrimers. The telodendrimers can be used for protein encapsulation and delivery. The charged telodendrimers may have one or more crosslinking groups (e.g., boronic acid/catechol reversible crosslinking groups). The telodendrimers can aggregate to form nanoparticles. Cargo such as combinations of proteins and other materials may be sequestered in the core of the nanoparticles via non-covalent or covalent interactions with the telodendrimers. Such nanoparticles may be used in protein delivery applications.

14 Claims, 32 Drawing Sheets
Specification includes a Sequence Listing.

SEQUENCE LISTING

```
<160> NUMBER OF SEQ ID NOS: 2

<210> SEQ ID NO 1
<211> LENGTH: 389
<212> TYPE: PRT
<213> ORGANISM: artificial sequence
<220> FEATURE:
<223> OTHER INFORMATION: truncated protein

<400> SEQUENCE: 1

Gly Ala Asp Asp Val Val Asp Ser Ser Lys Ser Phe Val Met Glu Asn
1               5                   10                  15
```

```
Phe Ser Ser Tyr His Gly Thr Lys Pro Gly Tyr Val Asp Ser Ile Gln
             20                  25                  30

Lys Gly Ile Gln Lys Pro Lys Ser Gly Thr Gln Gly Asn Tyr Asp Asp
         35                  40                  45

Asp Trp Lys Gly Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Asn Val Leu Ala Leu Lys Val
                 85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
             115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
             180                 185                 190

Arg Ser Val Gly Ser Ser Leu Ser Cys Ile Asn Leu Asp Trp Asp Val
         195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
             260                 265                 270

Phe Ala Gly Ala Asn Tyr Ala Ala Trp Ala Val Asn Val Ala Gln Val
         275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
             340                 345                 350

Ile Gly Phe Ala Ala Tyr Asn Phe Val Glu Ser Ile Ile Asn Leu Phe
         355                 360                 365

Gln Val Val His Asn Ser Tyr Asn Arg Pro Ala Tyr Ser Pro Gly His
370                 375                 380

Lys Thr Gln Pro Phe
385

<210> SEQ ID NO 2
<211> LENGTH: 449
<212> TYPE: PRT
<213> ORGANISM: artificial sequence
<220> FEATURE:
```

<223> OTHER INFORMATION: recombinant protein

<400> SEQUENCE: 2

```
Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Asn Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
370                 375                 380

Lys Thr Gln Pro Phe Glu Ala Ser Gly Gly Pro Glu Asn Ser Asp Ser
385                 390                 395                 400
```

```
Glu Cys Pro Leu Ser His Asp Gly Tyr Cys Leu His Asp Gly Val Cys
            405                 410                 415
Met Tyr Ile Glu Ala Leu Asp Lys Tyr Ala Cys Asn Cys Val Val Gly
            420                 425                 430
Tyr Ile Gly Glu Arg Cys Gln Tyr Arg Asp Leu Lys Trp Trp Glu Leu
            435                 440                 445
Arg
```

FUNCTIONAL, SEGREGATED, CHARGED TELODENDRIMERS AND NANOCARRIERS AND METHODS OF MAKING AND USING SAME

CROSS REFERENCE TO RELATED APPLICATIONS

This application claims priority to U.S. Provisional Application No. 62/217,951, filed on Sep. 13, 2015, the disclosure of which is hereby incorporated by reference.

STATEMENT REGARDING FEDERALLY SPONSORED RESEARCH

This invention was made with government support under contract no. CA 140449 awarded by the National Institutes of Health. The government has certain rights in the invention.

FIELD OF THE DISCLOSURE

The disclosure generally relates to telodendrimers. More particularly the disclosure generally relates to functional, segregated, charged telodendrimers.

BACKGROUND OF THE DISCLOSURE

Protein therapy is, in a manner, limited by the lack of efficient nanocarriers for intracellular delivery while maintaining protein bioactivity. A rational strategy to create small nanoparticles with high protein loading ability and cell-penetration property is desired but is often overlooked.

Currently, more than 130 bioactive proteins have been approved to treat human diseases. The majority of these protein therapeutics target the receptors or antigens expressed on the plasma membrane, such as insulin and antibodies. The modification of the pharmacokinetic of the proteins by delivery system is able to enhance their therapeutic efficacy. PEGylation of protein has a long-standing history to efficiently prolong circulation time, increase stability and reduce the immunogenicity of protein therapeutics, especially for recombinant protein therapeutics. Physical encapsulation of proteins into nano- or microparticles has been intensively studied for systemic or local administration. It is important to maintain protein structure and activity in such protein encapsulation process, especially for the process involving lyophilization or organic solvent applications. For example, the usage of organic solvents in the oil/water emulsion technique for the encapsulation of proteins into biodegradable polymeric microparticles, e.g., polylactic acid and polycaprolactone, usually causes the denaturation of proteins with at least partial losses of activity. Encapsulation of proteins in aqueous environments, such as in hydrogels and nanogels, represents a better way to sustain protein structure and activities. However, these processes mostly relay on polymerization or chemical reactions to crosslink hydrogels at bulky scale or within the nanodispersed aggregates. The chemical process may lead to the complication in control of the physical properties, and the chemicals used in these reactions may present as toxic impurity that hinders application in vivo. Efficient encapsulation of proteins in situ in biologically relevant environments, e.g., pH, temperature and ion strength without extra chemicals or steps needed are highly demanded for clinical development of protein therapeutics.

Even more proteins are possible to be therapeutics if they can be delivered across plasma membrane into intracellular space, such as antibodies against intracellular proteins used in biochemistry assays or pathology detections. However, such exogenous proteins, even some endogenous proteins are not cell permeable by themselves due to their surface charge distributions, large molecular weights and vulnerable tertiary structures. In addition, they do not have receptors to mediate their intracellular uptake, which renders these proteins inactive. Therefore, the ability to create efficient vehicles for intracellular protein delivery in vivo will expand the horizon dramatically in development and application of therapeutic proteins in disease treatments. The recombinant proteins with targeting domains present solutions for intracellular delivery of such functional proteins. However, the tedious recombinant design/production and the costly process for protein humanization hinder the development of such recombinant therapeutics. Cell-penetrating peptides and cationic polymers/liposomes have been widely studied over the past few decades for intracellular delivery of biomacromolecules, such as genes and proteins while maintaining the bioactivity. However, the advancement of these vehicles are mainly hindered by their positive surface charges, that usually cause high cytotoxicity and are also subjected to nonspecific phagocytosis by the reticuloendothelium systems in vivo. Polymeric vehicles hold great promise to overcome these shortages. The application of microparticles and hydrogels for intracellular protein delivery is limited by their large sizes. The delivery systems based on nano-scaled vehicles are highly promising for intracellular delivery of protein therapeutics to treat human diseases, especially for cancers.

A recent study by Farokhzad and coworkers showed great promise to minimize zeta potential of the cationic nanocarriers by post-modification of the protein-conjugated nanoparticles with lipid-polyethylene glycol, yielding multinuclear nanoparticles with diameters of 100-150 nm. The protein aggregation and dehydration may likely occur within the big aggregates, which may be irreversible and potentially leads to protein denaturation. In addition, many studies suggested that small particle sizes (10-30 nm) are beneficial for therapeutic delivery with large volume intratumoral distribution and deep tumor penetration. Coating protein with a layer of polymer in aqueous solution is able to address all these concerns to avoid protein aggregation, dehydration and form small particle sizes similar to polymeric micelles (10-30 nm). Optimization of the information encoded in macromolecular building blocks is able to tune the sizes of self-assembled nanoparticles. In a previous study, we observed that the precise control on macromolecular architecture and composition was critical to optimize the particle sizes and drug loading behaviors, which seriously affected the colon cancer treatment efficiency.

SUMMARY OF THE DISCLOSURE

In an aspect, the present disclosure provides charged telodendrimers. The charged telodendrimers are linear-dendritic copolymers. The charged telodendrimers are functional segregated telodendrimers having, for example, two or three functional segments. In an embodiment, the functional segments are a hydrophilic segment and a hydrophobic segment. The hydrophilic segment comprises one or more charged groups. The charged telodendrimers may comprise an intermediate layer. The charged telodendrimers may have one or more crosslinking groups (e.g., boronic acid/catechol reversible crosslinking groups). The charged telodendrimers may comprise PEG groups that can form a PEG layer. In an embodiment, the present disclosure provides charged telodendrimers that are functional and spatially segregated telodendrimers having 1 to 128 charged groups. The telodendrimers may have one or more cross-linking groups (e.g., reversible boronate crosslinking groups/reversible catechol crosslinking groups). In an embodiment, the telodendrimers are functional segregated telodendrimers having three functional segments. In various examples, a charged telodendrimer has one or more feature of the charged telodendrimers of Statements 1 to 15 or a combination thereof. The telodendrimers may be used to stabilize proteins. The type of charge, the number of charged groups, the ratio of charged groups to hydrophobic groups (if present), the spatial orientation of the charged groups, and/or the density of the charged groups can be selected to stabilize a specific protein.

In an aspect, the present disclosure provides nanocarriers comprising charged telodendrimers of the present disclosure. In an embodiment, a composition comprises an aggregate of a plurality of the telodendrimers that form a nanocarrier having a hydrophobic core and a hydrophilic exterior. In various examples, a nanocarrier has one or more feature of the nanocarriers of Statements 16 to 18, or a combination thereof. The nanocarrier may be a telodendrimer micelle. A telodendrimer micelle is a nanoconstruct formed by the self-assembly of the telodendrimer in aqueous solution. The telodendrimer micelle can serve as a nanocarrier to load various types of proteins. In an embodiment, the nanocarrier comprises a plurality of charged telodendrimer compounds. In an embodiment, the nanocarrier comprises one or more charged proteins. The nanocarriers comprising one or more charged proteins may have a diameter of 5 nm to 50 nm, including all integer nm values and ranges therebetween. In an embodiment, the nanocarriers comprising one or more charged proteins may have a diameter of 10 nm to 30 nm. The telodendrimers can be designed such that each of the proteins carried will have a different release profile. Examples of conditions that can affect the release profile of carried proteins include time and biological environment.

The charged telodendrimers can be present in a composition. In an embodiment, the composition comprises one or more charged telodendrimers. The composition may comprise a mixture of positively charged telodendrimers, a mixture of negatively charged telodendrimers, or a mixture of positively and negatively charged telodendrimers. In an embodiment the composition further comprises one or more proteins. In an embodiment the composition further comprises one or more drugs. The composition can have a formulation as disclosed herein. For example, the composition can be a pharmaceutical composition as described herein.

In an aspect, the present disclosure provides methods of using charged telodendrimers of the present disclosure. The telodendrimers can be used, for example, in methods of treatment. The compositions or nanocarriers of the present disclosure can be used to treat any disease requiring the administration of a protein, such as, for example, by sequestering a protein in the interior of the nanocarrier, and delivering said protein to a target. The protein(s) can be delivered systemically or intracellularly. In an embodiment, compositions comprising the telodendrimers are used in a method for treating a disease. In some embodiments, the present disclosure provides a method of treating a disease, including administering to a subject in need of such treatment a therapeutically effective amount of a composition or nanocarrier of the present disclosure, where the nanocarrier includes an encapsulated protein. The pharmaceutical preparations are typically delivered to a mammal, including humans and non-human mammals. Non-human mammals treated using the present methods include domesticated animals (e.g., canine, feline, murine, rodentia, and lagomorpha) and agricultural animals (e.g., bovine, equine, ovine, and porcine). In practicing the methods of the present disclosure, the pharmaceutical compositions can be used alone, or in combination with other therapeutic or diagnostic agents.

In an aspect, compositions or nanocarriers comprising charged telodendrimers are used in imaging methods. In an embodiment, a composition or nanocarrier comprises an imaging agent. In an embodiment, the present disclosure provides a method of imaging, including administering to a subject to be imaged, an effective amount of a composition or nanocarrier of the present disclosure, wherein the composition or nanocarrier includes an imaging agent. In other embodiments, the method of treating and the method of imaging are accomplished simultaneously using a nanocarrier having a therapeutic protein, and/or an imaging agent-labeled protein.

DESCRIPTION OF THE DRAWINGS

For a fuller understanding of the nature and objects of the disclosure, reference should be made to the following detailed description taken in conjunction with the accompanying figures.

DETAILED DESCRIPTION OF THE DISCLOSURE

Figure 1:
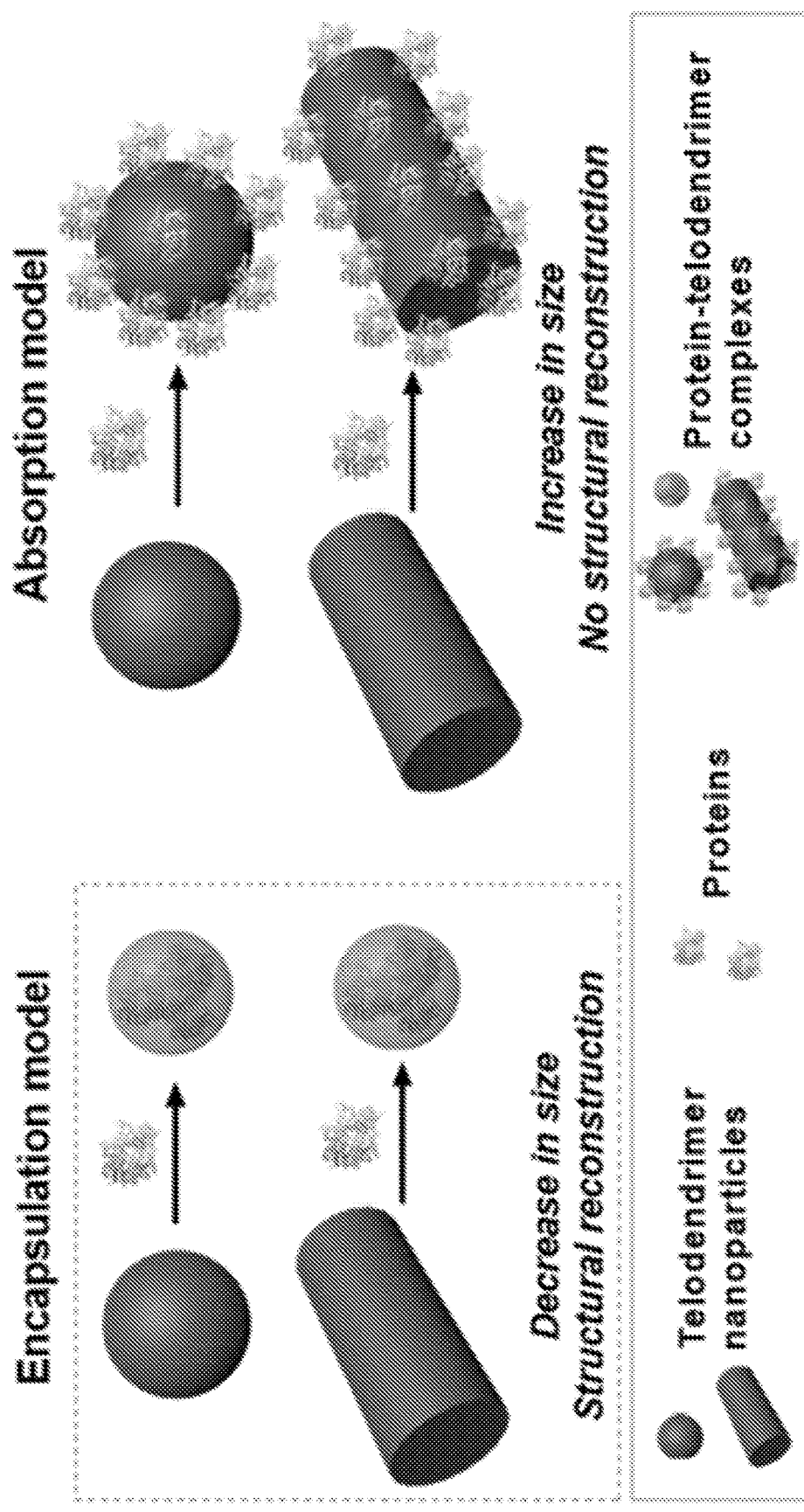
FIG. 1. Hypothetical assembly models of protein-telodendrimer complex.

Although claimed subject matter will be described in terms of certain embodiments and examples, other embodiments and examples, including embodiments and examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

A novel approach to design telodendrimer nanocarriers based on the structure of a molecule of interest by the aid of computational design was developed. Various building blocks can be introduced into telodendrimer backbone in a precisely controlled manner. Through combinatorial telodendrimer synthesis, the properties of nanocarriers, e.g., size, charge and drug loading capacity/stability, can be tuned. This well-defined and highly engineerable telodendrimer platform cam be used, for example, for nanocarrier design for protein delivery.

A functionalized and spatially segregated protein nanocarrier system was developed. The nanocarrier system can be used to deliver one or more proteins. In an embodiment, the nanocarrier system is used to encapsulate a protein by through the use of both a hydrophobic region, to fine-tune particle size, promote protein loading, and cellular uptake, and a charged hydrophilic region, for protein stabilization and loading, and improved cell-penetration properties. In an embodiment, the nanocarrier system is used to deliver one or more proteins.

In this disclosure the synthesis and engineering of a series of well-defined amphiphilic telodendrimers comprised of a linear polyethylene glycol and a dendritic polyelectrolyte decorated with different protein binding moieties is described. For example, these optimized telodendrimers can encapsulate superior amount of proteins (e.g., 30 to 200% of the telodendrimer by weight) by multivalent hybrid interactions to form stable, neutrally charged, sub-30 nm nanoparticles capable of transporting bioactive protein across cellular membranes. This smart platform can be used, for example, for insulin delivery for diabetes and cytotoxic protein delivery for cancer treatment.

The charged telodendrimer shown in FIG. 18 illustrates an example of telodendrimer design that can be used, e.g., to achieve high protein loading and cell-penetration. The various length of polyethylene glycol (ligand layer) serves as hydrophilic segments of the telodendrimer; the adjacent layer was composed of branched architecture capped with hydrophobic natural products and charged species for protein stabilization.

The charged telodendrimers comprise multiple segments. Examples of segments include linear hydrophilic polymer segments, adjacent branched functional segments, charged protein binding segments. The telodendrimers can form nanocarriers (e.g., telodendrimer micelle structures).

Definitions

As used herein, the term "protein" includes peptides (generally 50 amino acids or less), polypeptides (generally, 100 amino acids or less), and proteins (greater than 100 amino acids). The protein can be a therapeutic protein (e.g., a cytotoxic protein or insulin). The protein can be an antibody, enzyme, or other bioactive protein.

As used herein, the term "moiety" refers to a part (substructure) or functional group of a molecule that is part of the telodendrimer structure. For example, 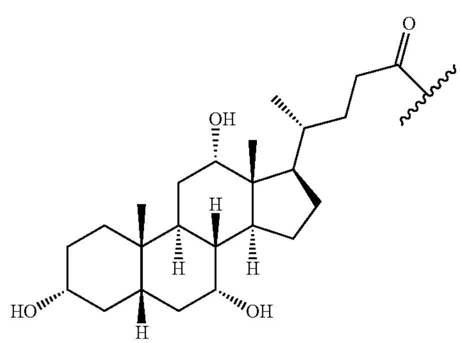 refers to a cholic acid moiety, 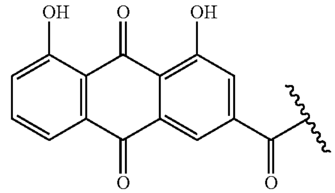 [SMILES: *C(=O)c1cc(O)c2c(c1)C(=O)c1cccc(O)c1C2=O] refers to a rhein moiety, 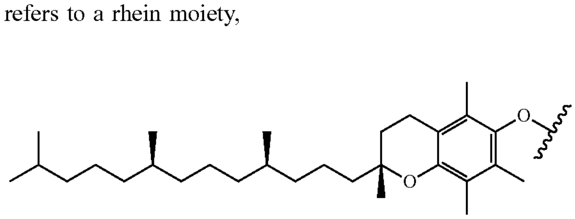 refers to a vitamin E moiety.

As used herein, the terms "dendritic polymer" or "dendritic polymer moiety" refer to branched polymers containing a focal point, a plurality of branched monomer units, and a plurality of end groups. The monomers are linked together to form arms (or "dendritic polymer moiety") extending from the focal point and terminating at the end groups. The focal point of the dendritic polymer can be attached to other segments of the compounds of the disclosure, and the end groups may be further functionalized with additional chemical moieties. The dendritic polymer can be composed of, for example, branched lysine and/or branched arginine moieties.

As used herein, the term "nanocarrier" refers to a micelle resulting from aggregation of telodendrimer conjugates of the present disclosure. The nanocarrier has a hydrophobic core and a hydrophilic exterior.

As used herein, the terms "monomer" and "monomer unit" refer to a diamino carboxylic acid, a dihydroxy carboxylic acid, or a hydroxyl amino carboxylic acid. Examples of diamino carboxylic acid groups of the present disclosure include, but are not limited to, 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present disclosure include, but are not limited to, glyceric acid, 2,4-dihydroxybutyric acid, glyceric acid, 2,4-dihydroxybutyric acid, 2,2-bis(hydroxymethyl)propionic acid, and 2,2-bis(hydroxymethyl)butyric acid. Examples of hydroxyl amino carboxylic acids include, but are not limited to, serine and homoserine. One of skill in the art will appreciate that other monomer units can be used in the present disclosure. Monomers of the present disclosure can have a bond connectivity of, for example, ,
,
,
 or
.

For example, when a monomer is defined as a lysine moiety, with a bond connectivity of A-Lys-B, where A and B are generic appendages, then it can be assumed that the structure can be any one of the following:

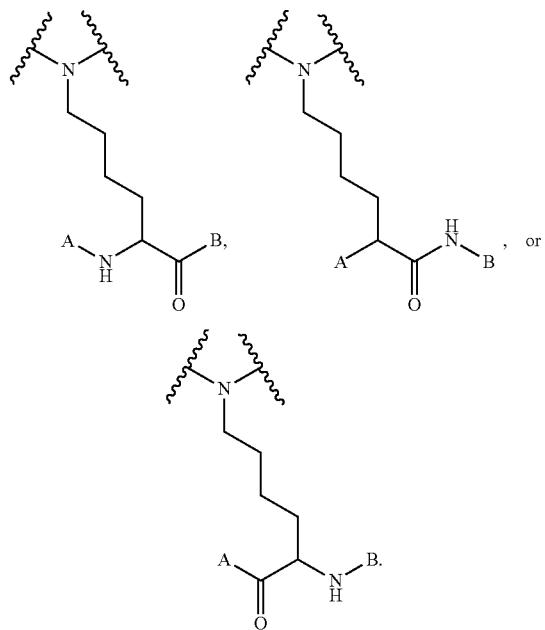

As used herein, the term "linker" refers to a chemical moiety that links (e.g., via covalent bonds) one segment of a dendritic conjugate to another segment of the dendritic conjugate. The types of bonds used to link the linker to the segments of the telodendrimers include, but are not limited to, amides, amines, esters, carbamates, ureas, thioethers, thiocarbamates, thiocarbonate, and thioureas. For example, the linker ($L^1$, $L^2$, $L^3$, and/or $L^4$), individually at each occurrence in the telodendrimer, can be a polyethylene glycol moiety, polyserine moiety, polyglycine moiety, poly (serine-glycine) moiety, aliphatic amino acid moieties, 6-amino hexanoic acid moiety, 5-amino pentanoic acid moiety, 4-amino butanoic acid moiety, and beta-alanine moiety. The linker can also be a cleavable linker. In certain embodiments, combinations of linkers can be used. For example, the linker can be an enzyme cleavable peptide moiety, disulfide bond moiety or an acid labile moiety. One of skill in the art will appreciate that other types of bonds can be used in the present disclosure. In certain embodiments, the linker $L^1$, $L^2$, $L^3$, and/or $L^4$ can be

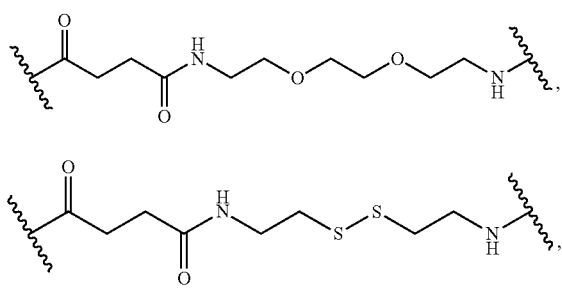 [SMILES: *NCCOCCOCCNC(=O)CCC(*)=O ; *NCCSSCCNC(=O)CCC(*)=O]

or a combination thereof, or other peptide sequence or spacer molecules.

As used herein, PEG group refers to polyethylene glycol. For example, the structure of PEG is

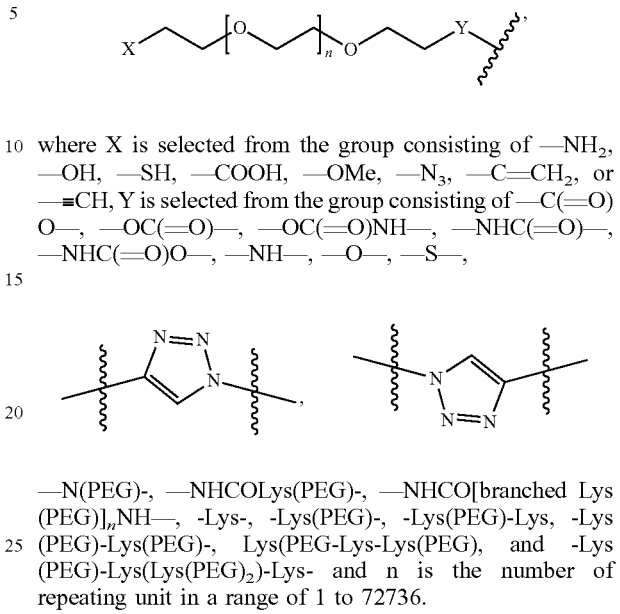

where X is selected from the group consisting of —NH$_2$, —OH, —SH, —COOH, —OMe, —N$_3$, —C≡CH$_2$, or —≡CH, Y is selected from the group consisting of —C(═O) O—, —OC(═O)—, —OC(═O)NH—, —NHC(═O)—, —NHC(═O)O—, —NH—, —O—, —S—, —N(PEG)-, —NHCOLys(PEG)-, —NHCO[branched Lys (PEG)]$_n$NH—, -Lys-, -Lys(PEG)-, -Lys(PEG)-Lys, -Lys (PEG)-Lys(PEG)-, Lys(PEG-Lys-Lys(PEG), and -Lys (PEG)-Lys(Lys(PEG)$_2$)-Lys- and n is the number of repeating unit in a range of 1 to 72736.

As used herein, the term "reversible crosslinking group" refers to a chemical moiety that can be reversible reacted with another chemical moiety that will crosslink and decrosslink when exposed to certain conditions (e.g., different pH condition, chemical environments (e.g. sugar level), redox environments (concentration of glutathione) and UV light of varying wavelength). For example, a coumarin derivative moiety, can be photocrosslinked at >300 nm and decrosslinked at ~265 nm. Another example is catechol and boronic acid which form a boronate crosslinkage, which can be cleaved at acidic pH or with cis-diol containing sugar. Another example is disulfide formation, which can be cleaved under higher concentration of glutathione in vivo. The degree of crosslinking can be controlled by the density of crosslinking moieties and crosslinking conditions, e.g., the time of reversible photocrosslinkable groups are exposed to UV light.

As used herein, the term "oligomer" or "oligomer moiety" refers to fifteen or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, lipids, vitamins, natural compounds, herbal extracts, fluorocarbons, silicones, certain steroids such as cholesterol, bile acids, and certain polymers such as, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as, for example, PEG, PVA.

As used herein, the term "amphiphilic compound" refers to a compound having both hydrophobic portions and hydrophilic portions. For example, the amphiphilic compounds of the present disclosure can have one hydrophilic part of the compound and one hydrophobic part of the compound, for example, bile acids, cholic acids, riboflavin, chlorgenic acid, etc.

As used herein, the term "polar compound" refers to a compound having a non-zero vector sum of its bond dipoles.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals. Suitable examples of mammals include, but are not limited to, primates (e.g., humans), cows, sheep, goats, horses, dogs, cats, rabbits, rats, mice, and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

Charged Telodendrimers. In an aspect, the present disclosure provides charged telodendrimers. The charged telodendrimers are linear-dendritic copolymers. The charged telodendrimers are functional segregated telodendrimers having, for example, two or three functional segments. In an embodiment, the functional segments are a hydrophilic segment and a hydrophobic segment. The hydrophilic segment comprises one or more charged groups. The charged telodendrimers may comprise an intermediate layer. The charged telodendrimers may have one or more crosslinking groups (e.g., boronic acid/catechol reversible crosslinking groups).

The charged telodendrimers may comprise PEG groups that can form a PEG layer. Without intending to be bound by any particular theory, it is considered that the PEG layer serves as a stealth hydrophilic shell to stabilize the nanoparticle and to avoid systemic clearance by the reticuloendothelial system (RES). The intermediate layer, if present, contains for example, optional crosslinkable functional group(s), amphiphilic oligo-cholic acid, riboflavin, or chlorogenic acid and can further stabilize nanoparticle and cage drug molecules in the core of nanoparticle. The interior layer (i.e., hydrophilic layer) comprises positively or negatively charged moieties and may comprise, for example, protein-binding building blocks, such as vitamins (e.g., α-tocopherol, riboflavin, folic acid, retinoic acid, etc.), functional lipids (ceramide), and chemical extracts (e.g., rhein, coumarin, curcurmine, etc.), from herbal medicine to increase the affinity to drug molecules.

In an embodiment, the present disclosure provides charged telodendrimers that are functional and spatially segregated telodendrimers having 1 to 128 charged groups. The telodendrimers may have one or more crosslinking groups (e.g., reversible boronate crosslinking groups). In an embodiment, the telodendrimers are functional segregated telodendrimers having three functional segments.

In an embodiment the disclosure provides a compound of formula (I):

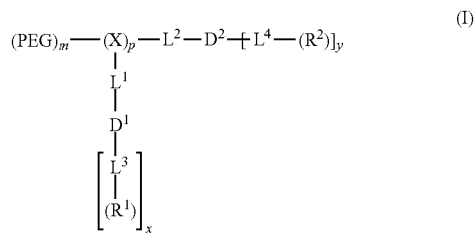

where PEG is optionally present and is a polyethylene glycol moiety, where PEG has a molecular weight of 44 Da to 100 kDa; X is optionally present and is a branched monomer unit; each $L^1$ is independently optional and is a linker group; each $L^2$ is independently optional and is a linker group; each $L^3$ is independently optional and is a linker group; each $L^4$ is independently optional and is a linker group; $D^1$ is optional and is a dendritic polymer moiety having one or more branched monomer units (X), and a plurality of end groups; $D^2$ is a dendritic polymer having one or more branched monomer units (X), and a plurality of end groups; $R^1$ is optional and is an end group of the dendritic polymer and is independently at each occurrence in the compound selected from the group consisting of crosslinkable groups (boronic acid, cisdiols, amine, carboxylic acids, acryl groups, epoxide, thiol groups, malaimide, C=C double bond, azide, alkyne, coumarin and chlorogenic acid etc); $R^2$ is an end group of the dendritic polymer and is independently at each occurrence in the compound selected from the group consisting of positively or negatively charged groups (e.g., arginine, lysine, guanidine, amine, amidine, tetrazole, hydroxyl, carboxyl, phosphate, sulfonate, methanesulfonamide, sulfonamide, or oxalic acid functional groups) and neutral groups (e.g., polar groups, such as sugars, peptides, and hydrophilic polymers), or hydrophobic groups, such as long-chain alkanes ($C_1$-$C_{50}$) and fatty acids ($C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine)), or amphiphilic groups (e.g. cholic acid, riboflavin, chlorogenic acid). The $R^2$ group(s) include at least one positively or negatively charged groups. Subscript x is an integer from 1 to 64, where subscript x is equal to the number of end groups on the dendritic polymer. Subscript y is an integer from 1 to 64, where subscript y is equal to the number of end groups on the dendritic polymer. Subscript p is an integer from 0 to 32. Subscript m is an integer from 0 to 32.

The charged telodendrimers have one or more charged groups (e.g., $R^2$ groups). The charged groups are positively charged groups or negatively charged groups. In an embodiment, all of the charged groups present are positively charged groups. In an embodiment, all of the charged groups are negatively charged groups. In an embodiment, the number of charged groups present in the telodendrimer is 1-128, including all integer numbers of charged groups and ranges therebetween. In an embodiment, the number of charged groups present in the telodendrimer is 2-64. In an embodiment, the number of charged groups present in the telodendrimer is 4-16. In an embodiment, the number of charged groups present in the telodendrimer is 4. In an embodiment, the number of charged groups present in the telodendrimer is 8. When $D^2$ is present and, for example, a branched arginine dendritic moiety, the guanidine portion of the arginine subunits are not part of $D^2$, but rather, the guanidine moiety is an $R^2$ group.

When X is present, in an embodiment, at each occurrence in the compound, the branched monomer unit (X) is independently selected from the group consisting of a diamino carboxylic acid moiety, a dihydroxy carboxylic acid moiety, and a hydroxyl amino carboxylic acid moiety.

$R^2$ is covalently bonded to a dendritic polymer or linker. The $R^2$ groups may be end groups. The $R^2$ groups may be linked to another $R^2$ group or $R^2$ end groups. The $R^2$ group(s) is/are independently at each occurrence in the compound selected from the group consisting of positively or negatively charged groups (e.g., arginine, lysine, guanidine, amine (e.g., secondary, tertiary or quaternary amines), amidine, tetrazole, hydroxyl, carboxyl, phosphate, sulfonate, methanesulfonamide, sulfonamide, or oxalic acid functional groups) and neutral groups (e.g., polar groups: sugars, peptides, hydrophilic polymers, or hydrophobic groups: long-chain alkanes ($C_1$-$C_{50}$) and fatty acids ($C_1$-$C_{50}$), lipids, vitamins, natural compounds, herbal extracts, aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); or amphiphilic groups, cholic acid, riboflavin, chlorogenic acid) where at least one positively or negatively charged groups are present as $R^2$ groups. $R^2$ groups may be directly bonded to the dendritic moiety (e.g. the guanidine portion of an argine moiety), or they may be attached through a linker. When $R^2$ is not an end group each $R^2$ is linked to one of the end $R^2$ groups. In an embodiment, at least one hydrophobic group/moiety is an $R^2$ group.

$R^1$, if present, is covalently bonded to a dendritic polymer or a linker. The $R^1$ groups may be end groups. The $R^1$ groups may be linked to another $R^1$ group or $R^1$ end groups. $R^1$ and can include, for example: crosslinkable groups (boronic acid, cisdiols, amine, carboxylic acids, acryl groups, epoxide, thiol groups, malaimide, C═C double bond, azide, alkyne, coumarin, and chlorogenic acid, etc.). When $R^1$ is not an end group each $R^1$ is linked to one of the end $R^1$ groups.

In various embodiments, the charged telodendrimer compound of the present disclosure has the following structure:

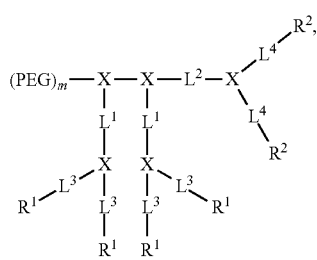

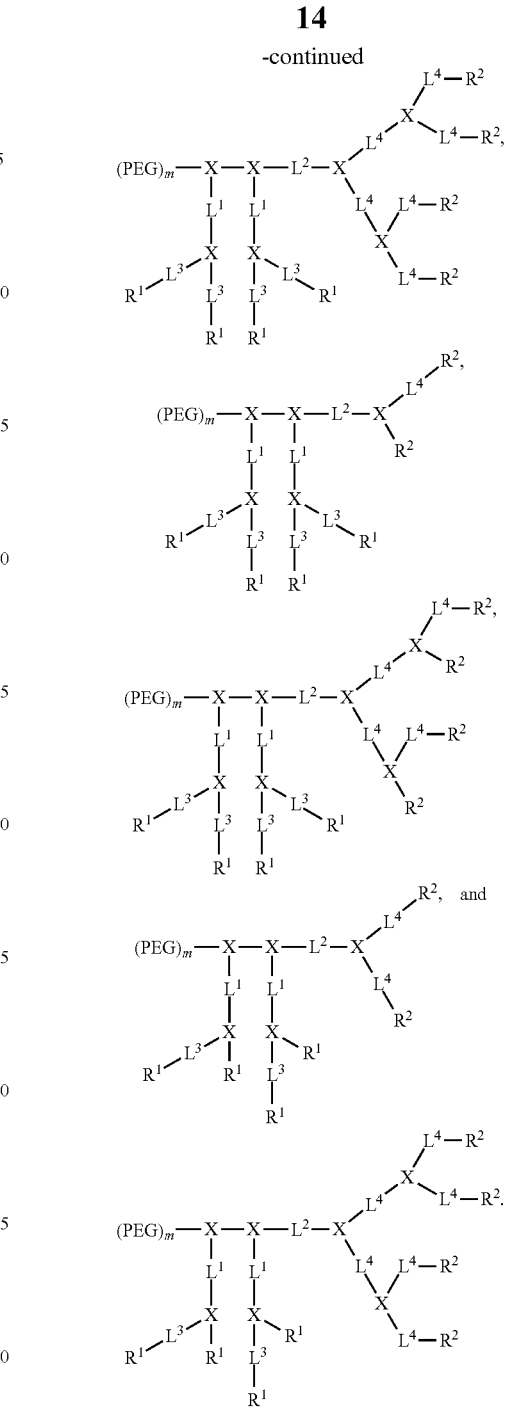

For example, each branched monomer unit is a lysine moiety or an arginine moiety or selected from a lysine moiety and an arginine moiety.

In an embodiment, at each occurrence in the compound the linker (e.g., $L^1$, $L^2$, $L^3$, and/or $L^4$) are independently selected from the group consisting of:

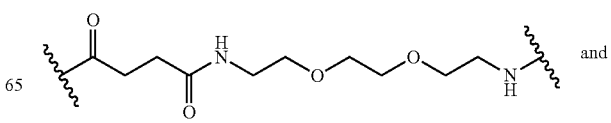

and

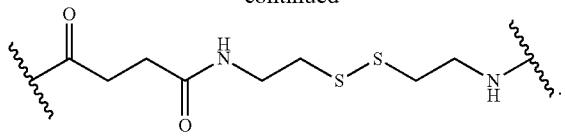

In an embodiment, at each occurrence in the compound the linker (e.g., $L^1$, $L^2$, $L^3$, and/or $L^4$) or a combination thereof comprises a cleavable group. In a specific embodiment, the cleavable group is a disulfide cleavable moiety.

In an embodiment, the PEG portion of the compound is selected from the group consisting of:

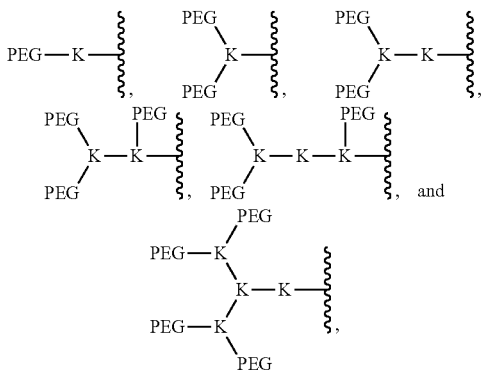

where each K is lysine in the compound of formula (I).

In an embodiment, 0 to 32 of $R^1$ groups, 1 to 32 of $R^2$ groups are charged or neutral groups.

In an embodiment, the reversible crosslinking group (e.g., R'), if present, is a coumarin moiety, 4-methylcoumarin moiety, boronic acid moiety or derivative or analog thereof, catechol moiety or derivative or analog thereof, cis-diol moiety or derivative or analog thereof, cinnamic acid moiety or derivative or analog thereof, chlorogenic acid moiety or derivative or analog thereof, amine moiety or a derivative thereof, carboxylic acid or a derivative thereof, acyl group, or a derivative thereof, epoxide or a derivative thereof, thiol group or a derivative thereof, malaimide or a derivative thereof, alkene or a derivative thereof, azide or a derivative thereof, alkyne or a derivative thereof, comarin or a derivative thereof, or a combination thereof.

The charged group can be any group/moiety with a positive or negative charge. For example, the charged group has a positive or negative charge in aqueous solution at a certain pH. In an embodiment, the charged group (e.g., $R^2$) is a moiety or derivative or analog of arginine, lysine, or guanidine. In an embodiment, the charged group (e.g., $R^2$) is an moiety or derivative or analog of an amine, amidine, tetrazole, hydroxyl, carboxyl, phosphate, sulfonate, sulfonamide (e.g., methanesulfonamide), oxalic acid, or similar functional groups.

In an embodiment, the neutral group is the moiety or derivative or analog of sugars, peptides, hydrophilic polymers, long-chain alkanes ($C_1$-$C_{50}$) and fatty acids ($C_1$-$C_{50}$), aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); amphiphilic groups, cholic acid, riboflavin, chlorogenic acid and natural compound extract and synthetic compounds.

The charged telodendrimers can have various combinations of functional groups (e.g., $R^2$ and, if present $R^1$ groups). The functional groups can be end groups or linked to end groups. In an embodiment, all of the $R^2$ groups present in the charged telodendrimer are all charged groups and the $R^1$ groups, if present, are hydrophobic and/or crosslinking groups. In an embodiment, all of the $R^2$ groups present in the charged telodendrimer are charged groups or hydrophobic groups and the $R^1$ groups, if present, are hydrophobic and/or crosslinking groups.

The dendritic moiety may comprise one or more amino acid moieties (e.g., lysine and/or arginine moieties). For example, it is a polylysine or polyarginine moiety. Amino acid side chains may further provide additional branches or an $R^1$ or $R^2$ group (e.g., a terminal $R^1$ or $R^2$ group). For example, in the case of a polylysine dendritic moiety, the nitrogen of the lysine side chain may further react to form additional branches, or may be an $R^2$ group. Different moieties (e.g., functional groups) may be selectively installed at selected end groups of the dendritic moiety using orthogonal protecting group strategies.

The charged telodendrimers may be used to stabilize proteins. The type of charge, the number of charged groups, the ratio of charged groups to hydrophobic groups (if present), the spatial orientation of the charged groups, and/or the density of the charged groups can be selected to stabilize a specific protein.

Nanocarriers. In an aspect, the present disclosure provides nanocarriers comprising charged telodendrimers. Nanocarriers can also be referred to herein as nanoparticles. In an embodiment, a composition comprises an aggregate of a plurality of the telodendrimers that form a nanocarrier having a hydrophobic core and a hydrophilic exterior.

The nanocarrier may be a telodendrimer micelle. A telodendrimer micelle is a nanoconstruct formed by the self-assembly of the telodendrimer in aqueous solution. The telodendrimer micelle can serve as a nanocarrier to load various types of proteins.

The nanocarriers (e.g., telodendrimer micelles) have a multiple layer (e.g., a two-layer or three-layer) structure. The three-layer structure comprises an intermediate layer.

The empty nanocarriers were examined to be nontoxic in cell culture and the protein-loaded nanoformulations exhibited the similar potency in killing cancer cells in vitro. The resulting nanocarriers exhibit superior protein loading capacity and stability. The optimized nanoparticle is able to targeted deliver the payload cytotoxic proteins to the cancer site.

In an embodiment, the nanocarrier comprises a plurality of charged telodendrimer compounds. In an embodiment, the nanocarrier comprises one or more charged proteins. The nanocarriers comprising one or more charged proteins may have a diameter of 5 nm to 50 nm, including all integer nm values and ranges therebetween. In an embodiment, the nanocarriers comprising one or more charged proteins may have a diameter of 10 nm to 30 nm.

The telodendrimers of the present disclosure can aggregate to form nanocarriers with a hybrid hydrophobic/polyelectrolic core, optionally, an intermediate layer (e.g., a reversible crosslinkable layer), and a hydrophilic exterior. In an embodiment, a plurality of telodendrimers aggregate to form nanocarriers with a hydrophobic and polyelectrolic core and a hydrophilic exterior. In an embodiment, the disclosure provides a nanocarrier having an interior and an exterior, the nanocarrier comprising a plurality of the telodendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG) of each compound self-assembles on the exterior of the nanocarrier. The telodendrimers may encapsulate or form a layer on (e.g., a layer on at least a part of) one or more protein.

The telodendrimers can be designed such that each of the proteins carried will have a different release profile. Examples of conditions that can affect the release profile of carried proteins include time and biological environment.

The nanocarrier may comprise two or more different telodendrimer/protein constructs. Each of the two or more different telodendrimer polymers can each be designed for a different protein combinations (i.e., the affinity layer of each telodendrimer can be tuned to different proteins.).

The nanocarrier can further comprise a polycation material. Examples of polycation materials include, but are not limited to, cationic polymers such as, for example, polyethylenimine (PEI), polylysine, or poly(dimethylaminoethyl methacrylate) (PDMAEMA). Combinations of polycation materials can be used. In various examples, a polycationic material (e.g., a polymer) has a molecular weight of 500 Daltons to 100 kiloDaltons, including all integer Dalton values and ranges therebetween. Various ratios of protein(s) to polycation material(s) can be used. For example, the ratio of protein(s) to polycation material(s) (mass ratio) is 1:1 to 1:40. In another example, the ratio of protein(s) to polycation material(s) (mass ratio) is 1:2. Various ratios of polycation material(s) to telodendrimer(s) can be used. For example, the ratio of polycation material(s) to telodendrimer(s) (mass ratio) is 1:0.05 to 1:20. In another example, the ratio of polycation material(s) to telodendrimer(s) (mass ratio) is 1:1. In an example, the ratio of polycation material(s) to telodendrimer(s) (mass ratio) is 1:1 to 1:40 and the ratio of polycation material(s) to telodendrimer(s) (mass ratio) is 1:0.05 to 1:20.

The protein or protein mixtures can be dissolved in phosphate buffered saline, and telodendrimer(s) in phosphate buffered saline are rapidly added into protein solution. The proteins will interact (e.g., be encapsulated) mainly by the telodendrimers through electrostatic interaction, hydrogen bonding, and hydrophobic-hydrophobic interaction.

For example, each of the telodendrimers can be associated with (e.g., encapsulate) proteins (e.g., a different protein combinations) in separate reactions. Subsequently, the two or more telodendrimer polymer/protein combinations can be combined under such conditions that they form micelles containing a mix of telodendrimer polymer/protein constructs. If, for example, the micelles contain 100 or so individual telodendrimers, it is expected that the "mixed" micelles will contain stochiastic mix of the two or more proteins. The average composition will depend upon the ratio of the 2 or more telodendrimer polymer/proteins constructs in the mixture. The "mixed" micelles can be used to deliver three or more proteins at the same time in a predetermined ratio (e.g., where the ratio is based on the relative starting amounts of the 3 or more proteins).

In the "mixed" micelle embodiment, it may be desirable that each telodendrimer have two different end groups ($R^1$ and $R^2$), where $R^1$ is tuned for particle size, protein stability and hydrophobic interactions and $R^2$ is tuned to provide a charged protein interaction and stabilization.

Some embodiments of the present disclosure provide nanocarriers wherein each amphiphilic compound $R^1$, $R^2$, is independently cholic acid, allocholic acid, pythocholic acid, avicholic acid, deoxycholic acid, or chenodeoxycholic acid.

Protein-loaded telodendrimer nanoparticles of the present disclosure are stable in particle sizes as detected by DLS analysis upon storage in PBS or saline at 4° C. and room temperature within the monitoring duration for 3 months. The activity of cytotoxic protein (DTAT13) and peptide-drug conjugates are remained the same as free therapeutics in cancer cell killing in cell culture.

Protein therapeutics can be released out from the complex via the competition by the high concentration of serum proteins in vivo. The release rate can be tuned by the adjusting the protein binding affinity of telodendrimers. Therefore, protein-nanotherapeutics can be administrated directly for in vivo use without the need to purification of the released protein.

The telodendrimers of the present disclosure can be used to, for example, encapsulate antibodies and other therapeutic proteins and increase the therapeutic index mainly in two-fold: (1) to improve the stability of the protein therapeutics, e.g., antitoxin antibodies, during storage even at room temperature for the possible applications at rural area and military use. They can be developed as onsite-care formulations for direct administration. Antibodies will be released upon serum albumin and IgG competition of nanocarrier. It is also useful to stabilize antibody drugs for routine use to prevent the denaturation due to aggregation. (2) An even broader application is to deliver protein and antibodies reagents into cells, for example, antibodies against intracellular proteins used in biochemistry assays or pathology detections, therefore becoming therapeutic to treat various diseases.

The charged telodendrimers can be present in a composition. In an embodiment, the composition comprises one or more charged telodendrimers. The composition may comprise a mixture of positively charged telodendrimers, a mixture of negatively charged telodendrimers, or a mixture of positively and negatively charged telodendrimers. In an embodiment the composition further comprises one or more proteins. In an embodiment the composition further comprises one or more drugs. The composition can have a formulation as disclosed herein. For example, the composition can be a pharmaceutical composition as described herein.

Any charged protein can be used. For example, the protein is a positively charged or negatively charged protein. In an embodiment, the protein is an imaging agent-labeled protein. In an embodiment, the composition comprises or nanocarriers encapsulate an amount of protein(s) that is 30-200% of the telodendrimer present in the composition or nanocarriers by weight, including all integer weight % values and ranges therebetween.

Examples of therapeutic proteins that can be used include nucleoproteins, glycoproteins, lipoproteins, immunotherapeutic proteins, porcine somatotropin for increasing feed conversion efficiency in a pig, insulin, growth hormone, buserelin, leuprolide, interferon, gonadorelin, calcitonin, cyclosporin, lisinopril, captopril, delapril, tissue plasminogen activator, epidermal growth factor, fibroblast growth factor (acidic or basic), platelet derived growth factor, transforming growth factor (alpha or beta), vasoactive intestinal peptide, tumor necrosis factor; hormones such as glucagon, calcitronin, adrecosticotrophic hormone, follicle stimulating hormone, enkaphalins, β-endorphin, somatostin, gonado trophine, α-melanocyte stimulating hormone. Additional examples include bombesin, atrial naturiuretic peptides and luteinizing hormone releasing (LHRH), substance P, vasopressins, α-globulins, transferrins, fibrinogens, β-globulins, prothrombin (bovine), ceruloplasmin, $\alpha_2$-glycoproteins, α₂-globulins, fetuin (bovine), albumin and prealbumin, bovine serum albumin, green fluorescent protein, diphtheria toxins, lysozyme, trypsin, cytochrome c, saporin, ribonuclease A, IgG, and antibodies.

The nanocarriers may comprise one or more drugs. The drugs can be therapeutic agents. The drugs may be sequestered in the nanocarriers (e.g., sequestered in one or more of the layers of a telodendrimer) or linked to the conjugates of the present disclosure. Examples of drugs include, but are not limited to, cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present disclosure include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17alpha-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the disclosure.

In an aspect, the present disclosure provides methods of using the telodendrimers. The telodendrimers can be used, for example, in methods of treatment.

Method of treating. The compositions or nanocarriers of the present disclosure can be used to treat any disease requiring the administration of a protein, such as, for example, by sequestering a protein in the interior of the nanocarrier, and delivering said protein to a target. The protein(s) can be delivered systemically or intracellularly. In an embodiment, compositions comprising the telodendrimers are used in a method for treating a disease.

In some embodiments, the present disclosure provides a method of treating a disease, including administering to a subject in need of such treatment a therapeutically effective amount of a composition or nanocarrier of the present disclosure, where the nanocarrier includes an encapsulated protein.

The compositions or nanocarriers of the present disclosure can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the compositions or nanocarriers of the present disclosure include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the compositions or nanocarriers of the present disclosure are useful for the treatment of infection by pathogens such as viruses, bacteria, fungi, and parasites. Other diseases can be treated using the compositions or nanocarriers of the present disclosure.

Formulations. The nanocarriers of the present disclosure can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present disclosure (see, e.g., *Remington's Pharmaceutical Sciences*, 20ᵗʰ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present disclosure suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the disclosure in a sustained release formulation.

Pharmaceutical preparations useful in the present disclosure also include extended-release formulations. In some embodiments, extended-release formulations useful in the present disclosure are described in U.S. Pat. No. 6,699,508, which can be prepared according to U.S. Pat. No. 7,125,567, both patents are incorporated herein by reference.

The pharmaceutical preparations are typically delivered to a mammal, including humans and non-human mammals. Non-human mammals treated using the present methods include domesticated animals (e.g., canine, feline, murine, rodentia, and lagomorpha) and agricultural animals (e.g., bovine, equine, ovine, porcine).

In practicing the methods of the present disclosure, the pharmaceutical compositions can be used alone, or in combination with other therapeutic or diagnostic agents.

Administration. The nanocarriers of the present disclosure can be administered as frequently as necessary, including hourly, daily, weekly or monthly. The compounds utilized in the pharmaceutical method of the disclosure are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present disclosure should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present disclosure, the pharmaceutical compositions can be used alone, or in combination with other therapeutic or diagnostic agents. The additional proteins used in the combination protocols of the present disclosure can be administered separately or one or more of the proteins used in the combination protocols can be administered together, such as in an admixture. Where one or more proteins are administered separately, the timing and schedule of administration of each protein can vary.

Method of imaging. In an aspect, compositions or nanocarriers comprising charged telodendrimers are used in imaging methods. In an embodiment, a composition or nanocarrier comprises an imaging agent.

In an embodiment, the present disclosure provides a method of imaging, including administering to a subject to be imaged, an effective amount of a composition or nanocarrier of the present disclosure, wherein the composition or nanocarrier includes an imaging agent. In other embodiments, the method of treating and the method of imaging are accomplished simultaneously using a nanocarrier having a therapeutic protein, and/or an imaging agent-labeled protein.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present disclosure include, but are not limited to, $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

The steps of the method described in the various embodiments and examples disclosed herein are sufficient to carry out the methods of the present disclosure. Thus, in an example, the method consists essentially of a combination of the steps of the methods disclosed herein. In another example, the method consists of such steps.

The following Statements describe various examples of the polymers and methods of the present disclosure:

Statement 1. A compound of formula (I):

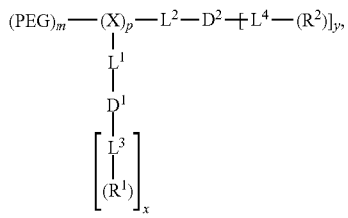

where PEG is optionally present and is a polyethylene glycol moiety, where PEG has a molecular weight of 44 Da to 100 kDa; X is optionally present and is a branched monomer unit; each $L^1$ is independently optional and is a linker group; each $L^2$ is independently optional and is a linker group; each $L^3$ is independently optional and is a linker group; each $L^4$ is independently optional and is a linker group; $D^1$ is optional and is a dendritic polymer moiety having one or more branched monomer units (X), and a plurality of end groups; $D^2$ is a dendritic polymer having one or more branched monomer units (X), and a plurality of end groups; $R^1$ is optional and is an end group of the dendritic polymer and is independently at each occurrence in the compound selected from the group consisting of crosslinkable groups (boronic acid, cis diols, amine, carboxylic acids, acryl groups, epoxide, thiol groups, malaimide, C=C double bond, azide, alkyne, coumarin and chlorogenic acid etc); $R^2$ is an end group of the dendritic polymer and is independently at each occurrence in the compound selected from the group consisting of positively or negatively charged groups (e.g., arginine, lysine, guanidine, amine, amidine, tetrazole, hydroxyl, carboxyl, phosphate, sulfonate, methanesulfonamide, sulfonamide, or oxalic acid functional groups) and neutral groups (e.g., polar groups: sugars, peptides, hydrophilic polymers, or hydrophobic groups: long-chain alkanes ($C_1$-$C_{50}$) and fatty acids ($C_1$-$C_{50}$), aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine), and amphiphilic groups, cholic acid, riboflavin, chlorogenic acid), where at least one positively or negatively charged groups are present in $R^2$; subscript x is an integer from 1 to 64, where subscript x is equal to the number of end groups on the dendritic polymer; subscript y is an integer from 1 to 64, where subscript y is equal to the number of end groups on the dendritic polymer; subscript p is an integer from 0 to 32; and subscript m is an integer from 0 to 32.

Statement 2. A compound according to Statement 1, where at each occurrence in the compound the branched monomer unit (X) is independently selected from the group consisting of a diamino carboxylic acid moiety, a dihydroxy carboxylic acid moiety, and a hydroxyl amino carboxylic acid moiety.

Statement 3. A compound according to Statement 2, where at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid.

Statement 4. A compound according Statement 2, where the diamino carboxylic acid moiety is an amino acid moiety.

Statement 5. A compound according to any one of the preceding Statements, where each branched monomer unit X is lysine moiety.

Statement 6. A compound according to any one of the preceding Statements, where the compound is selected from the group consisting of:

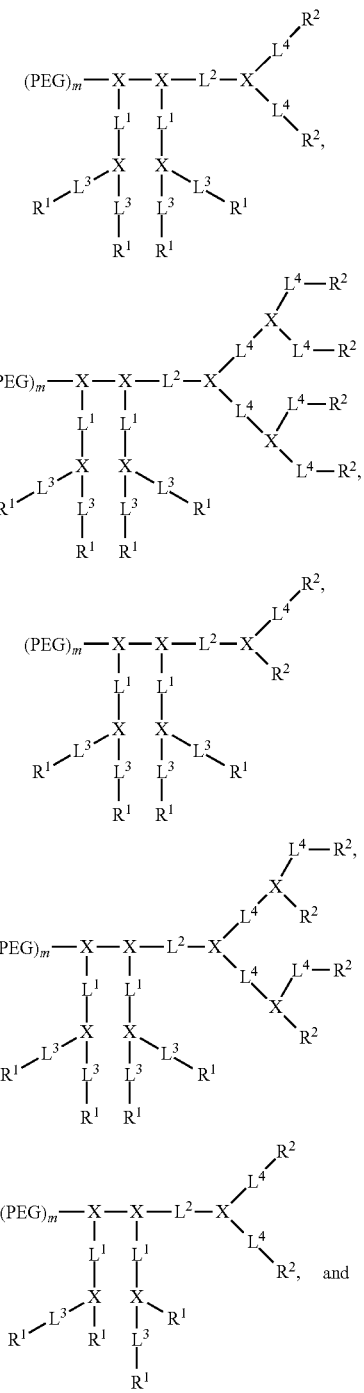

-continued

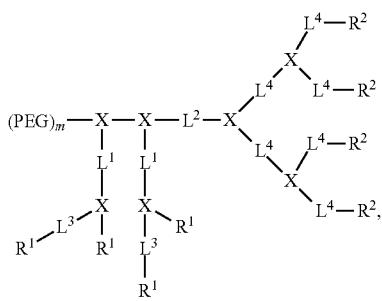

where each branched monomer unit is individually selected from a lysine moiety (e.g., a polylysine moiety) and arginine (e.g., polyarginine) moiety.

Statement 7. A compound according to any one of the preceding Statements, where at each occurrence in the compound the linker $L^1$, $L^2$, $L^3$ and $L^4$ each are independently selected from the group consisting of a polyethylene glycol moiety, polyserine moiety, enzyme cleavable peptide moiety, disulfide bond moiety and acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. Statement 8. A compound according to any one of the preceding Statements, where at each occurrence in the compound the linker $L^1$, $L^2$, $L^3$ and $L^4$ are independently selected from the group consisting of:

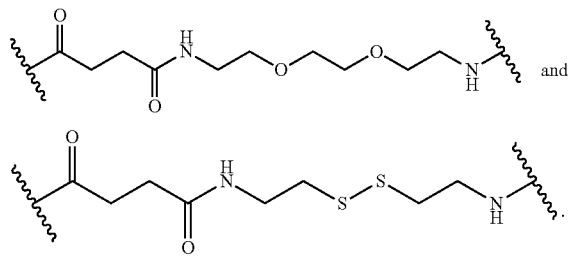

Statement 9. A compound according to any one of the preceding Statements, wherein one or more linker ($L^1$, $L^2$, $L^3$, $L^4$ or a combination thereof) comprises a cleavable group.

Statement 10. A compound according to Statement 9, where the cleavable group is a disulfide cleavable moiety.

Statement 11. A compound according to any one of the preceding Statements, where the (PEG)$_m$ portion of the compound is selected from the group consisting of:

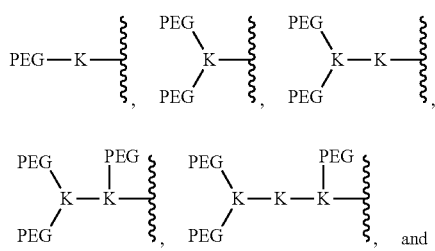

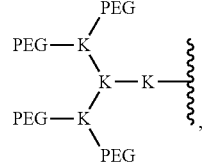

where each K is lysine.

Statement 12. A compound according to any one of the preceding Statements, where at least one (e.g., 1 to 128) of the $R^2$ groups are charged groups and, optionally, at least one of the $R^2$ groups are neutral groups, and, optionally, at least one of (e.g., 1 to 128) of the $R^1$ groups, if present, are reversible crosslinking groups.

Statement 13. A compound according to Statement 12, where the reversible crosslinking group(s) is/are coumarin moiety, 4-methylcoumarin moiety, boronic acid moiety or derivative or analog thereof, catechol moiety or derivative or analog thereof, cis-diol moiety or derivative or analog thereof, cinnamic acid moiety or derivative or analog thereof, chlorogenic acid moiety or derivative or analog thereof, amine moiety or a derivative thereof, carboxylic acid or a derivative thereof, acyl group, or a derivative thereof, epoxide or a derivative thereof, thiol group or a derivative thereof, malaimide or a derivative thereof, alkene or a derivative thereof, azide or a derivative thereof, alkyne or a derivative thereof, coumarin or a derivative thereof, or a combination thereof.

Statement 14. A compound according to Statement 12, where the charged group is the moiety or derivative or analog of arginine, lysine, guanidine, amine, amidine, tetrazole, hydroxyl, carboxyl, phosphate, sulfonate, methanesulfonamide, sulfonamide, or oxalic acid and functional groups Statement 15. A compound according to any one of the preceding Statement 12, where the neutral group is the moiety or derivative or analog of sugars, peptides, hydrophilic polymers, long-chain alkanes ($C_1$-$C_{50}$) and fatty acids ($C_1$-$C_{50}$), aromatic molecules, esters, halogens, nitrocompounds, anthracyclines, fluorocarbons, silicones, certain steroids such as cholesterol, terpenoids, vitamins, and polymers (e.g., PLGA, polycaprolactone, polylactic acid, polyglycolic acid, polystyrene and polyisoprene, polyvinyl pyridine); amphiphilic groups, cholic acid, riboflavin, chlorogenic acid and natural compound extract and synthetic compounds.

Statement 16. A nanocarrier comprising a plurality of compounds according to any one of the preceding Statements.

Statement 17. A nanocarrier according to Statement 16, where the nanocarrier further comprises one or more charged proteins.

Statement 18. A nanocarrier according to any one of Statements 16 or 17, where the nanocarrier further comprises one or more polycation material (e.g., one or more cationic polymer).

The following example is presented to illustrate the present disclosure. It is not intended to limiting in any manner.

Example 1

The following is an example of the preparation, characterization, and use of charged telodendrimers of the present disclosure.

The interplay of hydrogen bonding, electrostatic and hydrophobic interactions stabilizes and maintains protein three-dimensional structures. Polar amino acids, including both positive and negative charged ones, are mostly displayed on the surface of protein to maintain dispersion in aqueous solution. In addition, the hydrophobic residues aggregate into the hydrophobic groves to minimize solvent exposure. The design of polymers to target both hydrophobic grove and polar groups on the protein surface represents a promising solution for protein coating. The multivalent interactions can significantly increase the binding affinity between telodendrimer and proteins. The combination of electrostatic and hydrophobic moieties in telodendrimer is important for protein binding kinetically and thermodynamically. Inspired by the cooperativity and/or multivalency effects in biological systems, we developed a hand-shaped hybrid telodendrimer of a linear polyethylene glycol (PEG) and a dendritic polyelectrolyte decorated with different hydrophobic natural compounds tethered by a flexible linker. We hypothesized the design of telodendrimers with flexible and dendritic hybrid multiple functional groups will match protein surface curvatures by both electrostatic and hydrophobic interactions, which serve approaching and annealing functions, respectively, to stabilize the nanoconstructs. These multivalent hybrid interactions ensure the stable single layer protein-coating by telodendrimers in aqueous solution, thereby yielding nanoparticles of 10-30 nm in size capable of stably loading high amount of proteins. To this end, four or eight guanidine groups were introduced in the dendritic polyamino acids of the telodendrimers to optimize the protein loading and cell-penetration properties, and diverse natural compounds including heptadecanoic acid (C17), cholesterol (CHO) and vitamin E (VE, D-α-tocopherol) were selected as hydrophobic moieties in the telodendrimer nanoparticles to fine-tune the particle size and to further promote the protein loading and cellular uptake. The resultant protein-loaded telodendrimer nanoparticles of <30 nm in diameter have neutral zeta potential (<±5 mV) and high protein loading capacities (>30% of the nanoparticles by weight), and they are colloidally stable for months in phosphate buffered saline (PBS). The telodendrimer nanoparticles can efficiently deliver proteins such as cytotoxins intracellularly to cancer cells while maintaining protein bioactivity, leading to desired cell death.

Herein we report the synthesis and engineering of a series of well-defined amphiphilic telodendrimers comprised of a linear polyethylene glycol and a dendritic polyelectrolyte decorated with different hydrophobic natural compounds. The structure optimization studies showed that both charge interactions and hydrophobic interactions were essential for protein coating/encapsulation. Further, the nature of the charged group and the structure of hydrophobic segments can be optimized for efficient and stable protein encapsulation. These optimized telodendrimers can encapsulate superior amount of proteins (30-200% of the telodendrimer by weight) to form neutral and stable, sub-30 nm nanoparticles capable of delivering bioactive protein across cellular membranes. Such highly engineerable telodendrimers allows for the fine tune of the density, location and ionic strength of the charge groups, as well as the tether length and the structure of the hydrophobic segments to design nanocarriers based on the protein structures, e.g., charge density, structure of the hydrophobic groves. The reversibly crosslinkable functional groups could be introduced in the telodendrimers to further stabilize protein encapsulation, which is responsive to biological/pathological environments, e.g., glucose level in blood or acidic tumor extracelluar or lysosome pH for telodendrimer decrosslinking to release protein therapeutics on demand to treat disease efficiently. This smart platform has been designed specifically for insulin delivery for diabetes and cytotoxic protein delivery for cancer treatment, respectively.

Reversible crosslinking groups can be introduced in the adjacent layer of the teloenderimer to enable nanoparticle crosslinking after protein loading. The reversible crosslinkages, e.g. boronate ester and acid labile acylhydrazone, redox sensitive S—S bonds can respond to the biological or pathological environment to release the protein on demand to achieve better specificity and efficacy.

Synthesis of telodendrimer. We would make the above mentioned telodendimer via step-wise peptide chemistry. Briefly, the telodendimer would be synthesized using a solution-phase condensation reaction starting from MeO-PEG-NH$_2$.HCl. Orthogonally protected peptides such as (Fmoc)Lys(Fmoc)-OH, (Fmoc)Lys(Boc)-OH, and Fmoc-Arg(Pbf)-OH are reacted with the N terminus of PEGylated molecules using diisopropyl carbodimide and N-hydroxybenzotriazole as coupling reagents until a negative Kaiser test result is obtained, indicating completion of the coupling reaction. PEGylated molecules are precipitated through the addition of the cold ether and then washed with cold ether twice. Fmoc groups are removed by the treatment with 4-methylpiperidine in dimethylformamide, and Boc and Pbf groups are removed via the treatment with trifluoroacetic acid in dichloromethane. The linker molecules and hydrophobic molecules are coupled to the de-protected amino groups of the PEGylated molecules to yield the telodendrimer, wherein the positively charged groups are obtained upon the de-protection of Fmoc, Boc or Pbf on the orthogonally protected peptides.

For introducing other charged moieties instead of side chains of lysine and arginines, free amino groups on lysine side chain will be used to conjugate positively or negatively charged groups, e.g. secondary, tertiary and quaternary amines or negative carboxylic, oxalic, sulfonic or phohspyrilic acids, etc.

Figure 14:
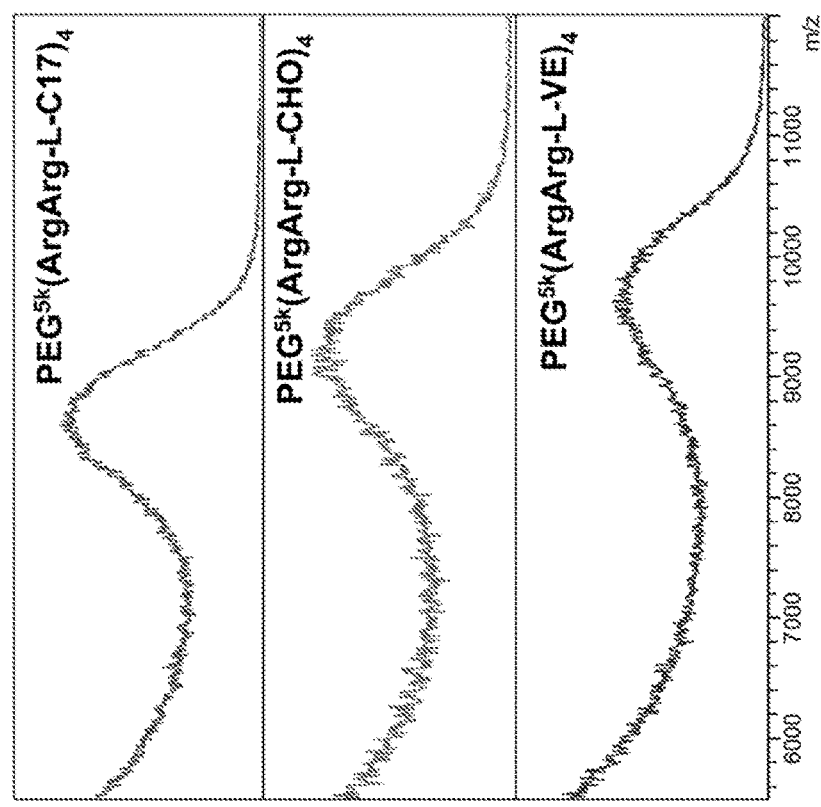
FIG. 14. MALDI-TOF MS of telodendrimers containing eight guanidine groups.
Figure 13:
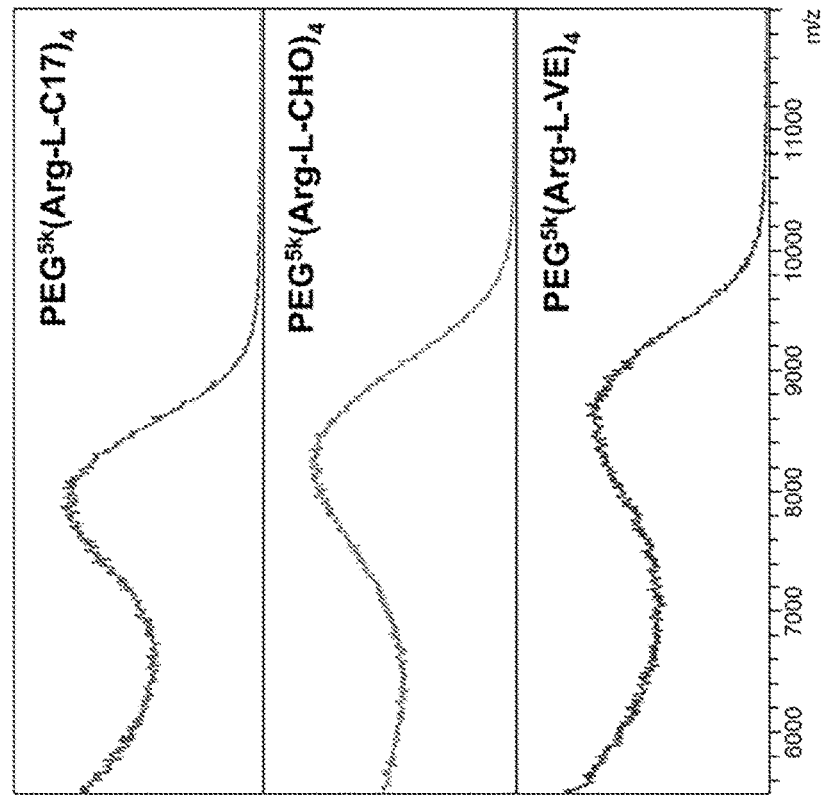
FIG. 13. MALDI-TOF MS of telodendrimers containing four guanidine groups.
Figure 18:
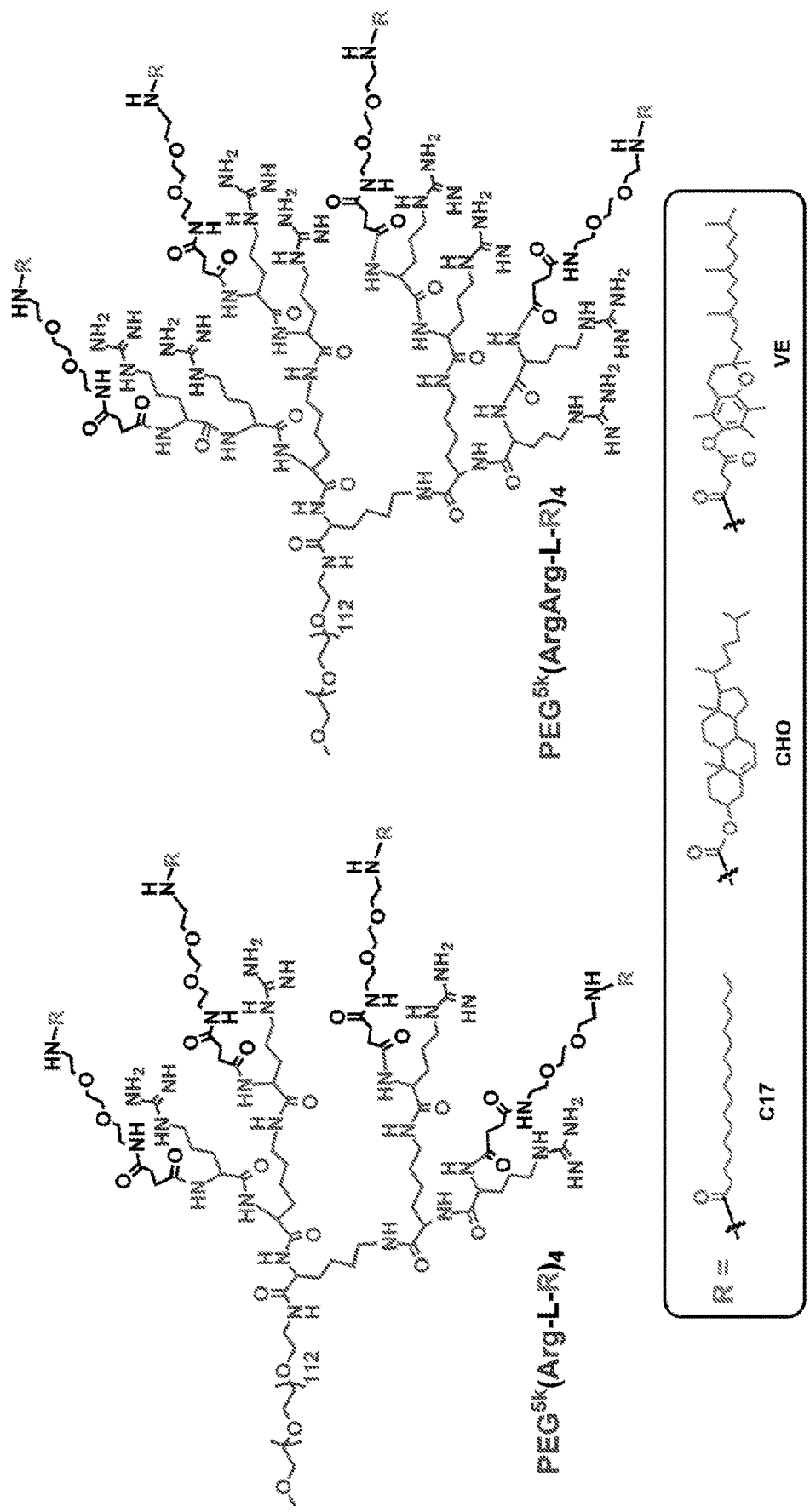
FIG. 18. The hand-shaped chemical structures of telodendrimers containing four (left) or eight (right) guanidine groups.

Results and Discussion. Synthesis and Characterization of Telodendrimers. The design of the telodendrimer with both guanidine groups and hydrophobic compounds lies in follow: The positively charged guanidine groups in the telodendrimers are supposed to interact with oppositely charged groups on protein surface while the flexible-linker-conjugated hydrophobic groups are expected to bind the hydrophobic residues of proteins to offer dual supramolecular interactions to enforce the binding to proteins. The telodendrimers were synthesized via step-wise peptide chemistry. The telodendrimers containing four guanidine groups and four hydrophobic molecules such as C17, CHO and VE are noted as PEG$^{5k}$(Arg-L-C17)$_4$, PEG$^{5k}$(Arg-L-CHO)$_4$ and PEG$^{5k}$(Arg-L-VE)$_4$, respectively, and the eight guanidine group-containing ones are named as PEG$^{5k}$(ArgArg-L-C17)$_4$, PEG$^{5k}$(ArgArg-L-CHO)$_4$ and PEG$^{5k}$(ArgArg-L-VE)$_4$. Their chemical structures are displayed in FIG. 18, and their synthesis routes are shown in Schemes 8 and 9. The telodendrimers were characterized by MALDI-TOF mass spectrometry (MS) and proton nuclear magnetic resonance (NMR), and the results are displayed in Table 1 and FIGS. 13 and 14. Table 1 shows that the molecular weights of the telodendrimers determined by MALDI-TOF MS are very close to the theoretical values. The $^1$H NMR spectra for the telodendrimers in DMSO-d$_6$ also confirm their well-defined chemical structures. The telodendrimers can self-assemble into micelles in PBS due to microphase segregation, yielding monodispersed nanoparticles with hydrodynamic diameters (D$_h$) of 11-32 nm and neutral zeta potential (Table 1). The morphology of the telodendrimer nanoparticles was characterized by transmission electron microscopy (TEM). The telodendrimers containing C17 or CHO as the peripheral groups formed spherical micelles while the VE-containing telodendrimers tend to produce heterogeneous nanoparticles that are spherical and cylindrical in shape due to the pi-pi stacking between VE groups. The particle sizes measured from the TEM images acquire a good agreement with the DLS results. The critical micelle concentrations (CMCs) of the telodendrimers in PBS are in a range from 1.14 to 2.68 µM, which were determined by a fluorescent method employing Nile red as a probe (Table 1. The low CMCs of the telodendrimers suggest the formation of stable micelles in a wide concentration range.

Figure 2:
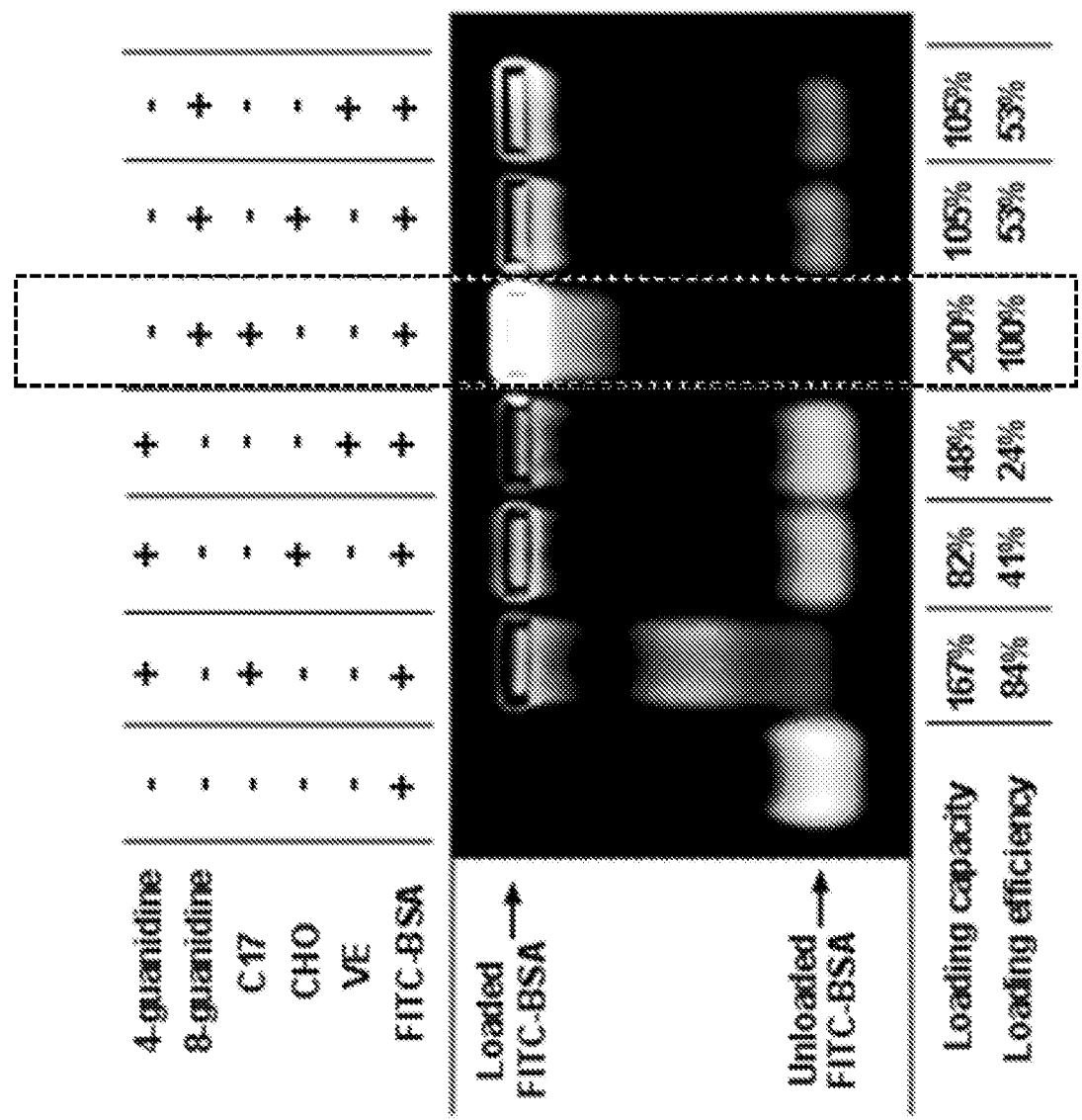
FIG. 2. Loading ability of telodendrimers containing 4 or 8 guanidine groups with C17, CHO or VE hydrophobic groups for FITC-BSA determined by an agarose gel retention assay. The feed mass ratio is 2/1 (P/T).

Incorporation of Proteins within Telodendrimer Nanoparticles. Negatively charged proteins can be effectively loaded in the telodendrimer nanoparticles mainly based on electrostatic and hydrophobic interactions. An agarose gel retention assay was used to semi-quantitatively determine the loading capacity of the telodendrimer nanoparticles for proteins, where the free proteins and protein-loaded telodendrimer nanoparticles could be separated based on their differences in size and charge. Fluorescein isothiocyanate (FITC) labeled bovine serum albumin (BSA), noted as FITC-BSA, was used as a fluorescent model protein for probing the protein position in the agarose gel. A constant amount of FITC-BSA without and with telodendrimer nanoparticles at a protein to telodendrimer (P/T) mass ratio of 2/1 (FIG. 2) were loaded in the agarose gel (1.5% wt). After a 2 h of running in Tris-acetate-EDTA (TAE) buffer, FITC-BSA without telodendrimers migrated a certain distance towards the anode, while the FITC-BSA were trapped in the wells when they were loaded in the telodendrimer nanoparticles due to the large sizes and neutral surface charges of the protein-loaded nanoparticles. Excess FITC-BSA in the protein-telodendrimer systems also migrated a distance roughly equal to that for FITC-BSA without telodendrimers. The loading capacities of the telodendrimer nanoparticles for FITC-BSA were calculated from the fluorescence signals of the bands for unloaded FITC-BSA. As shown in FIG. 2, all the telodendrimer nanoparticles can efficiently incorporate FITC-BSA with loading capacities of more than 30% by weight. The loading capacity and loading efficiency for the telodendrimers containing eight guanidine groups are higher than that for the telodendrimers containing four guanidine groups, and C17-containing telodendrimers have higher protein loading capacities when compared to the CHO— or VE-containing ones. Among these telodendrimers, $PEG^{5k}(ArgArg-L-C17)_4$ highlighted by a dotted square in FIG. 2 shows the best protein loading behavior with a loading capacity of 200% and a loading efficiency of 100% for FITC-BSA. These facts indicate that the precise control on the numbers of guanidine groups and the species of hydrophobic groups is critical to optimize the protein loading behaviors of the telodendrimer nanoparticles.

Figure 3:
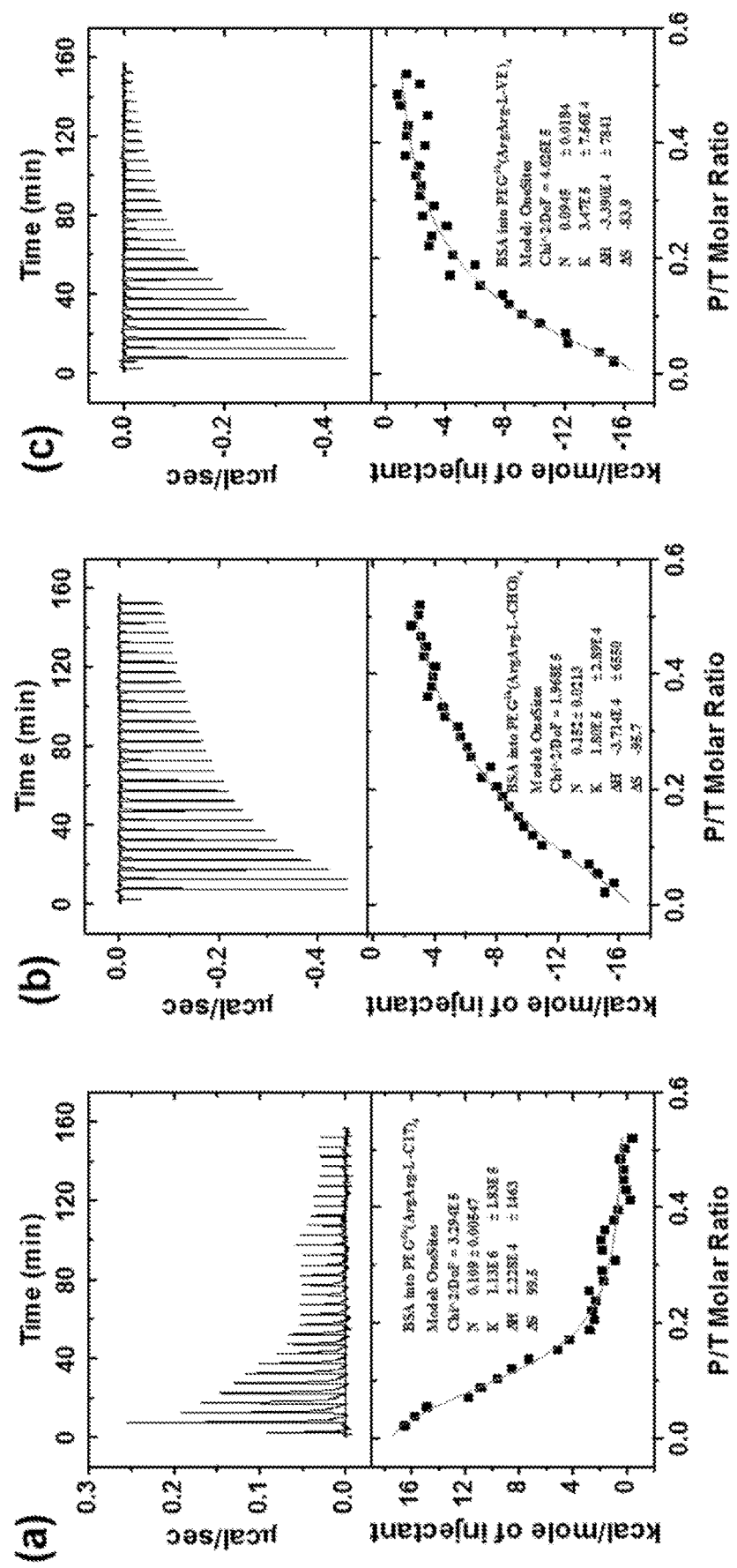
FIG. 3. Calorimetric titration of $PEG^{5k}(ArgArg-L-C17)_4$ (a), $PEG^{5k}(ArgArg-L-CHO)_4$ (b), and $PEG^{5k}(ArgArg-L-VE)_4$ (c) with BSA at 37° C. in PBS (lx).

The binding affinities of proteins to telodendrimers were measured by isothermal titration calorimetry (ITC). BSA and the telodendrimers containing eight guanidine groups with different hydrophobic moieties were dissolved in PBS (1×), and BSA was titrated into the telodendrimer solutions at 37° C. As shown in FIG. 3, the equilibria for the telodendrimers containing rigid CHO or VE hydrophobic molecules were exothermic and defined the overall negative enthalpy of the complexation process (FIGS. 3b and 3c). The individual peaks in the thermograms were integrated by the instrument software and the isotherms were fitted using one-site binding model to yield the stoichiometry, binding affinity ($K_a$), binding enthalpy (ΔH), which are displayed in Table 2. The numbers of BSA equivalents incorporated into telodendrimer nanoparticles are in a range of 0.09 to 0.15, which means the P/T mass ratios in the protein-telodendrimer nanoparticles are close to 1/1, confirming that high amounts of proteins can bind to the telodendrimers. The binding affinities of CHO— and VE-containing telodendrimers for BSA are $1.8 \times 10^5$ and $3.5 \times 10^5$, respectively (Table 2).

To further confirm the binding between telodendrimer and protein, FITC-labeled $PEG^{5k}(ArgArg-L-C17)_4$ (noted as $FITC-PEG^{5k}(ArgArg-L-C17)_4$) and Rhodamine B-labeled BSA (noted as RB-BSA) molecules were selected as a donor-acceptor pair to investigate the molecular proximity by Förster resonance energy transfer (FRET) technique. The data shows that $FITC-PEG^{5k}(ArgArg-L-C17)_4$ could be excited by a light source with a wavelength of 439 nm, and it showed a emission peak centered at 528 nm, while RB-BSA could hardly be excited. When using the same light source to excite 1/1 (w/w) mixture of $FITC-PEG^{5k}(ArgArg-L-C17)_4$ and RB-BSA, except the peak for $FITC-PEG^{5k}(ArgArg-L-C17)_4$ at 528 nm, another peak centered at 584 nm appeared, which related to RB-BSA. It testified the FRET of this donor-acceptor pair that occurred when the distance between the protein and telodendrimer was less than 10 nm, indicating the strong protein-telodendrimer binding. In comparison, no obvious FRET was observed for the mixture of RB-BSA and FITC-BSA, while the addition of $PEG^{5k}(ArgArg-L-C17)_4$ to mixture of RB-BSA and FITC-BSA to reach a P/T ratio of 1/1 by weight led to a significant increase in fluorescence at 584 nm and decrease in fluorescence at 528 nm, that was also observed in the protein-telodendrimer systems with other telodendrimer species or P/T mass ratios. This fact indicates that complexation with telodendrimers brings the proteins with two different dyes together. We suggest that the RB-BSA loaded in the telodendrimer nanoparticles can be released upon the disintegration of the supramolecular structures and in a manner of exchange within other proteins in serum, such as BSA. To clarify it, different amounts of BSA were added in the mixtures of $FITC-PEG^{5k}(ArgArg-L-C17)_4$ and RB-BSA (1/1, w/w), followed by a 4 h incubation at room temperature. We found that the normalized FRET ratio (which was calculated by the formula of $[100\% \times I_{584}/(I_{584}+I_{528})]$, where $I_{584}$ and $I_{528}$ were fluorescence intensities of RB-BSA at 584 nm and $FITC-PEG^{5k}(ArgArg-L-C17)_4$ at 528 nm) generally decreased with increasing BSA concentration (FIG. 4c), indicating dissociation of the telodendrimer nanoparticles with the payload protein in the presence of high amounts of free BSA. This suggested the possible pathway for the payload proteins to be released from the telodendrimer nanoparticles through exchange with other proteins, which was also affirmed by an agarose gel retention assay.

Figure 4:
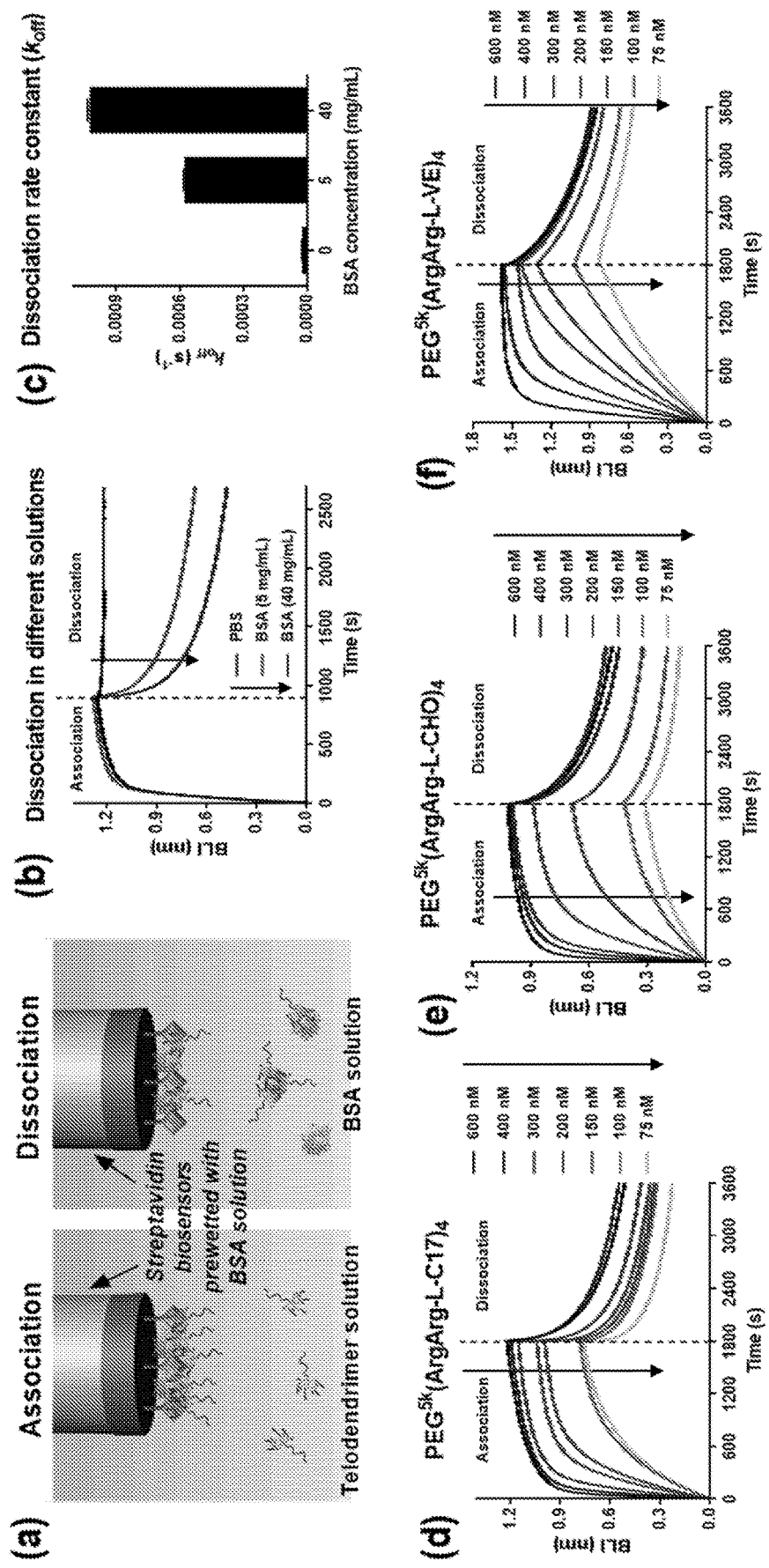
FIG. 4. In vitro binding of telodendrimer to protein measured by BLI. (a) Schematic illustration of the association in telodendrimer solution (left) and dissociation in BSA solution (right) for the streptavidin-coated biosensors prewetted with BSA solution. (b) Kinetics for association in $PEG^{5k}(ArgArg-L-C17)_4$ solution (500 nM) and dissociation in PBS and BSA solutions of different concentrations. (c) Dissociation rate constants determined by fitting the curves in (b). (d-f) Kinetics for association in $PEG^{5k}(ArgArg-L-C17)_4$ (d), $PEG^{5k}(ArgArg-L-CHO)_4$ (e), and $PEG^{5k}(ArgArg-L-VE)_4$ (f) solutions (75-600 nM) and dissociation in BSA solutions (40 mg/mL).

The kinetics of protein-telodendrimer interactions were measured by bio-layer interferometry (BLI). Streptavidin biosensors were prewetted in BSA solution since BSA would occupy most of the nonspecific binding sites on the sensor surfaces, and the association was carried out in telodendrimer solution followed by dissociation in BSA solutions with different concentrations at 37° C. (FIG. 4a). As shown in FIG. 4b, diverse dissociation behaviors are found in different dissociation buffers after binding of $PEG^{5k}(ArgArg-L-C17)_4$ telodendrimers. The dissociation is not efficient in PBS indicating the strong binding between telodendrimers and proteins. The existence of BSA in dissociation buffers significantly accelerates telodendrimer dissociation. Moreover, the dissociation rate constant ($k_{off}$) increases with increasing BSA concentration in dissociation buffers (FIG. 4c), which acquires reasonable agreement with the protein exchange mechanism for protein release from telodendrimer nanoparticles demonstrated from the FRET results. It is a general rule that the binding responses should contain decays in the signal of at least 5% during the dissociation phase of the binding cycle to define a $k_{off}$. To achieve efficient dissociation and mimic serum concentration in vivo, 40 mg/mL of BSA solution is selected as the dissociation buffer for following BLI studies. Multiple concentrations of telodendrimers were used in the association step for different sensors in order to fit results globally and accurately get the binding affinities of telodendrimers to proteins. $PEG^{5k}(ArgArg-L-C17)_4$ is taken as an example to demonstrate global analysis of the BLI data, and the kinetics of association in telodendrimer solutions at a range of concentrations (72-600 nM) and dissociation in 40 mg/mL of BSA solution is shown in FIG. 4d. The association rate constant ($k_{on}$) and $k_{off}$ can be obtained by globally fitting the association and dissociation data to a 1:1 model algorithm, which gives $k_{on}=1.9\times10^4$ (±0.8%) $M^{-1}\cdot s^{-1}$, and $k_{off}=8.1\times 10^{-4}$ (±0.3%) $s^{-1}$. The equilibrium binding constant ($K_D$) can be therefore calculated by as $k_{off}/k_{on}$, which gives $K_D=42$ nM for $PEG^{5k}(ArgArg-L-C17)_4$ telodendrimer with the dissociation buffer of BSA solution (40 mg/mL). For the telodendrimers containing eight guanidine groups, the species of hydrophobic moiety slightly affect the $K_D$ values: C17 groups in the telodendrimer offer stronger binding with proteins when compared to CHO and VE groups (FIGS. 4d-f, and Table 3). This fact may relate to the superhigh protein loading capacity of C17-containing telodendrimers. For the telodendrimers having an identical hydrophobic moiety such as CHO, the $K_D$ value of the four guanidine-containing one is much larger than that for the eight guanidine-containing one due to slow association (small $k_{on}$, see Table 3). It testifies the reduction of the approaching functionalities of charged guanidine groups in the telodendrimers causes decrease in association rate.

Figure 15:
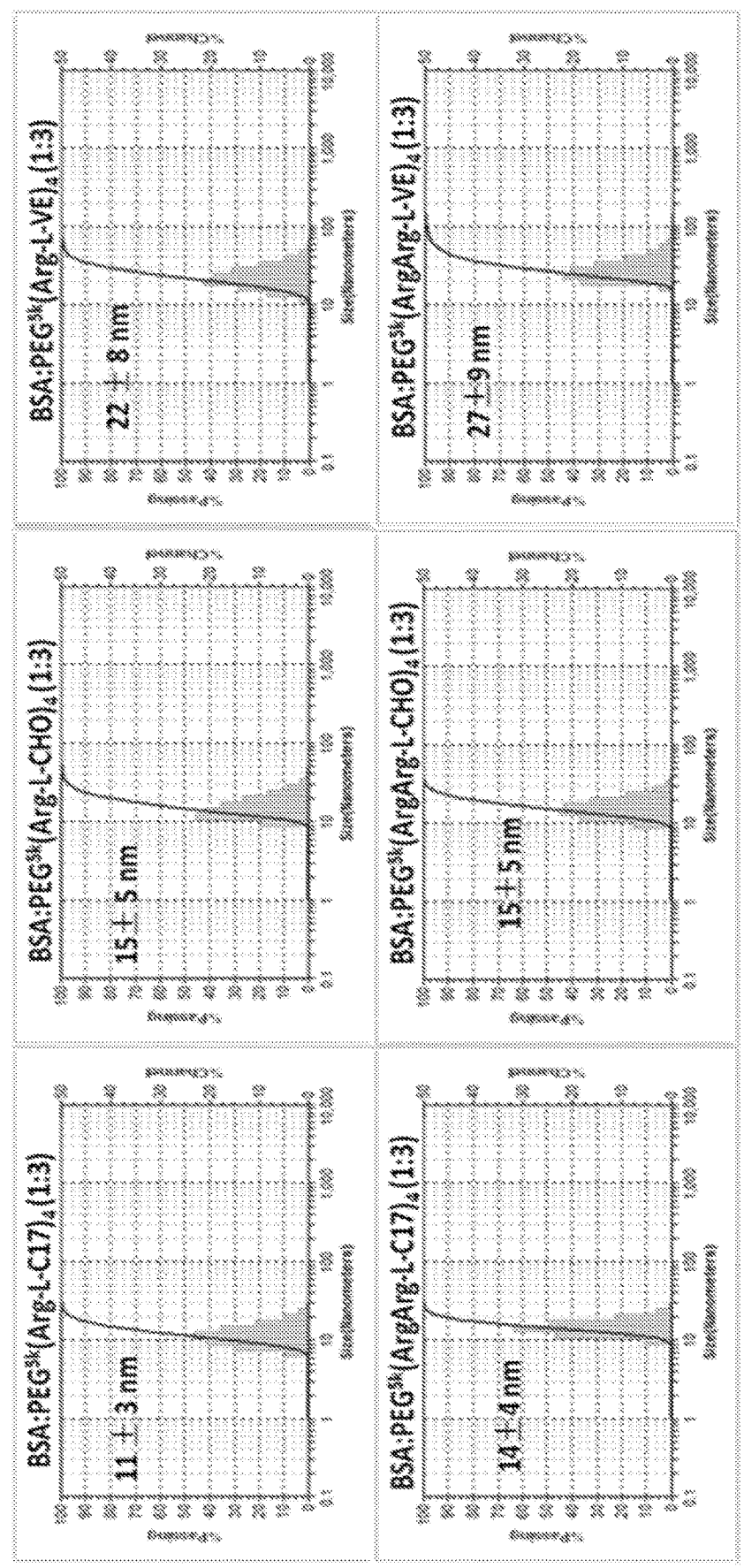
FIG. 15. Hydrodynamic diameters of the BSA-loaded telodendrimers containing four (upper row) or eight (lower row) guanidine groups at a loading ratio of BSA to telodendrimer of 1/3 by weight in PBS (1×) at a telodendrimer concentration of 1 mg/mL after a storage at 4° C. for 2 months.

The sizes of protein-loaded telodendrimer nanoparticles slightly decrease with increasing loading ratio of P/T, as demonstrated by the dynamic light scattering (DLS) studies. The zeta potential of the protein-loaded telodendrimer nanoparticles generally decreases with increasing loading ratio of P/T. When P/T mass ratio reaches 1/3, the protein-loaded telodendrimer nanoparticles have particle sizes of 10-30 nm, and neutral zeta potential (<±5 mV), and this P/T mass ratio (1/3) is therefore considered optimal for following studies. Notably, the protein-loaded telodendrimer nanoparticles have excellent stability, and they are colloidally stable in PBS during a storage of 2 months at 4° C. (Table 1 and FIG. 15). The sizes of the telodendrimer nanoparticles before and after protein loading are generally stable in a pH range from 4.7 to 10. The protein-loaded telodendrimer nanoparticles are narrow-dispersed and are generally spherical in shape, even for the VE-containing ones. It testifies that the hydrophobic VE groups in the telodendrimers interact with the hydrophobic residues of the proteins that can effectively break the stacking between VE molecules leading to the disintegration of elongated nanoparticles. Two pieces of evidence may guide us to understand the binding model of telodendrimer coatings on proteins by reassembly of the telodendrimer micelles ("encapsulation model" highlighted by a dotted square in FIG. 1 (left), but not the model of proteins absorbed on the surfaces of telodendrimer micelles ("absorption model" in FIG. 1 (right): (1) The telodendrimer nanoparticle sizes decrease after loading of proteins. (2) A structural reconstruction occurs for some telodendrimer nanoparticles after protein loading.

Figure 5:
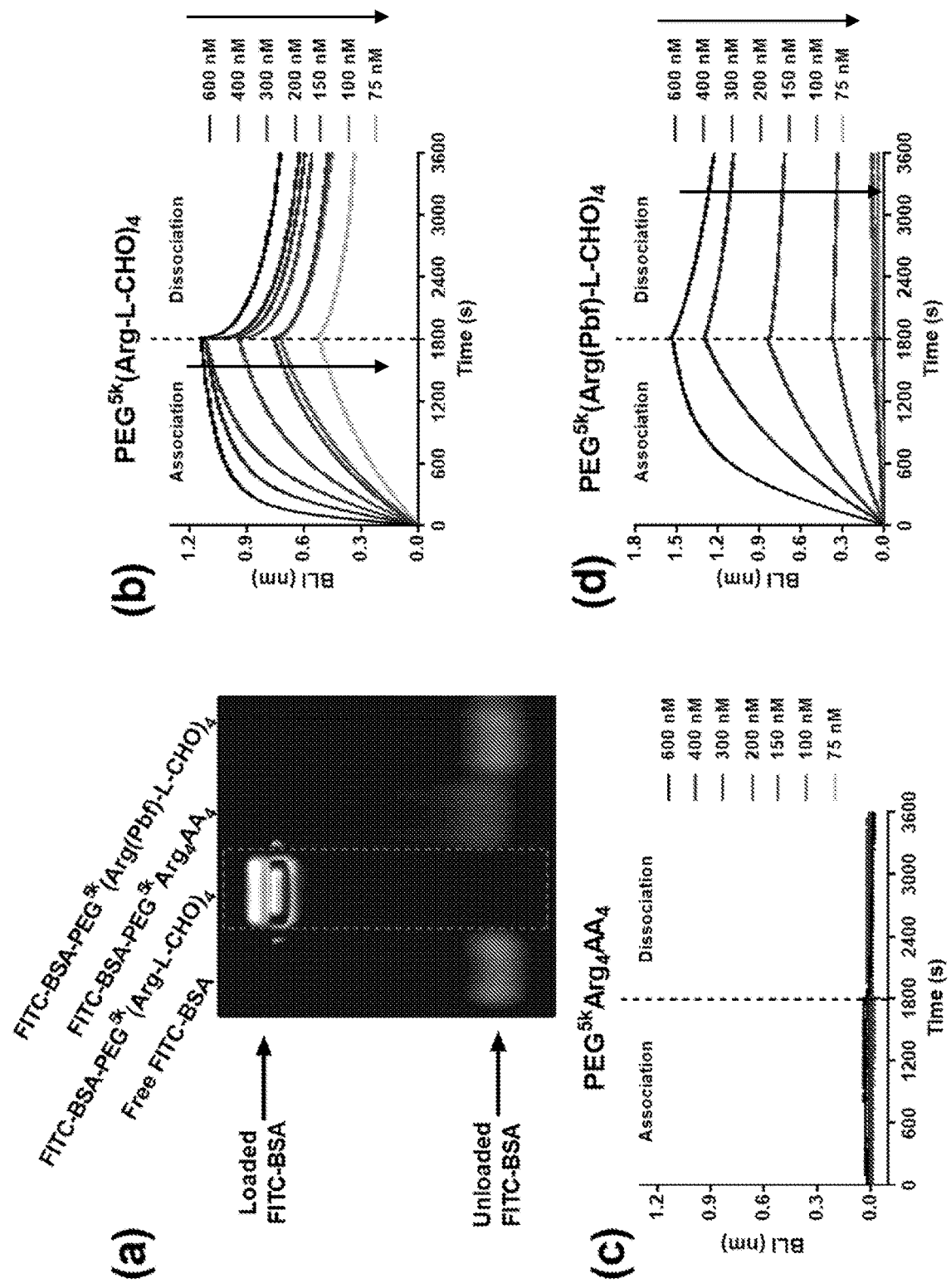
FIG. 5. Determination of the roles of charged and hydrophobic moieties in telodendrimers for protein binding. (a) Loading ability of different telodendrimers for FITC-BSA determined by an agarose gel retention assay. The feed mass ratio of is 1/3 (P/T). (b-d) Kinetics for association in $PEG^{5k}(Arg-L-CHO)_4$ (b), $PEG^{5k}Arg_4AA_4$ (c), and $PEG^{5k}(Arg(Pbf)-L-CHO)_4$ (d) solutions (75-600 nM) and dissociation in BSA solution (40 mg/mL) measured by BLI.
Figure 10:
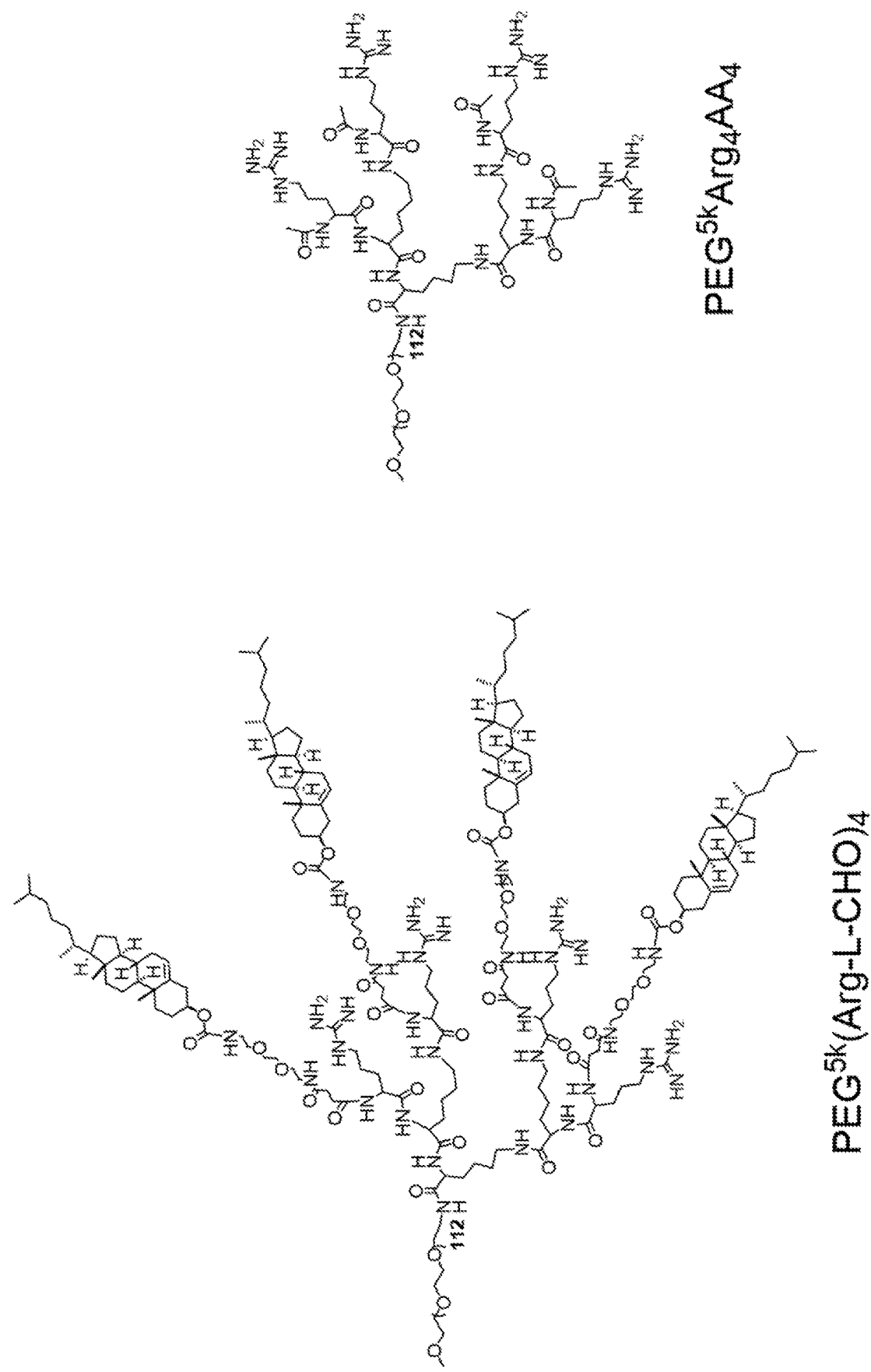
FIG. 10. Chemical structures of telodendrimers containing guanidine groups and/or cholesterol groups.
Figure 10:
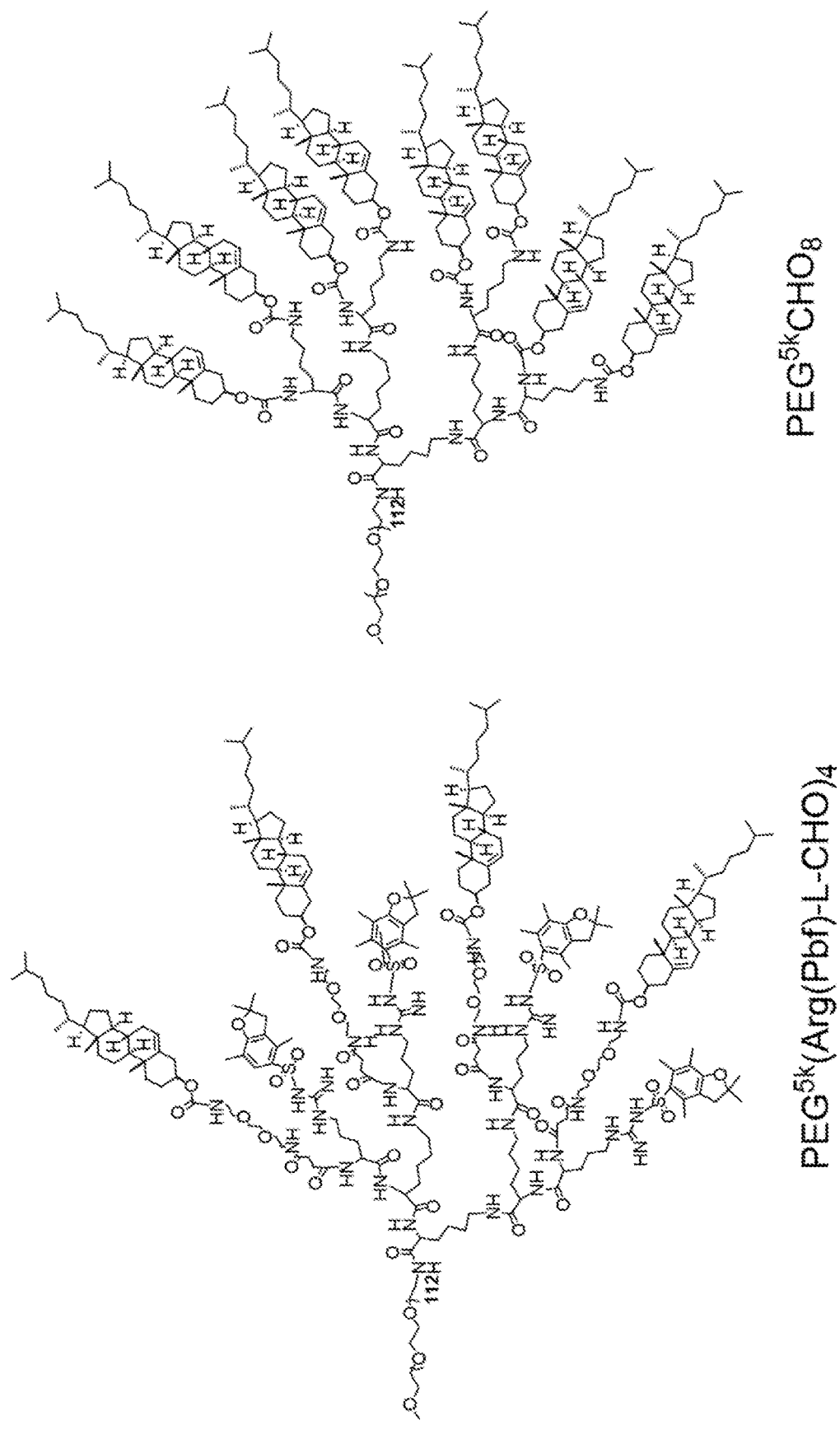
Figure 10:
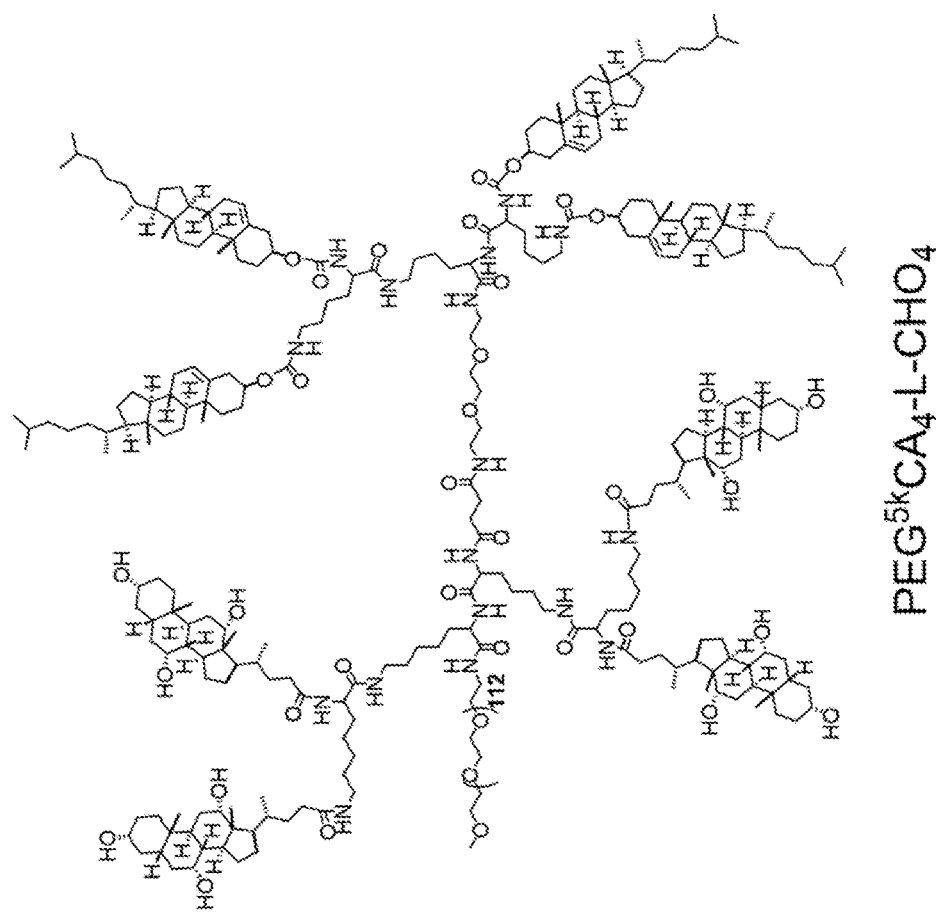
Figure 10:
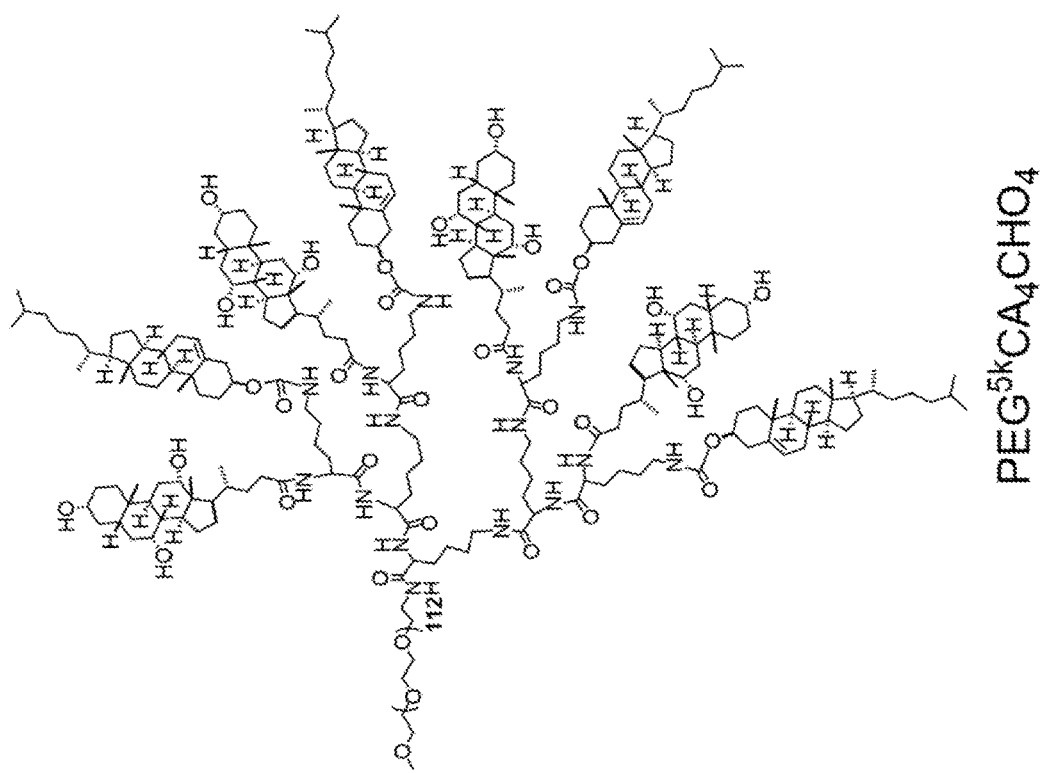
Figure 11:
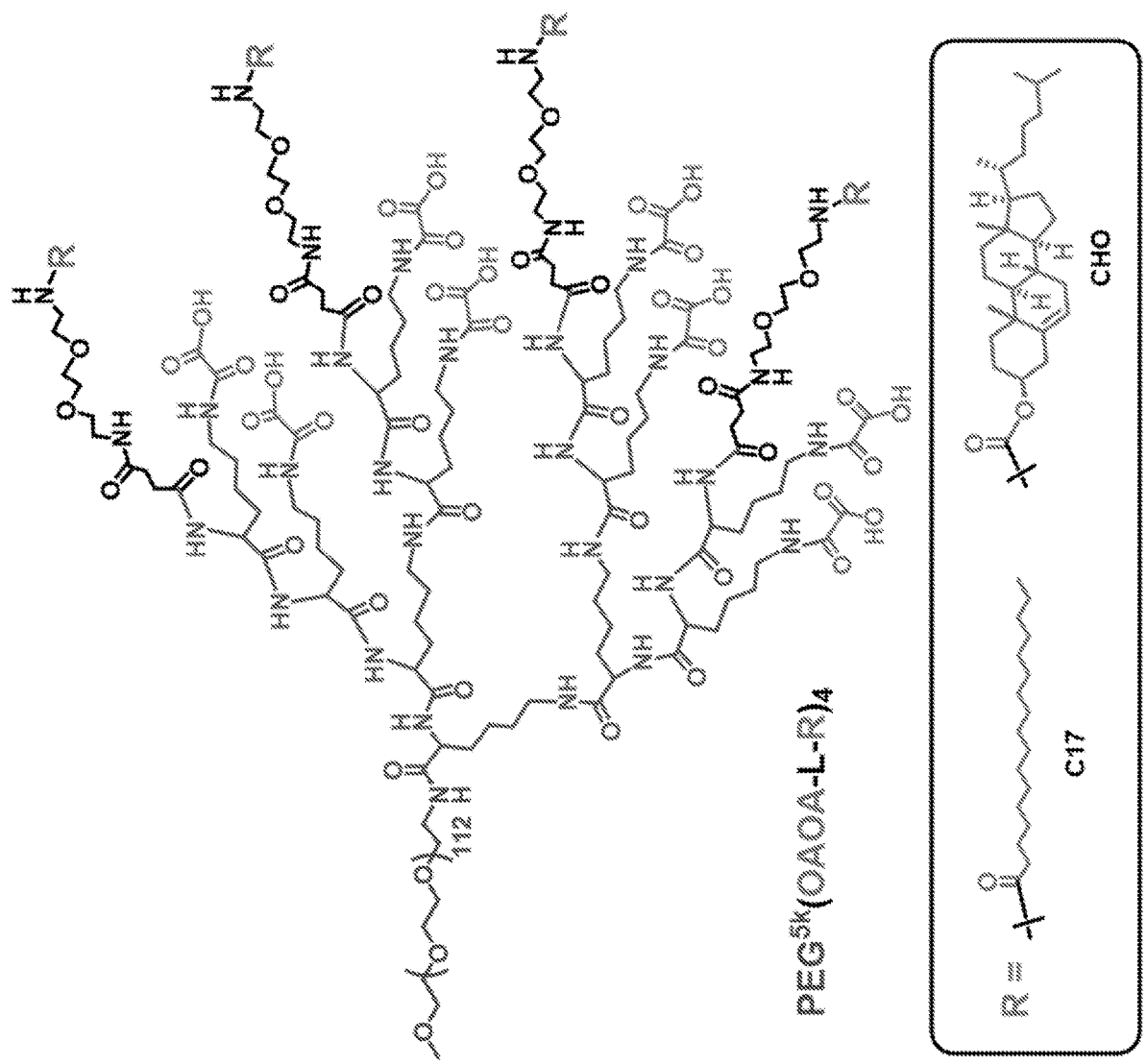
FIG. 11. Chemical structure of telodendrimers containing eight oxalic acid groups, named as $PEG^{5k}(OAOA-L-R)_4$.
Figure 12:
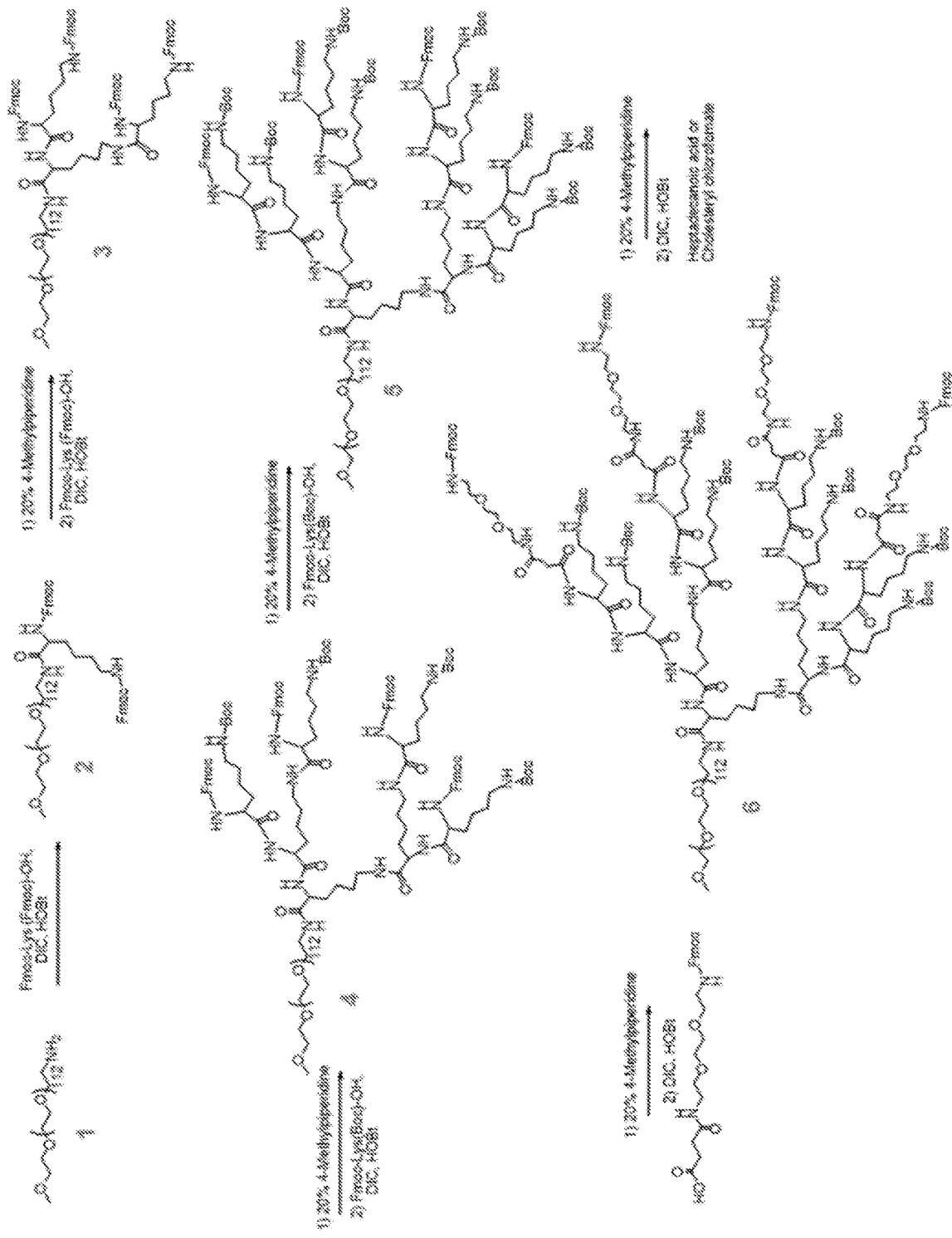
FIG. 12. Synthesis route for telodendrimers containing eight oxalic acid groups, $PEG^{5k}(OAOA-L-R)_4$.
Figure 12:
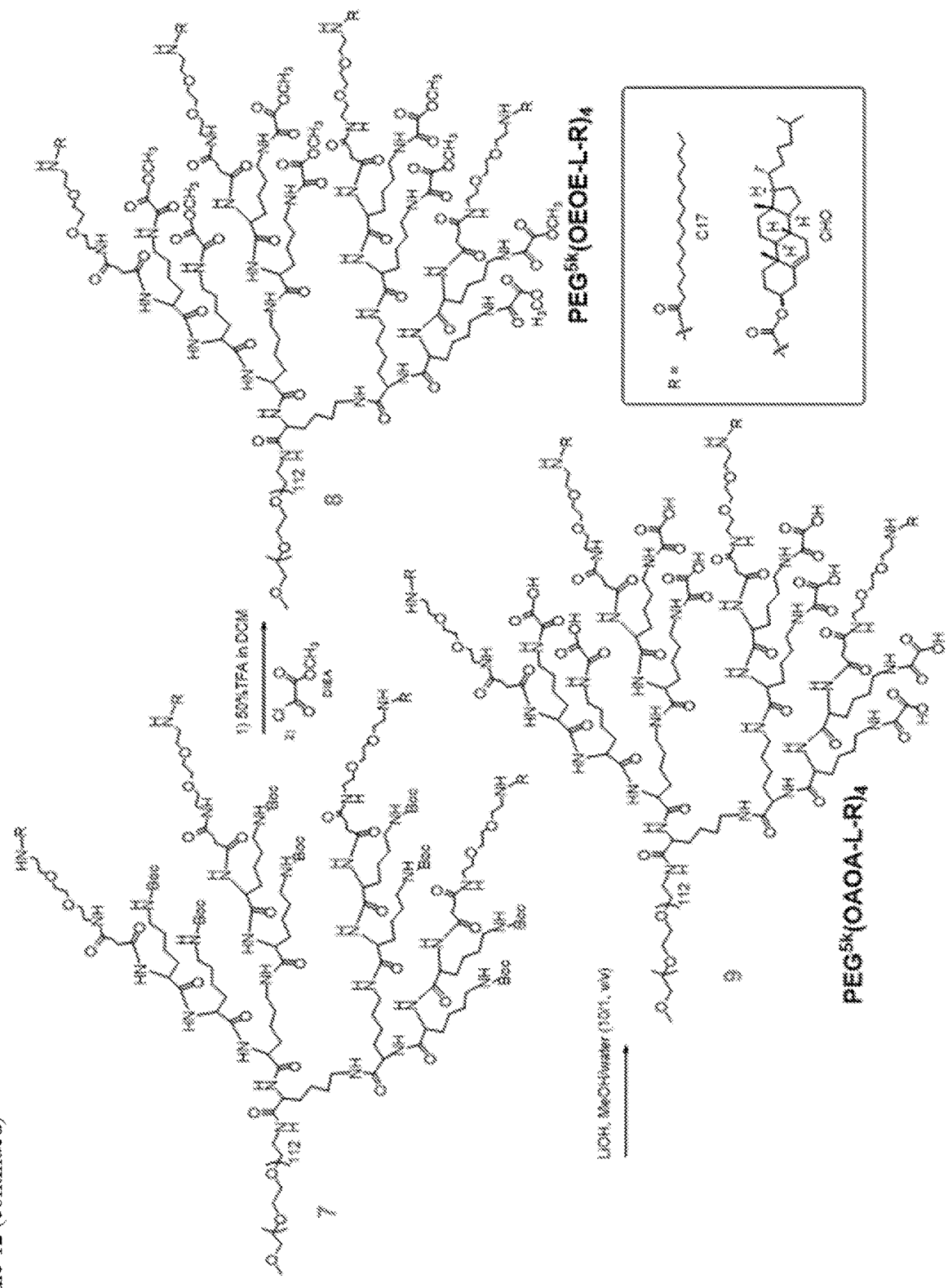

The cooperation of the multivalent charge interactions and hydrophobic interactions between telodendrimers and proteins are considered to be crucial for effective protein encapsulation. To test this hypothesis, a positively charged telodendrimer with N-acetylated polyarginines and without hydrophobic groups (named as $PEG^{5k}Arg_4AA_4$), and a telodendrimer of $PEG^{5k}(Arg(Pbf)-L-CHO)_4$ with hydrophobic CHO groups and without charged groups (guanidine groups in the telodendrimer were protected by Pbf protecting groups) were used as controls to compare the protein loading behaviors with $PEG^{5k}(Arg-L-CHO)_4$. The chemical structures of these telodendrimers are displayed in FIG. 10. The agarose gel retention assay indicated that single type of non-covalent interaction of either electrostatic or hydrophobic interaction was not efficient to encapsulate or retain the proteins in the telodendrimer nanoparticles under electric field. Only $PEG^{5k}(Arg-L-CHO)_4$ telodendrimer with dual functionalities highlighted by a dotted square could retard proteins from migration along electric field, indicating loaded in the nanoparticles with bigger sizes and neutral charges (FIG. 5a). Notably, the delayed migration of FITC-BSA conjugated with $PEG^{5k}Arg_4AA_4$ was because of the electrostatic interactions in the complex that hindered the separation of proteins and telodendrimers with opposite charges under electric field. Three other telodendrimers with hydrophobic CHO groups and without charged groups (chemical structures displayed in FIG. 10—$PEG^{5k}$ $CHO_8$, $PEG^{5k}CA_4CHO_4$, $PEG^{5k}(CA_4-L-CHO_4)$) were also used in the agarose gel retention assay, and they showed similar migration behaviors with $PEG^{5k}(Arg(Pbf)-L-CHO)_4$. BLI was employed to further investigate the roles of charged and hydrophobic moieties in the telodendrimers for protein loading. As shown in FIG. 5b, $PEG^{5k}(Arg-L-CHO)_4$ with dual functionalities triggered a fast association (Table 3). We suggest that the fast association is related to both of the charged and hydrophobic moieties that serve an approaching function for protein capture and play an annealing role to stabilize the captured proteins in the nanoparticles, respectively. Without annealing function by hydrophobic groups, the telodendrimer having only charged moiety was unable to stably bind to proteins on the sensors mainly due to the highly dynamic association-dissociation (FIG. 5c). On the other hand, the telodendrimer with only hydrophobic groups had a slow association rate due to the lack of approaching functional groups, and the association was not efficient at low telodendrimer concentrations (FIG. 5d and Table 3). The binding between proteins and the telodendrimers with only hydrophobic groups might be overestimated by BLI study due to the presence of hydrophobic interactions between uncoated sensor surfaces and the telodendrimers, since no obvious FRET was observed when the telodendrimer with only hydrophobic groups was added into the mixture of RB-BSA and FITC-BSA (significant FRET was only observed in the system containing the telodendrimers with both charged and hydrophobic groups). In a system of lipid-like nanoparticles, Xu and coworkers also observed that not only charge—charge interaction but also hydrophobic interaction contributed to the complexation between proteins and lipidoids.

Figure 21:
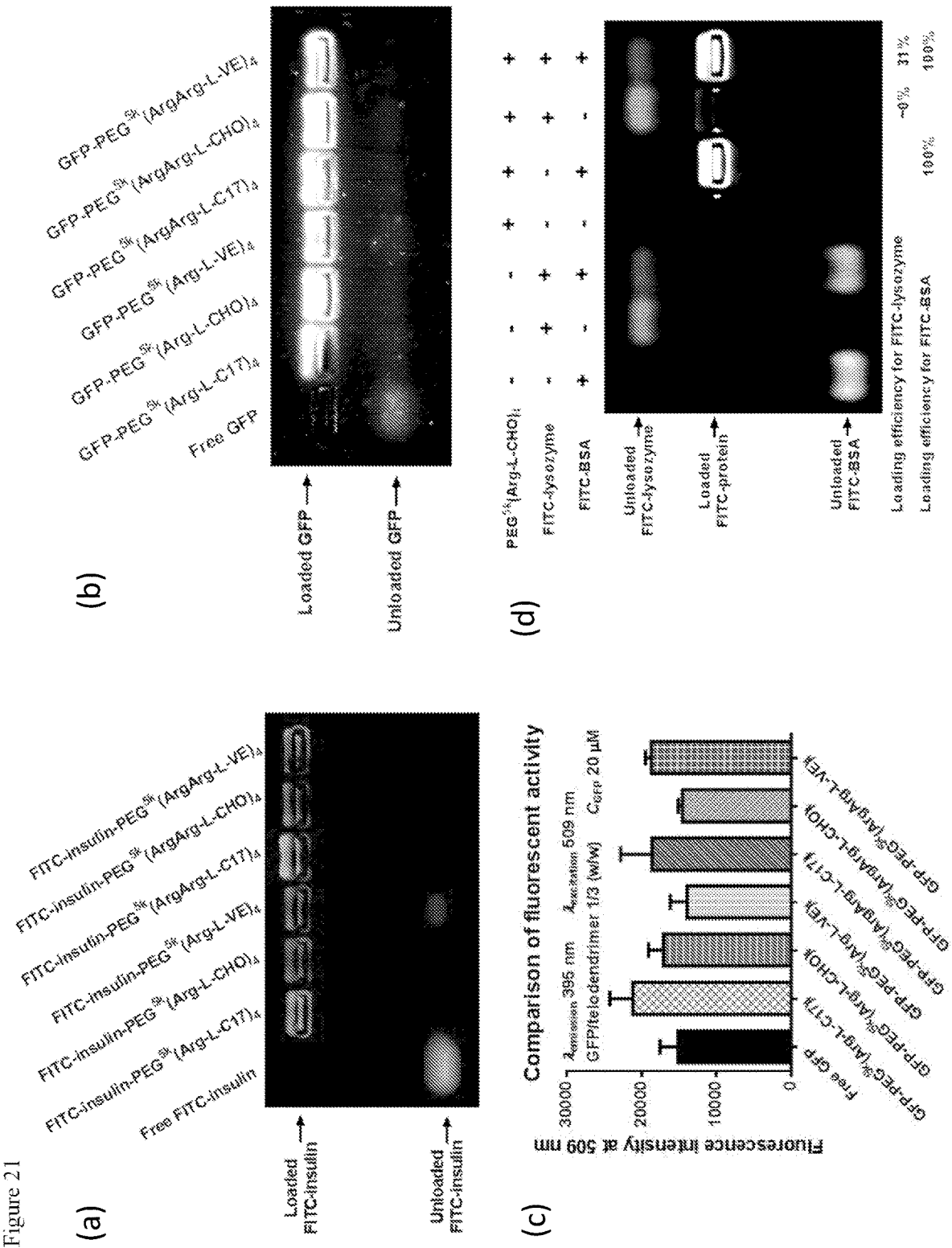
FIG. 21. Example of telodendrimer loading. (a) Loading ability of telodendrimer nanoparticles for FITC-insulin determined by an agarose gel retention assay. (b) Loading ability of telodendrimer nanoparticles for GFP determined by an agarose gel retention assay. For (a) and (b) mass ratio of protein to telodendrimer is 1/3. (c) Comparison of fluorescent activities of free GFP and GFP-telodendrimer nanoparticles in PBS (1×). (d) Loading of negatively charged FITC-BSA and positively charged FITC-lysozyme in telodendrimer nanoparticles determined by an agarose gel retention assay. The feed mass ratio of FITC-BSA to telodendrimer is 1/3, and the feed mass ratio of FITC-lysozyme to telodendrimer is also 1/3. Telodendrimer nanoparticles cannot efficiently load FITC-lysozyme. FITC-lysozyme can form complex with FITC-BSA, and the complex can be loaded in telodendrimer nanoparticles.

Other polyanionic proteins, such as insulin and green fluorescent protein (GFP), can also be effectively encapsulated in the telodendrimer nanoparticles with a high loading mass ratio of P/T=1/3 (FIGS. 21(a) and (b)). After being loaded in the telodendrimer nanoparticles, the GFP maintains its fluorescent activity (FIG. 21(c)). This correlates our "green" protein encapsulation approach without organic solvents used. However, positively charged proteins, such as lysozyme, cannot be effectively loaded in the arginine-containing telodendrimer nanoparticles (FIG. 21(d)). This indicates the charge selectivity of the telodendrimer nanoparticles for protein loading.

Figures 22, 23:
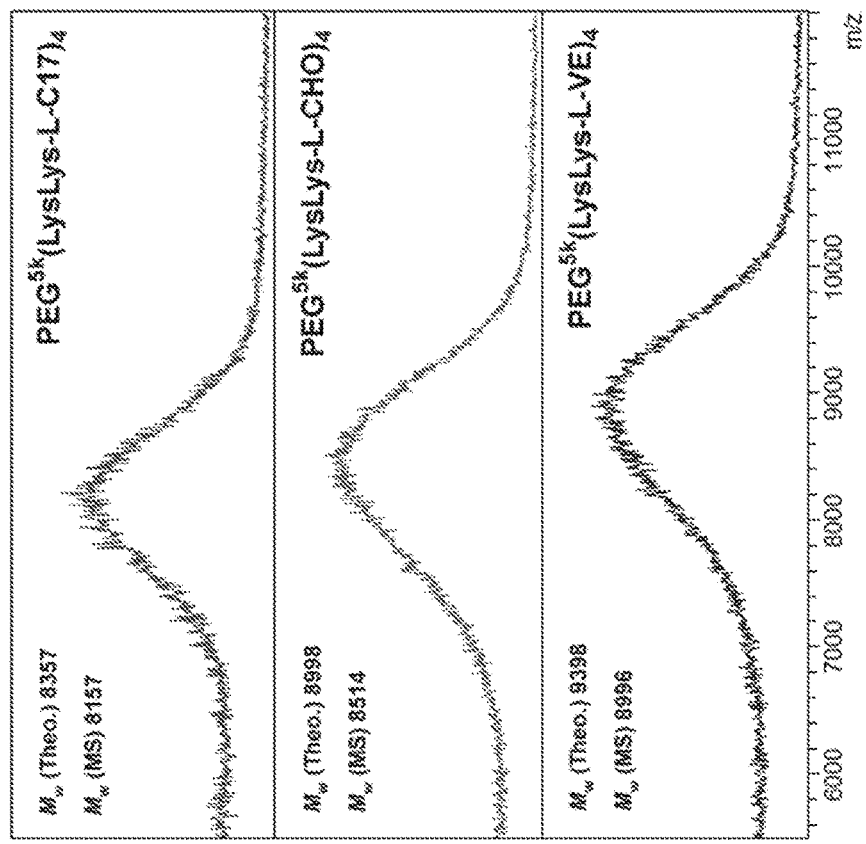
FIG. 22. Loading of positively charged FITC-lysozyme and negatively charged FITC-BSA in $PEG^{5k}(OAOA-L-R)_4$ telodendrimer nanoparticles determined by an agarose gel retention assay. The feed mass ratio of FITC-BSA to telodendrimer is 1/1, and the feed mass ratio of FITC-lysozyme to telodendrimer is also 1/1. $PEG^{5k}(OAOA-L-R)_4$ telodendrimer nanoparticles can efficiently load FITC-lysozyme. FITC-BSA-telodendrimer complexes migrated slight longer distances than that for free FITC-BSA, which may be contributed from the negative charge nature of the oxalic acid groups in $PEG^{5k}(OAOA-L-R)_4$ telodendrimers.
FIG. 23. MALDI-TOF MS of telodendrimers containing eight amino groups.

For loading of positively charged proteins, we also designed a telodendrimer architecture by simply replacing the guanidine groups in the arginine-containing telodendrimers with oxalic acid functionalities for systemic delivery of proteins. The chemical structure and the synthesis route for the telodendrimers containing eight oxalic acid groups, PEG$^{5k}$(OAOA-L-R)$_4$, are displayed in Schemes 11 and 12, respectively. The characterization of molecular properties and protein loading behaviors are displayed in FIG. 22. As shown in FIG. 22, the PEG$^{5k}$(OAOA-L-R)$_4$ telodendrimers can efficiently load a high amount of positively charged protein of lysozyme (100% of the telodendrimer by weight). However, due to the negative charge nature of the oxalic acid groups in PEG$^{5k}$(OAOA-L-R)$_4$ telodendrimers, the negatively charged protein of BSA cannot be loaded to the telodendrimer nanoparticles efficiently.

Figure 17:
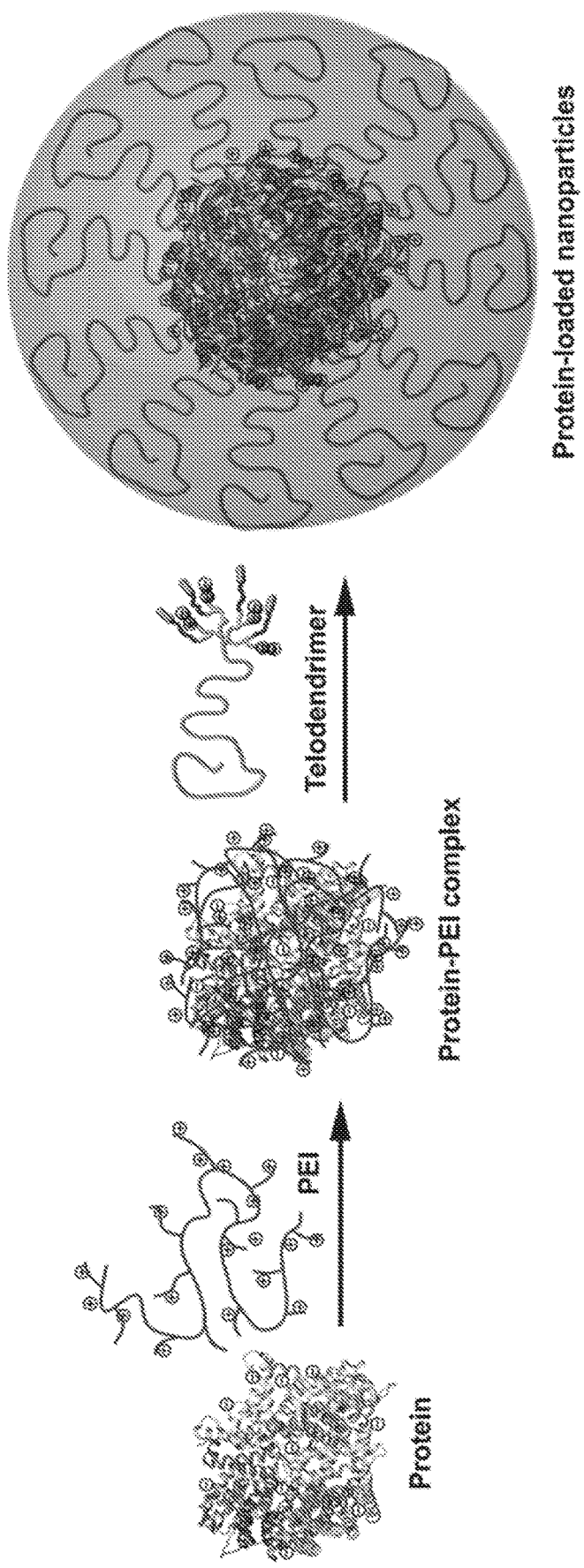
FIG. 17. The formation of protein-polycation-telodendrimer nanoparticles. The protein should be a negatively charged protein, e.g., BSA, PEI is used as a model polycation, and a telodendrimer is $PEG^{5k}(OAOA-L-R)_4$.
Figure 24:
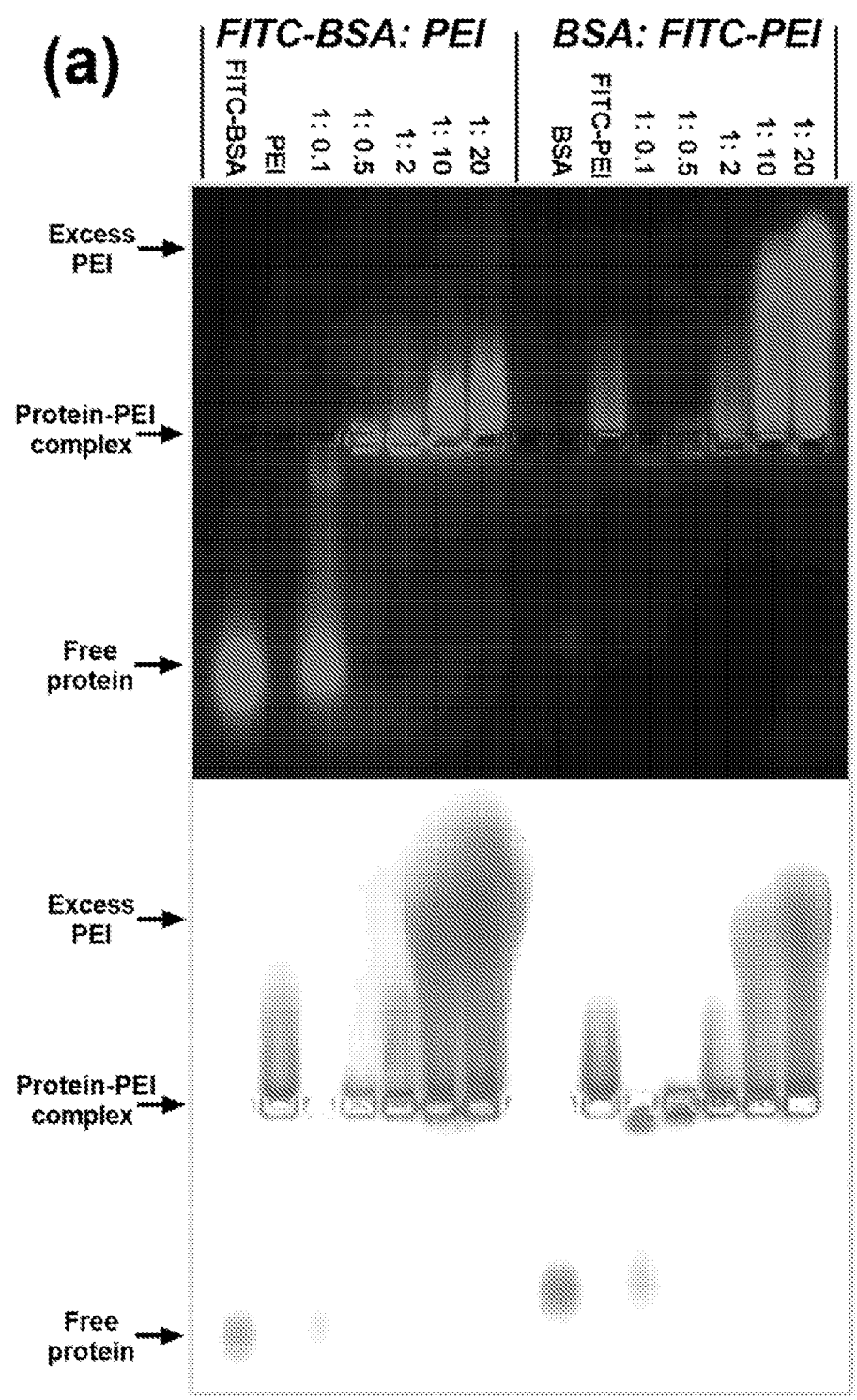
FIG. 24. Characterization of an example of a protein-polycation complex. (a) Agarose gel retention assay for FITC-BSA-PEI complex (left) and BSA-FITC-PEI complex (right) at different mass ratios of protein to polycation. (b) Hydrodymanic diameters of the BSA-PEI complexes at different mass ratios of protein to polycation in PBS (1×) at a BSA concentration of 0.2 mg/mL.
Figure 24:
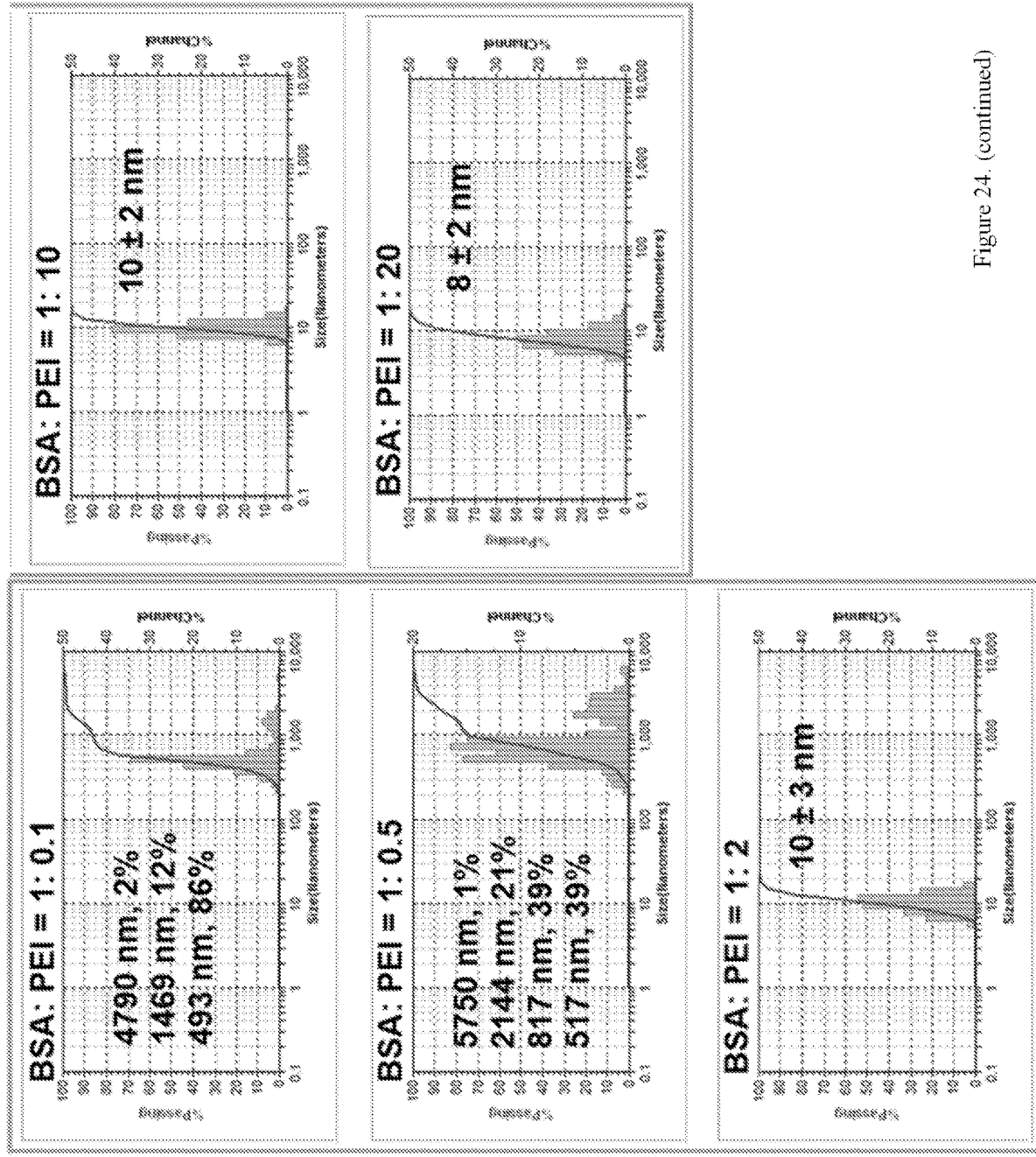
Figure 25:
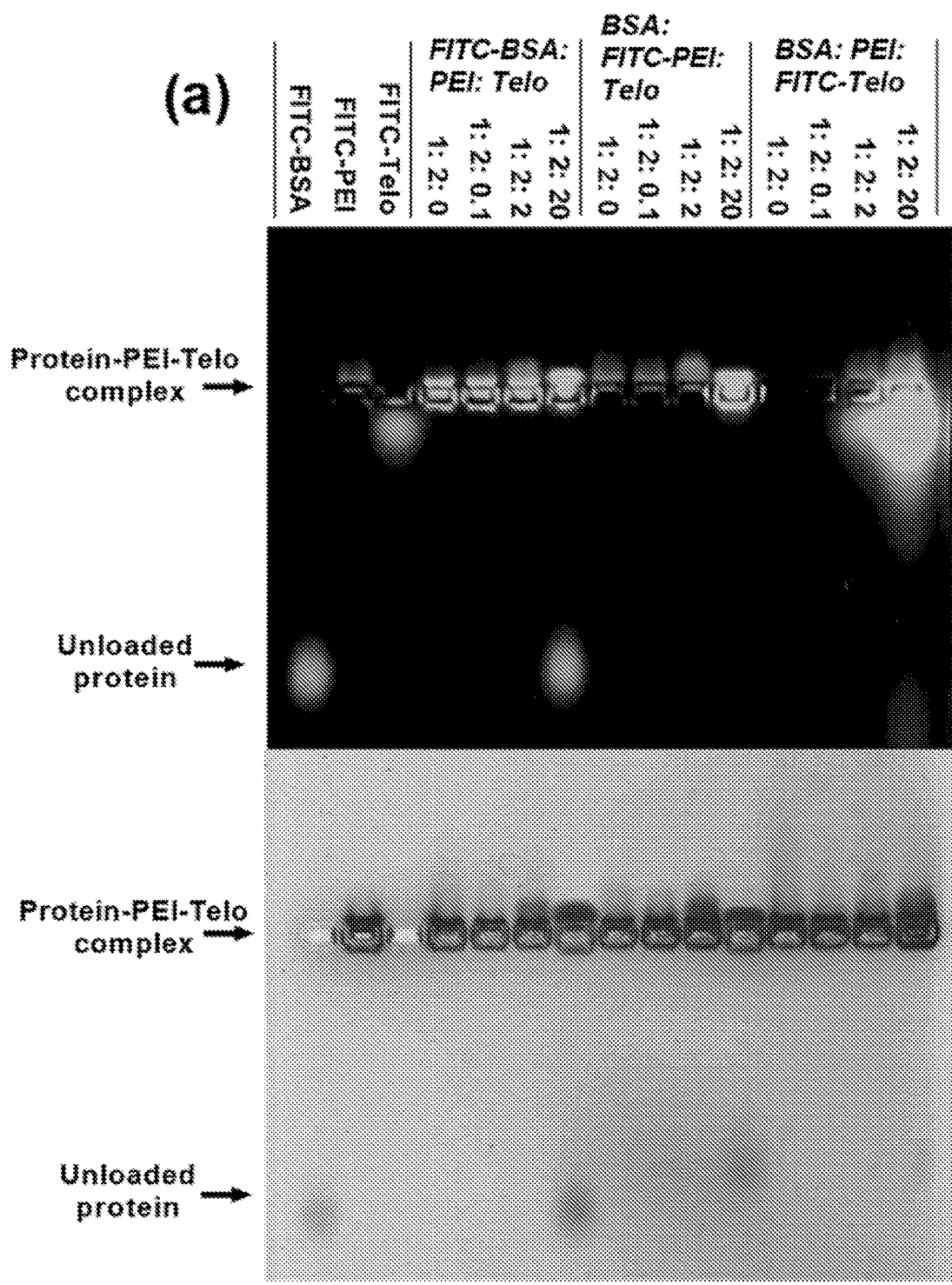
FIG. 25. Characterization of an example of protein/polycation/telodendrimer nanoparticles. (a) Agarose gel retention assay for FITC-BSA-PEI-Telo complex, BSA-FITC-PEI-Telo complex, and BSA-PEI-FITC-Telo complex at different mass ratios of protein/polycation/telodendrimer. (b,c) Hydrodymanic diameters (b) and zeta potential (c) of BSA-PEI-Telo nanoparticles at different mass ratios of protein/polycation/telodendrimer in PBS (1×) at a BSA concentration of 0.2 mg/mL. An example of a telodendrimer is $PEG^{5k}(OAOA-L-CHO)_4$.
Figure 25:
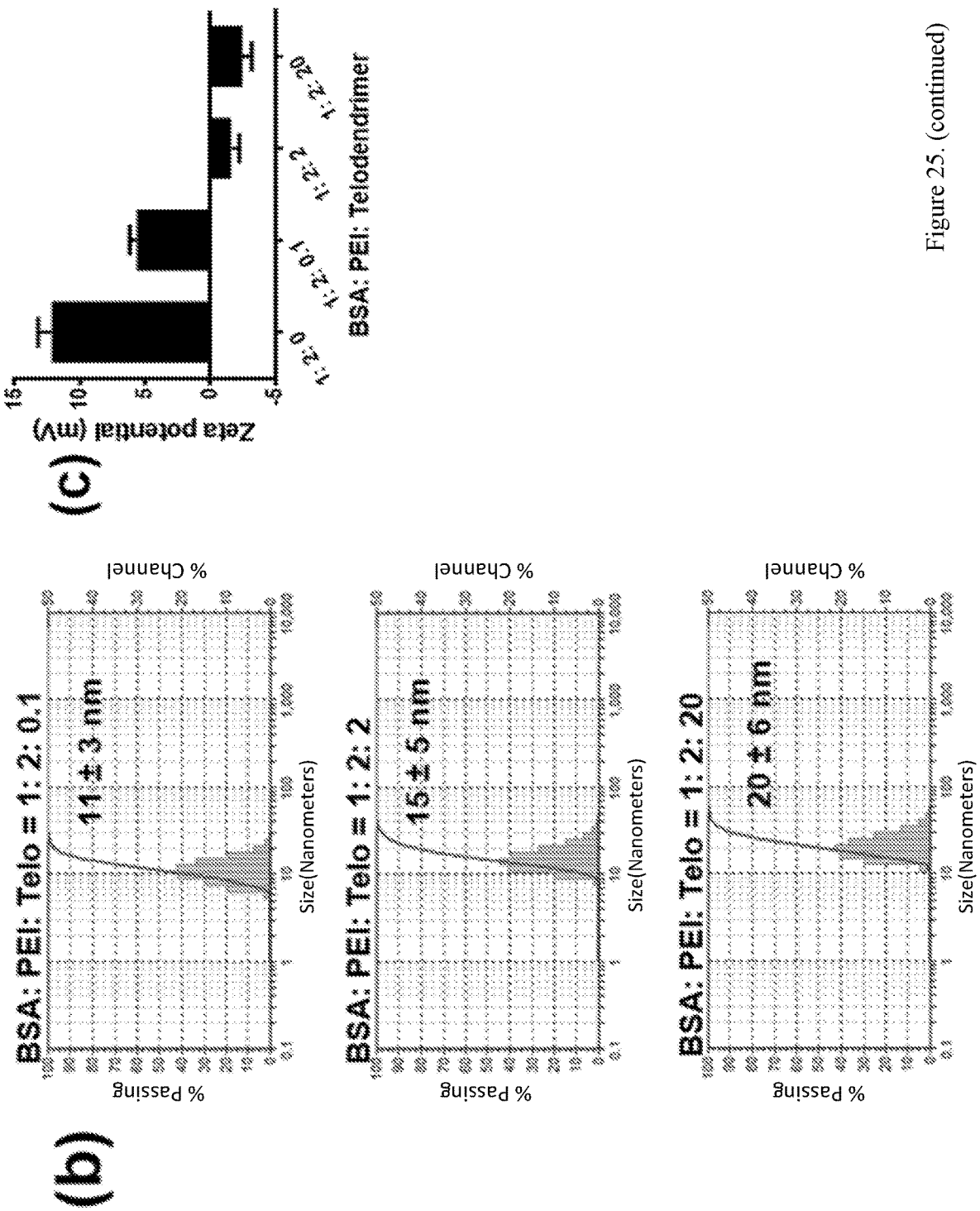

Moreover, we designed a protein-polycation-telodendrimer system for systemic/extracelluar protein delivery. As shown in FIG. 17, the negatively charged proteins, such as BSA, firstly formed complex with polycation, e.g., polyethylenimine (PEI), and PEG$^{5k}$(OAOA-L-R)$_4$ telodendrimers were used to coat the protein-polycation complex to produce protein-polycation-telodendrimer nanoparticles. BSA and PEI formed stable complex with a well-defined particle size of 10±3 nm at a protein to polycation mass ratio of 1:2 (FIG. 24). Large aggregates formed when the protein to polycation ratio larger than 1:2 while excess PEI existed in the systems at protein to polycation ratios smaller than 1:2. Therefore, the protein to polycation ratio of 1:2 is considered to be the best ratio to form protein-polycation complex, and it will be used for further studies. PEG$^{5k}$(OAOA-L-CHO)$_4$ telodendrimers were then used to coat the protein-polycation complex to reduce the surface charge potential, which also had promise to reduce cytotoxicity of the polycation, and to avoid nonspecific phagocytosis by the reticuloendothelium systems in vivo. As shown in FIG. 25, the BSA-PEI-PEG$^{5k}$(OAOA-L-CHO)$_4$ nanoparticles at a protein/polycation/telodendrimer mass ratio of 1:2:2 showed stable protein loading behaviors, a well-defined particle size of 15±5 nm, and neutral zeta potential. Increasing the telodendrimer amount in the system resulted in a leakage of loaded BSA, while zeta potential of the nanoparticles obviously increased when a reduced amount of telodendrimer was used. These facts indicate the protein/polycation/telodendrimer ratio of 1:2:2 is the best ratio to form protein-polycation-telodendrimer nanoparticles. We herein realize the encapsulation of negatively charged protein by PEG$^{5k}$(OAOA-L-R)$_4$ telodendrimer with the help of polycation.

Figure 19:
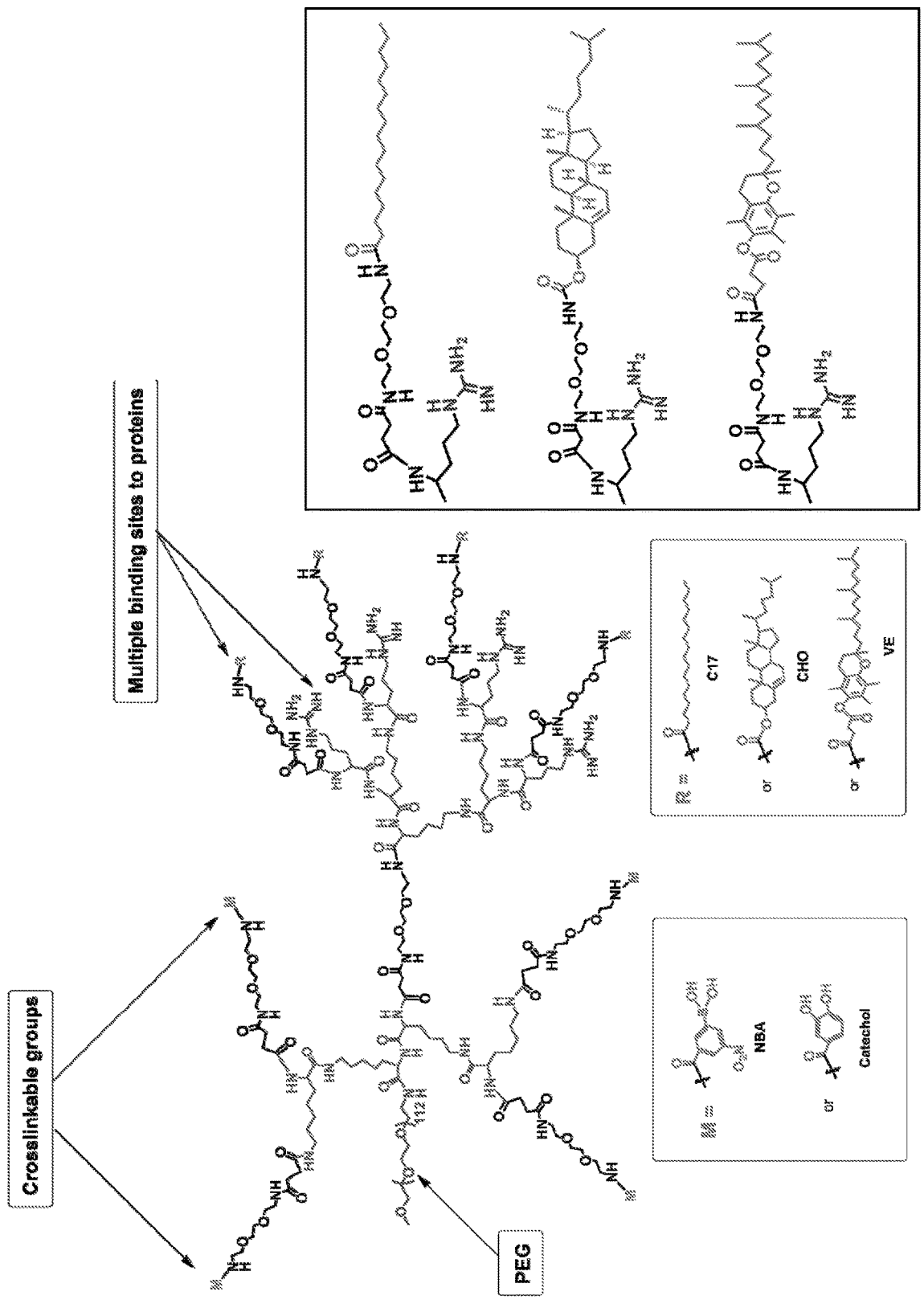
FIG. 19. Chemical structure of crosslinkable telodendrimers.

Other functional groups, such as the crosslinkable boronic acid/catechol pair, can also be introduced into the telodendrimer system, and the resulting telodendrimer (its chemical structure is shown in FIG. 19) is expected to serve as a smart and robust coating for the delivery of insulin or human growth hormone with the ability to release the cargo proteins in response to mannitol and/or acidic pH values.

Figure 6:
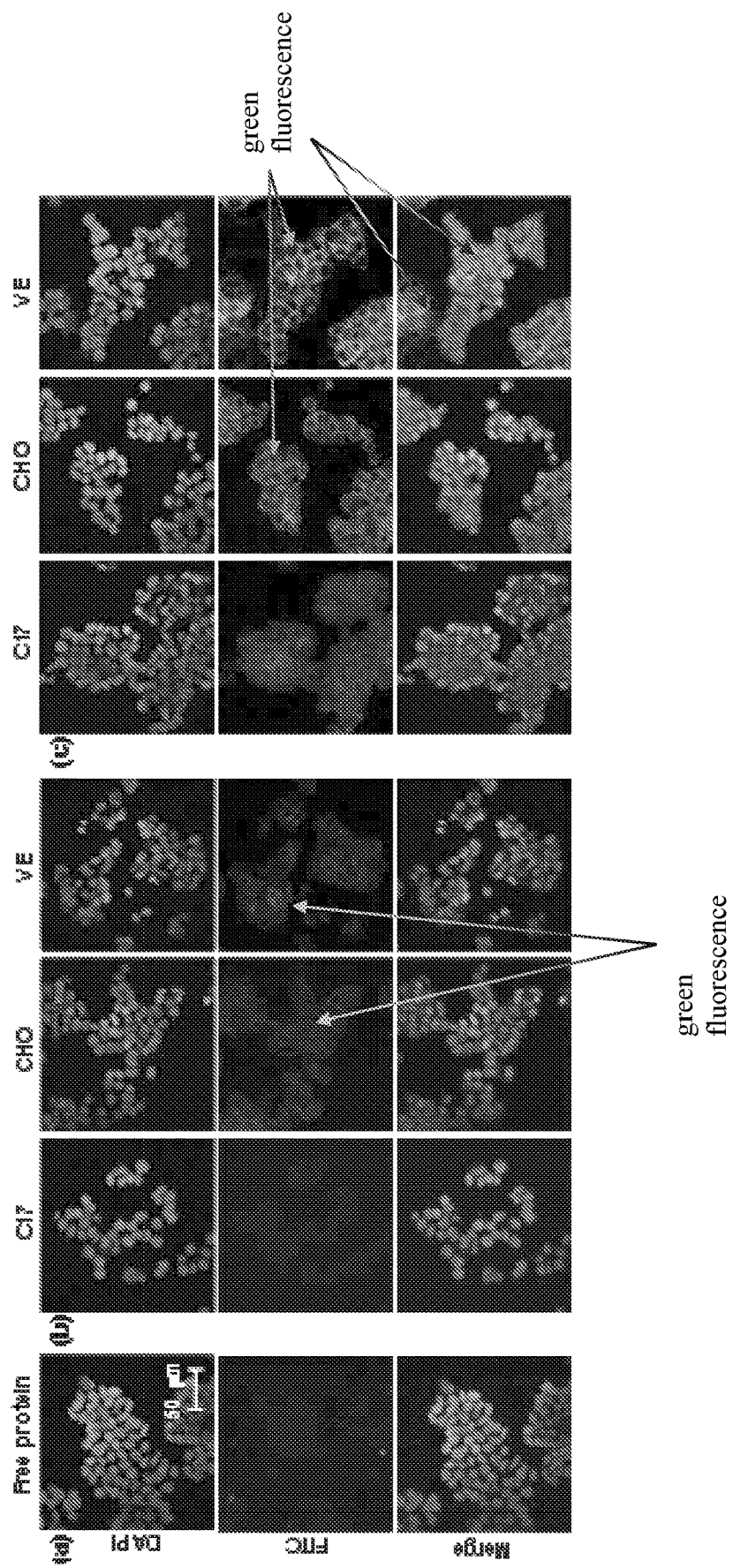
FIG. 6. CLSM images of HT-29 cells incubated at 37° C. for 3 h with free FITC-BSA (a), and FITC-BSA loaded in the nanoparticles of telodendrimers containing four (b) or eight (c) guanidine groups, and C17, CHO or VE as hydrophobic groups at a P/T ratio of 1/3 by weight. The images were taken at a magnification of 60×. The cell nuclei were stained with DAPI (blue).

Cellular Uptake of Protein-Loaded Telodendrimer Nanoparticles. Green fluorescent FITC-BSA molecules were used to probe the intracellular trafficking of proteins without and with telodendrimer nanoparticles. HT-29 colon cancer cells were incubated with free FITC-BSA and FITC-BSA-loaded telodendrimer nanoparticles, and were imaged by confocal laser scanning microscopy (CLSM). As shown in FIG. 6a, free FITC-BSA without telodendrimer nanoparticles could hardly enter the cells spontaneously. Only a small amount of the FITC-BSA molecules loaded in the nanoparticles of the telodendrimers containing four guanidine groups at a P/T ratio of 1/3 by weight could be delivered to the cellular interiors (green fluorescence in FIG. 6b). This result is consistent with other studies that arginine-containing platforms with less than six guanidine groups cannot translocate through cell membranes efficiently. The poor intracellular protein delivery efficiency of the telodendrimers containing four guanidine groups may restrict their applications for intracellular delivery, however, this endows them with the potential to serve as nanocarriers for systemic delivery of proteins such as insulin. In contrast, significant cellular uptake and intracellular accumulation of the FITC-BSA molecules, that were loaded in the nanoparticles of the telodendrimers containing eight guanidine groups at a P/T ratio of 1/3 by weight, were observed in the cytoplasm of HT-29 cancer cells (green fluorescence in FIG. 6c), indicating the ability of eight guanidine-containing telodendrimer nanoparticles for efficient membrane transport of proteins. We also found the species of the hydrophobic moieties in the telodendrimers affected their protein delivery efficiency: the delivery efficiency for CHO— or VE-containing telodendrimers was higher than that for C17-containing telodendrimers mainly because CHO and VE were more likely to inset into cell membrane that contributed to cellular uptake (FIGS. 6b and 6c). The cellular uptake behavior of protein-loaded telodendrimer nanoparticles in the glioblastoma multiforme (GBM) cell line of U87 was also investigated, which displayed a similar trend with that in HT-29 cells.

Figure 16:
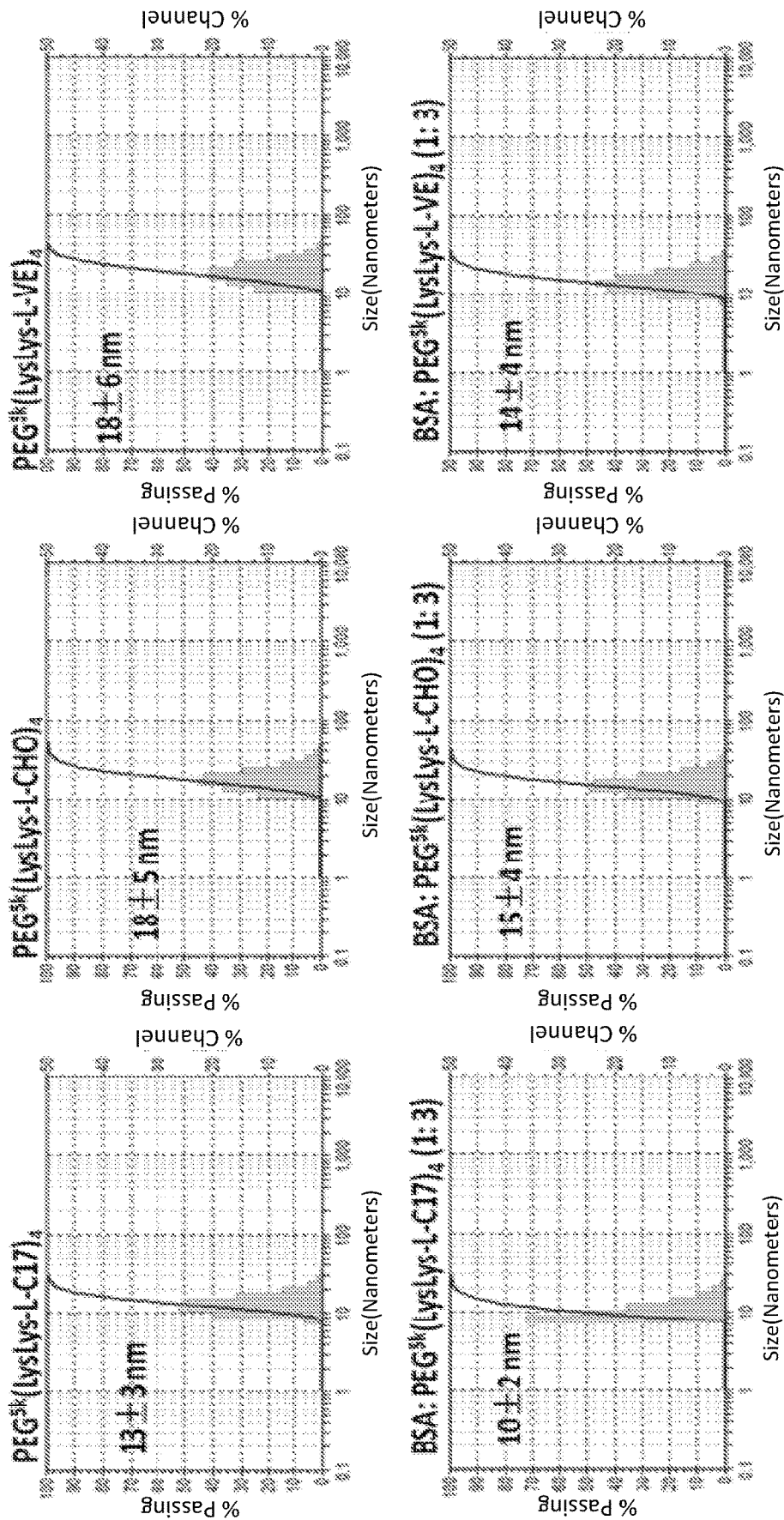
FIG. 16. Hydrodynamic diameters of telodendrimers containing eight amino groups before (upper row) and after (lower row) loading of BSA at a loading ratio of BSA to telodendrimer of 1/3 by weight in PBS (1×) at a telodendrimer concentration of 1 mg/mL.
Figure 20:
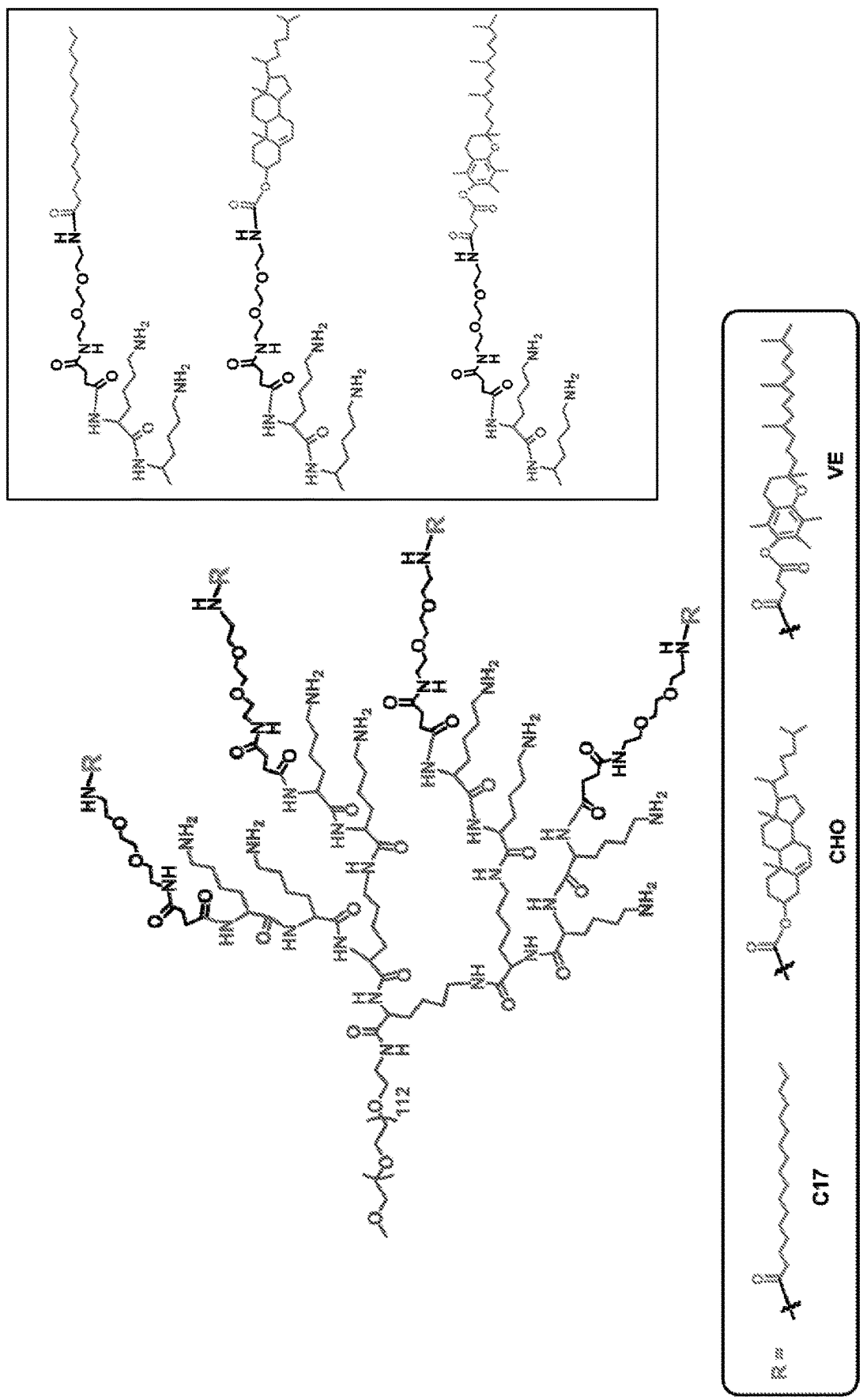
FIG. 20. Chemical structure of the telodendrimers containing eight amino groups, named as $PEG^{5k}(LysLys-L-R)_4$.
Figure 27:
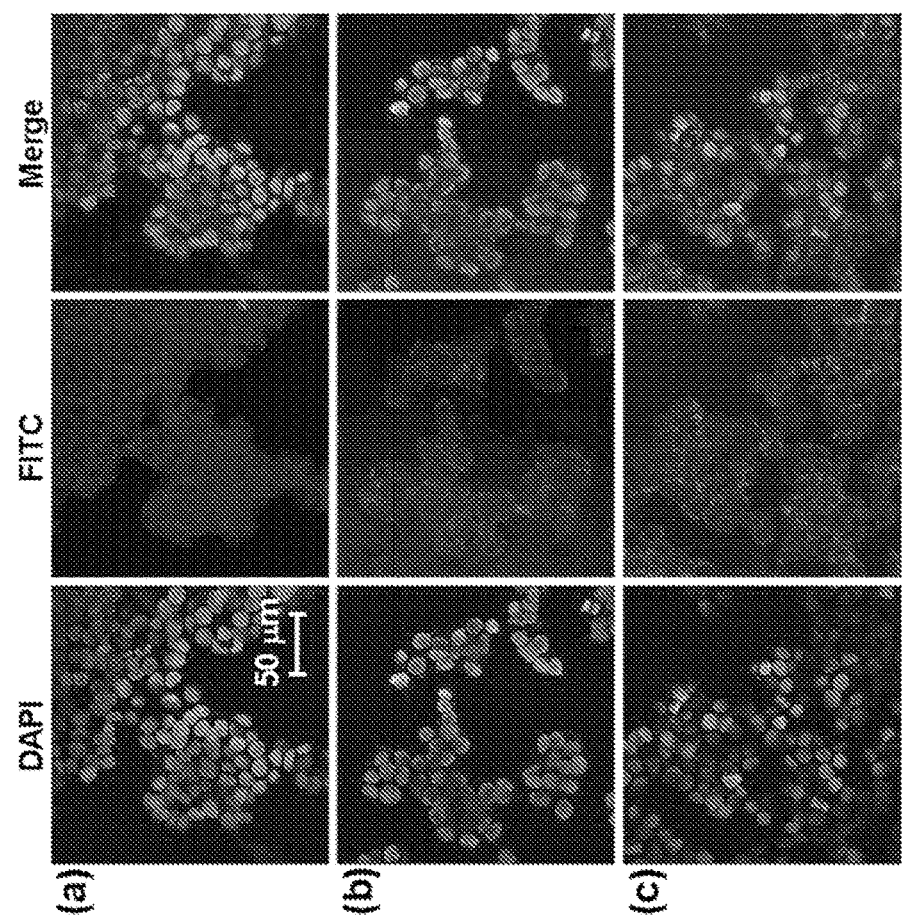
FIG. 27. Cell uptake of FITC-BSA loaded in the nanoparticles made from telodendrimers with eight amino groups. CLSM images of HT-29 cells incubated at 37° C. for 3 h with FITC-BSA-loaded nanoparticles of $PEG^{5k}(LysLys-L-C17)_4$ (a), $PEG^{5k}(LysLys-L-CHO)_4$ (b), and $PEG^{5k}(LysLys-L-VE)_4$ (c) at a P/T ratio of 1/3. The images were taken at a magnification of 60×. The cell nuclei were stained with DAPI (blue).
Figure 26:
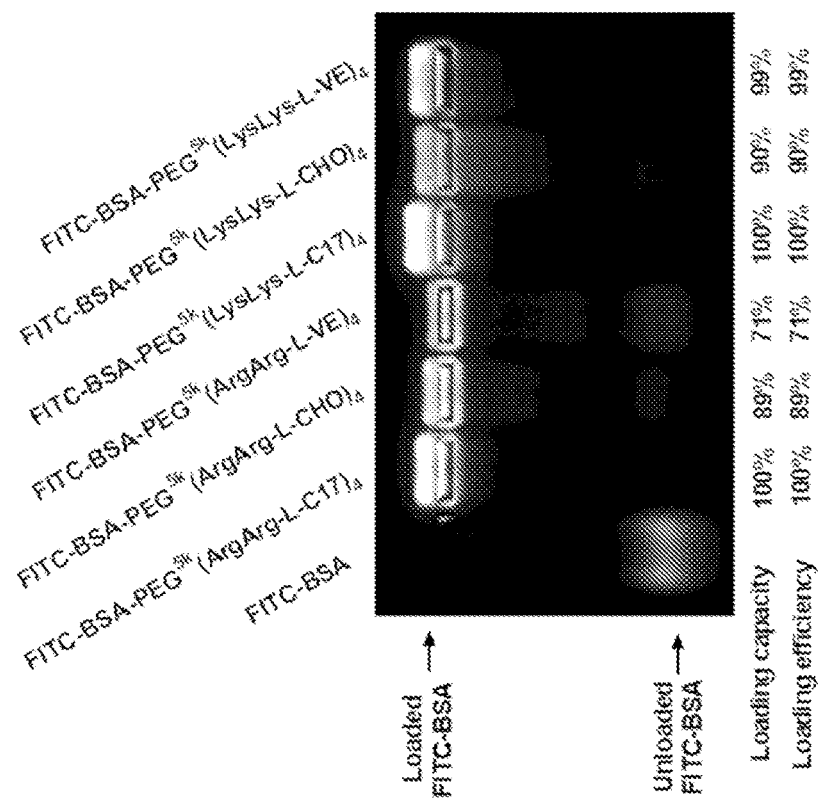
FIG. 26. Loading capacity and loading efficiency of telodendrimers for FITC-BSA determined by an agarose gel retention assay. The feed mass ratio of protein to telodendrimer is 1/1.

The guanidine group is the strongest organic base to form ionic bridges in protein, also it can form cation-pi interactions. Polyarginine is able to induce efficient membrane transport due to its interaction with the phosphate or other anionic moieties on cell surfaces. The guanidine functionality in the telodendrimers is expected to offer enhanced membrane transport of proteins. To confirm importance of the guanidine functionality, the arginines with guanidine groups in the telodendrimers were replaced by lysines with amino groups. The chemical structures of the telodendrimers containing amino groups are shown in FIG. 20, and their characterizations are displayed in FIGS. 23 and 16. The telodendrimers containing amino groups have comparable protein loading capacities with the telodendrimers containing guanidine groups (FIG. 26). However, the telodendrimers containing eight amino groups can deliver significantly less proteins to cellular interiors when compared to the telodendrimers containing eight guanidine groups (FIG. 27). This affirms the necessity to introduce guanidine functionality to the telodendrimers for efficient intracellular delivery of proteins.

Figure 28:
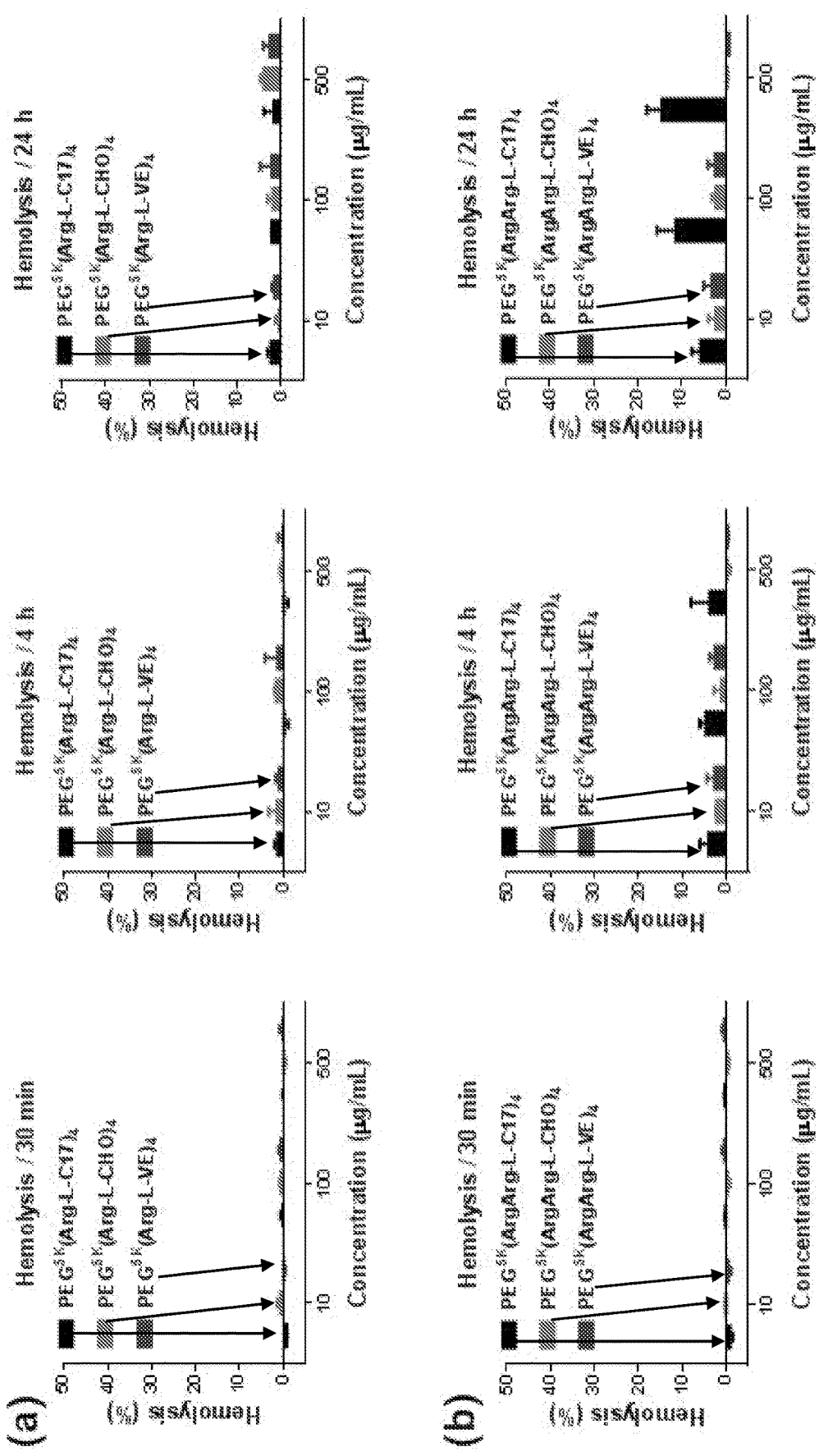
FIG. 28. Hemolytic property of telodendrimers containing four (a) or eight (b) guanidine groups at different time points after the diluted RBC suspension was mixed with telodendrimers.

Hemolysis and Cytotoxicity. The investigation on hemolytic activity is important to measure the safety of nanomaterials used for therapeutic delivery. Our telodendrimer nanoparticles are generally inert in the hemolytic assay (FIG. 28), which indicates safe use for systemic administration. Only PEG$^{5k}$(ArgArg-L-C17)$_4$ shows a slight hemolytic activity after a long incubation time of 24 h at high telodendrimer concentrations.

Figure 7:
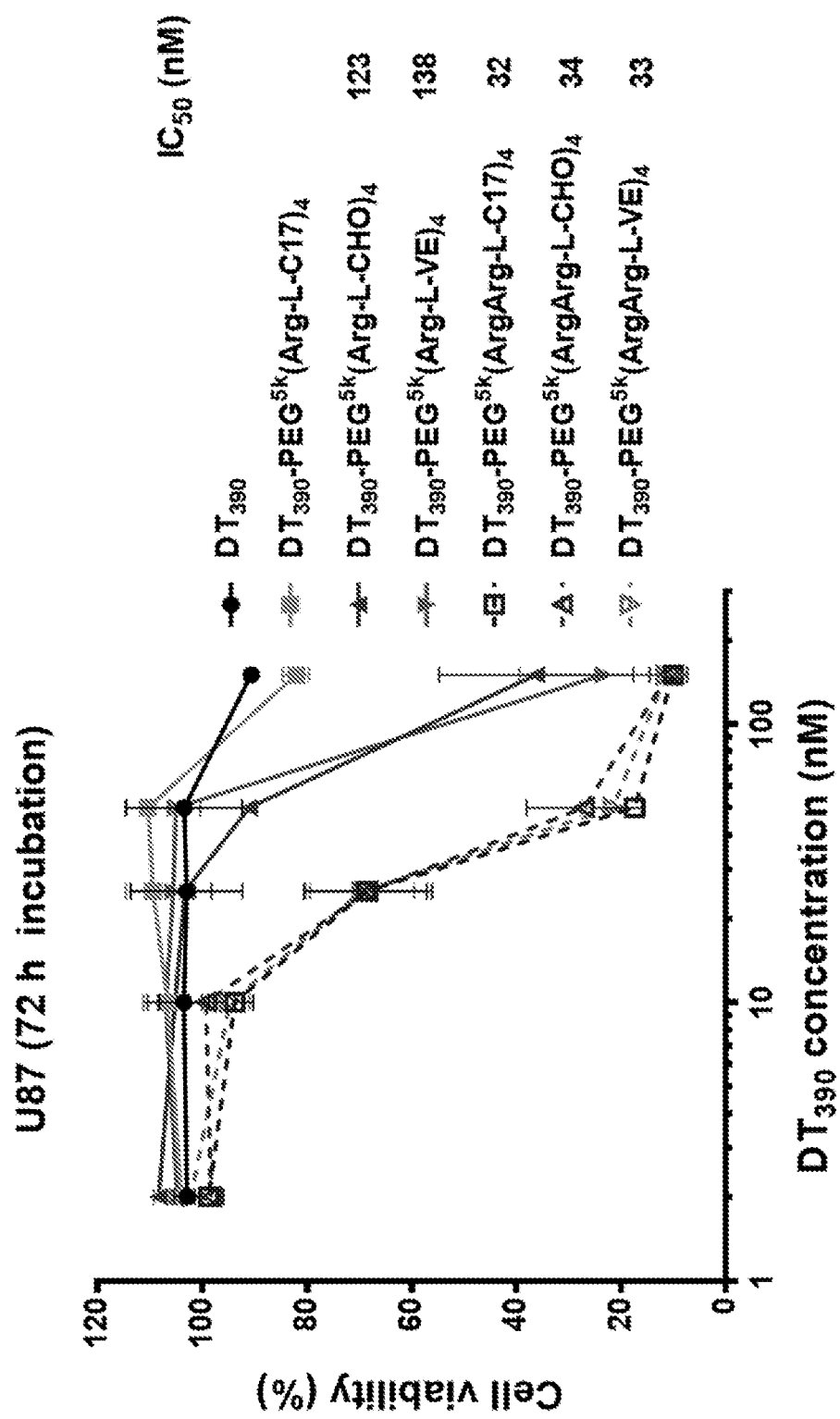
FIG. 7. Cell viability assay on U87 cells after a 72 h continuous incubation at 37° C. for free $DT_{390}$, and $DT_{390}$-loaded telodendrimer nanoparticles.

Therapeutic proteins cause cellular cytotoxicity by different pathways after internalization with a potent antitumor effect. However, the unsatisfied cell-penetration abilities of most proteins may limit their clinical application. Our telodendrimer nanoparticles are able to effectively deliver proteins across tumor cell membranes, resulting in desire tumor cell apoptosis. Truncated diphtheria toxin (DT$_{390}$), that induces cell death by inhibiting protein synthesis after entering into the cell cytoplasm, was used as a model therapeutic protein to investigate the intracellular delivery ability of the telodendrimer nanoparticles. The GBM cell line of U87 was exposed to free $DT_{390}$ and $DT_{390}$-loaded telodendrimer nanoparticles for apoptotic analysis. As shown in FIG. 7, free $DT_{390}$ show nontoxic against U87 cells all through the concentrations tested. This is because $DT_{390}$ is unable to enter into the cell interiors spontaneously. The $DT_{390}$ loaded in the telodendrimer nanoparticles containing four guanidine groups (1/3 of P/T by weight) exhibits obvious cytotoxicity only at a high protein concentration of 150 nM due to the inefficient cell-penetration. $DT_{390}$ loaded in $PEG^{5k}(Arg-L-CHO)_4$ and $PEG^{5k}(Arg-L-VE)_4$ exhibits higher toxicities than C17-containing formulation, which was correlated with the cell uptake results (FIG. 7). The bioactive $DT_{390}$ loaded in the telodendrimer nanoparticles containing eight guanidine groups (1/3 of P/T by weight) can be potently delivered into the cytoplasm of U87 cells resulting in a protein-concentration-dependent killing of these cells, and the half-maximal growth inhibitory concentration ($IC_{50}$) values are 32, 34, and 33 nM for $DT_{390}$-loaded $PEG^{5k}(ArgArg-L-C17)_4$, $PEG^{5k}(ArgArg-L-CHO)_4$, and $PEG^{5k}(ArgArg-L-VE)_4$ nanoparticles, respectively. The telodendrimer concentration range used for $DT_{390}$ delivery study is 0.3-18.6 μg/mL, and no nanoparticle-related cytotoxicity is exhibited in this concentration range for both U87 and HT-29 cell lines. A DTEGF fusion toxin consisting of a truncated diphtheria toxin, a seven-amino-acid linker, and a human epidermal growth factor that can target to U87 cells, was also able to be loaded in the telodendrimer nanoparticles, as determined by an agarose gel retention assay. The DTEGF fusion toxins loaded in the telodendrimer nanoparticles had similar $IC_{50}$ values with that for free DTEGF on U87 cells, suggesting that protein bioactivity can be completely maintained in the arginine-containing telodendrimer nanoformulations.

Our design of telodendrimers with both charged and hydrophobic moieties is critical for stable and engineerable protein encapsulation and intracellular delivery. On the one hand, sufficient amounts of charged guanidine groups in the telodendrimers serve an approaching function that not only contributes to the rapid/stable protein encapsulation but also enables efficient membrane transport of proteins. On the other hand, the hydrophobic groups in the telodendrimers serve an annealing function to stabilize the loaded proteins in the telodendrimer nanoparticles and various telodendrimers can be produced using diverse hydrophobic functional molecules according to different requirements, i.e., C17 molecules are able to endow the telodendrimer nanoparticles with high protein loading capacity and binding affinity, and CHO— or VE-containing telodendrimers possess satisfied intracellular protein delivery efficiency. The hydrophobic natural compounds that can be used for telodendrimer construction are not limited to these three molecules reported in this study. The present telodendrimer architecture is an interesting model to investigate the protein-polymer complexation process in detail. We are currently attempting to integrate this telodendrimer architecture with optimal building blocks selected by virtual screening of a library of small molecules based on a protein structure for protein-specific nanocarrier design.

The facile strategy presented in this study to create telodendrimer nanocarriers with multivalent hybrid functionalities is versatile, biologically benign, and relatively inexpensive. We believe that our telodendrimer design principle provides useful information to guide the bottom-up rational fabrication of nanocarriers and promote the development in encapsulation and delivery of protein therapeutics.

Materials. Monomethylterminated poly(ethylene glycol) monoamine hydrochloride (MeO-PEG-$NH_2$.HCl, $M_W$: 5 kDa) was purchased from Jenkem Technology. (Fmoc)Lys (Fmoc)-OH and Fmoc-Arg(Pbf)-OH were obtained from AnaSpec Inc. Cholesteryl chlorofomate was purchased from Alfa Aesar. CellTiter 96® AQueous MTS reagent powder was purchased from Promega. Heptadecanoic acid was purchased from Acros. Lysozyme ($M_w$ 14.3 kDa, isoelectric point 11.0) was purchased from MP Biomedicals, LLC. Cy5NS succinimidyl ester was purchased from AAT Bioquest, Inc. Diisopropyl carbodimide (DIC), N-hydroxybenzotriazole (HOBt), D-α-tocopherol succinate, trifluoroacetic acid (TFA), fluorescein isothiocyanate isomer I (FITC), bovine serum albumin (BSA, $M_w$ 66.5 kDa, isoelectric point 5.4), acetic anhydride (AA), N-hydroxysuccinimide (HOSu), Rhodamine B (RB), and other chemical reagents were purchased from Sigma-Aldrich. Dialysis membrane with 3,500 $M_W$ cut off was purchased from Spectrum Laboratories, Inc. Bovine insulin ($M_w$ 5.8 kDa, isoelectric point 5.7) was purchased from Gemini Bio-Products. Recombinant green fluorescent protein (GFP, $M_w$ 28.2 kDa, isoelectric point 6.0) was provided by Prof. Stewart N. Loh of Department of Biochemistry and Molecular Biology at State University of New York Upstate Medical University. Truncated diphtheria toxin ($DT_{390}$, $M_w$ 42.3 kDa, isoelectric point 5.1) and DTEGF (a construct consisting of a truncated diphtheria toxin, a seven-amino-acid linker, and a human epidermal growth factor, $M_w$ 49.2 kDa, isoelectric point 4.9) were offered by Dr. Walter A. Hall of Department of Neurosurgery at State University of New York Upstate Medical University. The sequences of $DT_{390}$ and DTEGF are listed as follows:

```
DT390 Sequence:
Black = truncated diphtheria toxin (black = >) GADDVVDSSKSFVMENFSSYHGTKPGYVDSIQKGIQKPK

SGTQGNYDDDWKGFYSTDNKYDAAGYSVDNENPLSGKAGGVVKVTYPGLT

NVLALKVDNAETIKKELGLSLTEPLMEQVGTEEFIKREGDGASRVVLSLP

FAEGSSSVEYINNWEQAKALSVELEINFETRGKRGQDAMYEYMAQACAGN

RVRRSVGSSLSCINLDWDVIRDKTKTKIESLKEHGPIKNKMSESPNKTVS

EEKAKQYLEEFHQTALEHPELSELKTVTGTNPVFAGANYAAWAVNVAQVI

DSETADNLEKTTAALSILPGIGSVMGIADGAVHHNTEEIVAQSIALSSLM

VAQAIPLVGELVDIGFAAYNFVESIINLFQVVHNSYNRPAYSPGHKTQPF

DTEGF Sequence:
Black = truncated diphtheria toxin

Green = linker

Purple = human epidermal growth factor (black = >) GADDVVDSSKSFVMENFSSYHGTKPGYVDSIQKGIQKPK

SGTQGNYDDDWKGFYSTDNKYDAAGYSVDNENPLSGKAGGVVKVTYPGLT

NVLALKVDNAETIKKELGLSLTEPLMEQVGTEEFIKREGDGASRVVLSLP

FAEGSSSVEYINNWEQAKALSVELEINFETRGKRGQDAMYEYMAQACAGN

RVRRSVGSSLSCINLDWDVIRDKTKTKIESLKEHGPIKNKMSESPNKTVS
```

-continued

EEKAKQYLEEFHQTALEHPELSELKTVTGTNPVFAGANYAAWAVNVAQVI

DSETADNLEKTTAALSILPGIGSVMGIADGAVHHNTEEIVAQSIALSSLM

VAQAIPLVGELVDIGFAAYNEVESIINLFQVVHNSYNRPAYSPGHKTQPF (green = >) *EASGGPE* (purple = >) NSDSECPLSHDGYCLHDGVC

MYIEALDKYACNCVVGYIGERCQYRDLKWWELR

Figure 8:
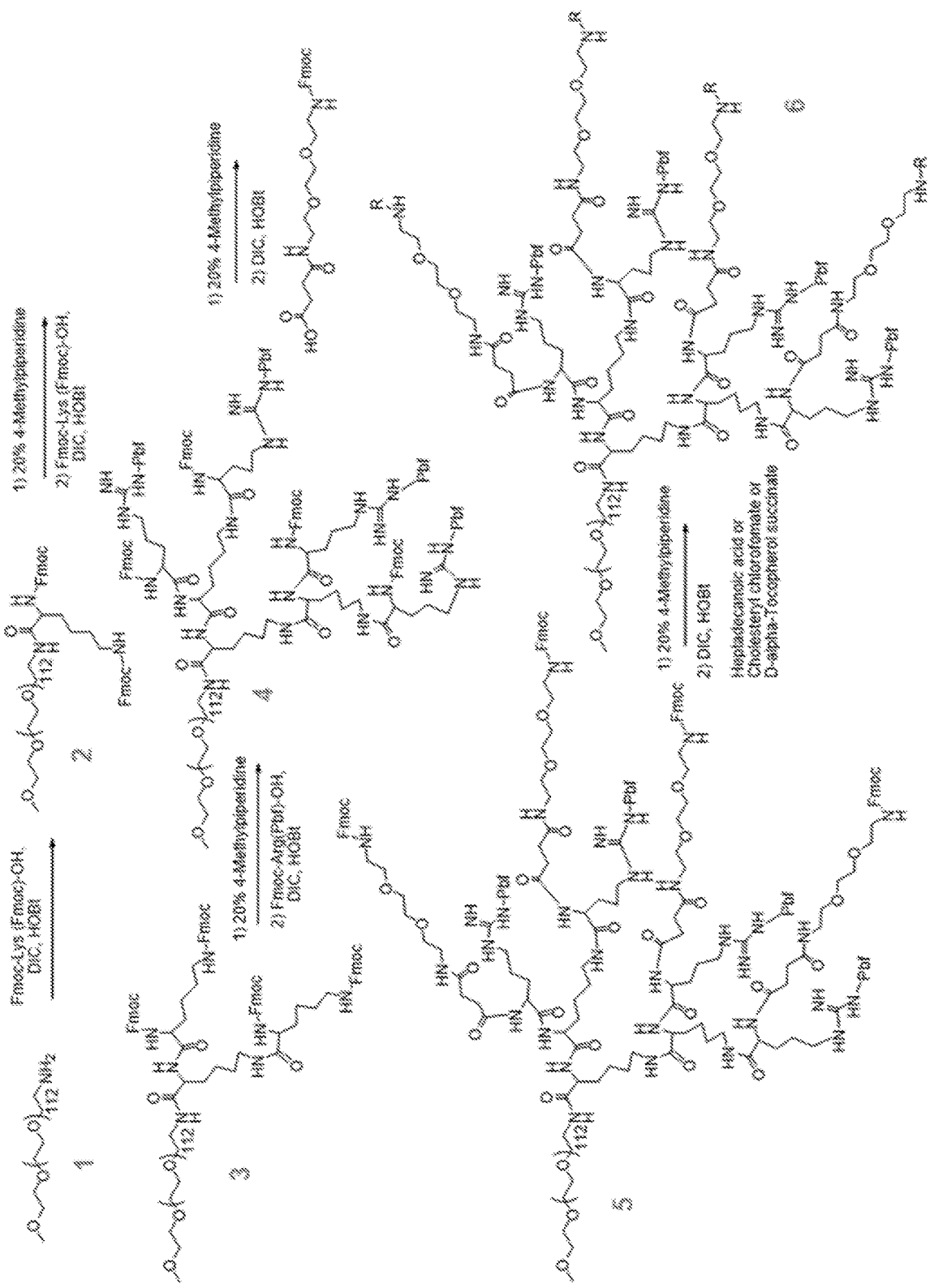
FIG. 8. Synthetic route for telodendrimers with four guanidine groups.
Figure 8:
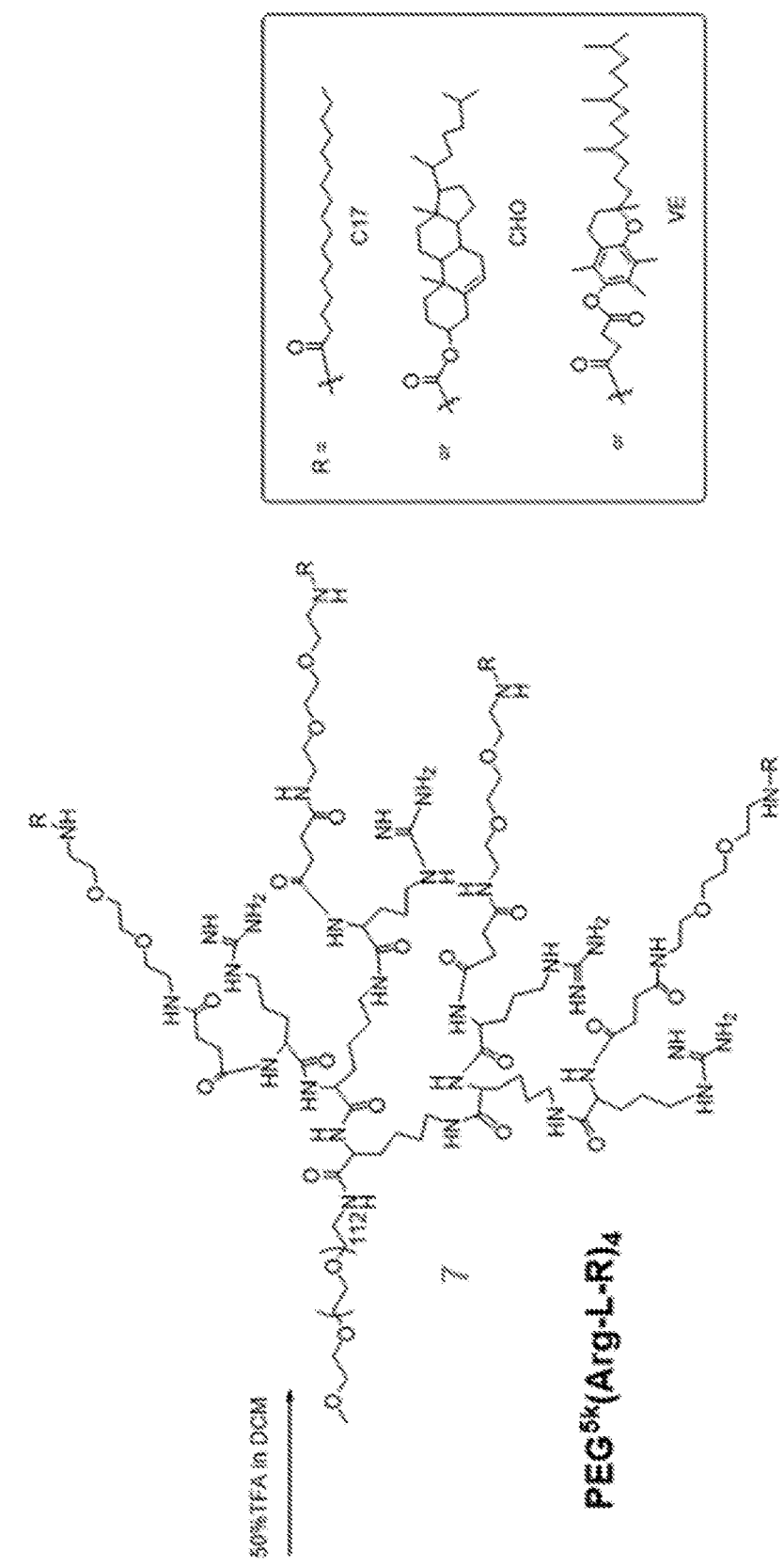
Figure 9:
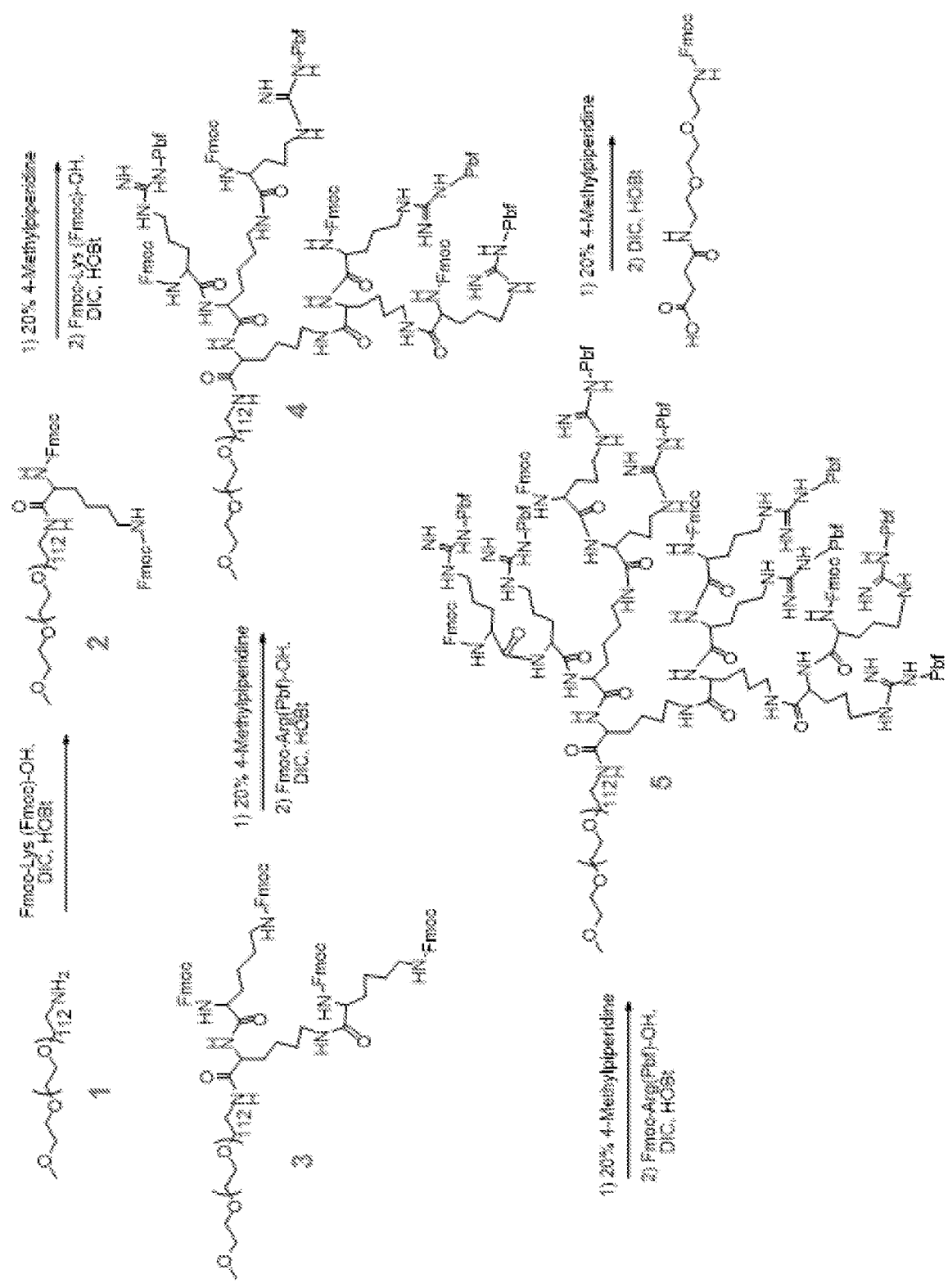
FIG. 9. Synthetic route for telodendrimers with eight guanidine groups.
Figure 9:
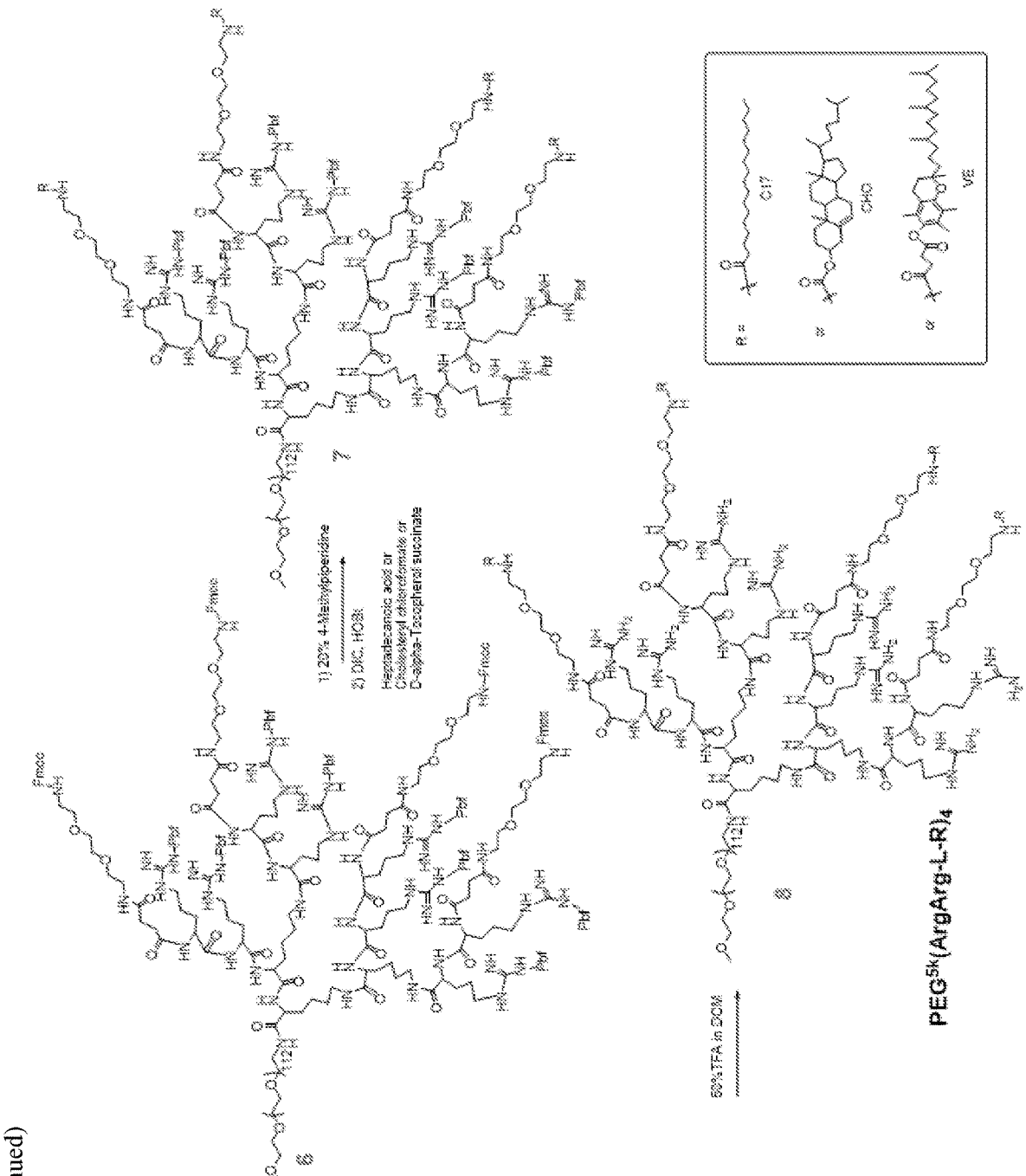

Telodendrimer Synthesis. The telodendrimers with four guanidine groups containing heptadecanoic acids, cholesterols and D-α-tocopherol succinates, which are named as PEG$^{5k}$(Arg-L-C17)$_4$, PEG$^{5k}$(Arg-L-CHO)$_4$ and PEG$^{5k}$(Arg-L-VE)$_4$, respectively, were synthesized using a solution-phase condensation reaction starting from MeO-PEG-NH$_2$.HCl (5 kDa) via stepwise peptide chemistry. The procedure was performed as follows: (Fmoc)Lys(Fmoc)-OH (3 eq.) reacted with the N terminus of PEG using DIC and HOBt as coupling reagents until a negative Kaiser test result was obtained, indicating completion of the coupling reaction. PEGylated molecules were precipitated through the addition of the cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum. One coupling of (Fmoc)Lys(Fmoc)-OH and one coupling of Fmoc-Arg(Pbf)-OH were carried out respectively upon the removal of Fmoc groups to generate an intermediate of dendritic poly(amino acid) terminated with four Pbf groups and four Fmoc groups on one end of PEG. Then four PEG linker molecules (M$_w$: 470) were coupled to the amino groups upon the removal of Fmoc groups with 20% (v/v) 4-methylpiperidine in DMF. After the removal of Fmoc groups, the polymers were coupled with heptadecanoic acid, cholesteryl chlorofomate, or D-α-tocopherol succinate. The Pbf protecting groups were consecutively removed via the treatment with 50% TFA in dichloromethane (DCM) to yield PEG$^{5k}$(Arg-L-C17)$_4$, PEG$^{5k}$(Arg-L-CHO)$_4$ and PEG$^{5k}$(Arg-L-VE)$_4$ (FIG. 8). Positive Kaiser test results were obtained for these arginine-containing telodendrimers, indicating the successful removal of Pbf protecting groups from the guanidine groups. These resulting telodendrimers were dissolved in deionized water, dialyzed against deionized water for 2 days, and then dried by lyophilization. The synthesis procedure of the telodendrimers with eight guanidine groups containing heptadecanoic acids, cholesterols and D-α-tocopherol succinates, which are noted as PEG$^{5k}$(ArgArg-L-C17)$_4$, PEG$^{5k}$(ArgArg-L-CHO)$_4$ and PEG$^{5k}$(ArgArg-L-VE)$_4$, respectively, is similar with that for the telodendrimers with four guanidine groups, the only difference is to couple Fmoc-Arg(Pbf)-OH to the amino groups of the arginines before coupling the PEG linker molecules (FIG. 9). The synthesis procedure for the telodendrimers with eight amino groups containing heptadecanoic acids, cholesterols and D-α-tocopherol succinates (noted as PEG$^{5k}$(LysLys-L-C17)$_4$, PEG$^{5k}$(LysLys-L-CHO)$_4$ and PEG$^{5k}$(LysLys-L-VE)$_4$, respectively) is similar with that for the telodendrimers with eight guanidine groups, the only difference is to couple twice Fmoc-Lys(Boc)-OH to the amino groups of the polylysine before coupling the PEG linker molecules.

The telodendrimer with guanidine groups and without hydrophobic groups (named as PEG$^{5k}$Arg$_4$AA$_4$) was synthesized from acetic anhydride and a chemical intermediate 4 in FIG. 8. The Fmoc groups of chemical intermediate 4 were first removed by the treatment with 20% (v/v) 4-methylpiperidine in DMF, and the polymer was then coupled with acetic anhydride using triethylamine as a deacid reagent. The Pbf protecting groups were consecutively removed via the treatment with 50% TFA in DCM to yield PEG$^{5k}$Arg$_4$AA$_4$.

The telodendrimers containing cholesterol and/or cholic acid groups (named as PEG$^{5k}$CHO$_8$, PEG$^{5k}$CA$_4$CHO$_4$, and PEG$^{5k}$CA$_4$-L-CHO$_4$, respectively) were also synthesized using a solution-phase condensation reaction starting from MeO-PEG-NH$_2$.HCl (5 kDa) via stepwise peptide chemistry. The synthesis and characterization of these telodendrimers have been reported separately[14] and, therefore, are not repeated here.

Determination of Critical Micelle Concentration (CMC). Telodendrimers were dissolved in phosphate buffered saline (PBS, 1×). The initial micelle solution was diluted with PBS to obtain the required solutions ranging from 0.39 to 200 µg/mL. A known amount of Nile red in methanol was added to a series of vials. After methanol was evaporated under vacuum, a measured amount of polymer solutions were added to each vial to obtain a final Nile red concentration of 1 µM. The mixture solutions were left to shake overnight in the dark and at room temperature. The fluorescence emission intensity was measured using a microplate reader (Synergy 2, BioTek Instruments, Inc.) at the wavelength of 620 nm with excitation at 543 nm. CMCs were determined at the intersection of the tangents to the two linear fitting of the curve of the fluorescence intensity as a function of the log concentration of the telodendrimers.

Encapsulation of Proteins in Telodendrimer Nanoparticles. The proteins or protein mixtures were dissolved in PBS (1×), and the arginine-containing telodendrimers in PBS (1×) were quickly added into protein solution. The proteins were encapsulated by the telodendrimers through electrostatic interaction, hydrogen bonding, and hydrophobic-hydrophobic interaction.

Fluorescently Labeled Proteins and Telodendrimers. FITC-labeled BSA (named as FITC-BSA) was synthesized as follow: FITC-BSA was prepared by mixing 3 mg of FITC dissolved in 0.3 mL of DMSO with 10 mL of BSA aqueous solution (10 mg/mL) in the presence of 0.1 M of NaHCO$_3$ under stirring. The molar ratio of FITC to BSA is approximately 5:1. After 24 h, the reaction mixture was dialyzed against deionized water in the dark for one week to remove the unreacted FITC molecules, and dried by lyophilization. FITC-labeled insulin (noted as FITC-insulin) was synthesized as follow: FITC was dissolved in acetone (1 mg in 200 µL) and added dropwise to a 2.0 mL solution containing the appropriate amount of insulin dissolved in PBS (1×) contained 200 µM EDTA. After 24 h, the reaction mixture was dialyzed against deionized water in the dark for one week to remove the unreacted FITC molecules, and dried by lyophilization. FITC-labeled lysozyme (noted as FITC-lysozyme) was prepared by mixing 0.5 mg of FITC dissolved in 0.1 mL of DMSO with 15 mL of 3.3 mg mL$^{-1}$ of lysozyme in PBS (1×). The molar ratio of FITC to lysozyme is approximately 0.4:1. After 24 h, the reaction mixture was dialyzed against deionized water in the dark for one week to remove the unreacted FITC molecules, and dried by lyophilization. RB-labeled BSA (named as RB-BSA) was synthesized as follows: RB-OSu was first synthesized by mixing 10 mg of RB, 3 mg of HOSu and 4 µL of DIC dissolved in 0.5 mL of DMSO. RB-BSA was then prepared by mixing above RB-OSu solution with 20 mL of BSA aqueous solution (13 mg/mL) in the presence of 0.1 M of NaHCO$_3$ under stirring. After 24 h, the reaction mixture was dialyzed against deionized water in the dark for one week to remove the unreacted RB molecules, and dried by lyophilization. FITC-labeled PEG$^{5k}$(ArgArg-L-C17)$_4$ (named as FITC- PEG$^{5k}$(ArgArg-L-C17)$_4$) was prepared by mixing 0.4 mg of FITC dissolved in 0.2 mL of DMSO with 1 mL of PEG$^{5k}$(ArgArg-L-C17)$_4$ aqueous solution (10 mg/mL) in the presence of 0.1 M of NaHCO$_3$ under stirring. After 24 h, the reaction mixture was dialyzed against deionized water in the dark for one week to remove the unreacted FITC molecules, and dried by lyophilization. Cy5-labeled BSA (named as Cy5-BSA) was prepared by mixing 5 mg of Cy5NS succinimidyl ester dissolved in 0.3 mL of DMSO with 10 mL of BSA aqueous solution (10 mg/mL) in the presence of 0.1 M of NaHCO$_3$ under stirring. The molar ratio of dye to BSA is approximately 5:1. After 24 h, the reaction mixture was dialyzed against deionized water in the dark at 4° C. for one week to remove the unreacted dye molecules.

Agarose Gel Retention Assay. Samples in loading buffer (30% glycerol aqueous solution) were loaded into agarose gel (1.5% wt) in Tris-acetate-EDTA (TAE) buffer (1×). The gel tray was run for 2 h at a constant current of 20 mA. The gel was then stained with 1% Coomassie blue (30 min) followed by overnight destaining. The gel was imaged by a Bio-Rad Universal Hood II Imager (Bio-Rad Laboratories, Inc.) under SYBR Green and Coomassie blue modes. The loading capacity and loading efficiency of the nanoparticles were calculated from the Adj. Vol. (Int.) of the fluorescence bands for unloaded FITC-labeled proteins using the Image Lab 3.0 software.

Isothermal Titration calorimetry (ITC). ITC was performed on VP-ITC (MicroCal, LLC) with 1.4 mL cell at 295 rpm stirring at 37° C. Titrations were performed by injecting BSA solution (137 µM) into the calorimetric sample cell containing 30 µM of telodendrimers using 1 step of 1.5 µl injection and another 30 steps of 5 µl injections and 300 sec pauses between injections to allow the solution to reach equilibrium. Titration of protein into blank buffer (PBS, 1×) was performed for reference. Protein sample was dialyzed against buffer solution (PBS, 1×) for two days before the ITC measurement, and the concentration was calculated from the UV-vis spectrum based on the molar extinction coefficient of 43,824 M$^{-1}$cm$^{-1}$ for BSA at 279 nm. Heats of injections were calculated using Microcal analysis package for Origin 7.0.

Förster Resonance Energy Transfer (FRET) Studies. RB-BSA and FITC-PEG$^{5k}$(ArgArg-L-C17)$_4$ were used to prepare FRET nanoparticles. Equal volumes of 2 mg/mL of FITC-PEG$^{5k}$(ArgArg-L-C17)$_4$ solution and 2 mg/mL of RB-BSA solution were mixed, following by stirring overnight. Concentrated BSA solutions were then added into the above mixtures to reach final BSA concentrations from 0 to 40 mg/mL. The fluorescence spectra with a range from 480 to 640 nm at different time points excited by 439 nm were recorded using a microplate reader (BioTek Synergy 2). The FRET ratio was calculated by the formula of [100%×$I_{584}$/($I_{584}$+$I_{528}$)], where $I_{584}$ and $I_{528}$ were fluorescence intensities of RB-BSA at 584 nm and FITC-PEG$^{5k}$(ArgArg-L-C17)$_4$ at 528 nm, respectively. FITC-BSA and RB-BSA were also mixed for FRET study.

Bio-Layer Interferometry (BLI). The binding affinities of telodendrimers to proteins were measured at 37° C. by BLI on an Octet-Red 96 (ForteBio). Streptavidin biosensors (ForteBio) were prewetted in 40 mg/mL of BSA solution for 900 s, and incubated in the same solution for 900 s, washed in PBS for 480 s, and transferred to wells containing telodendrimers at concentrations ranging from 75 to 600 nM in PBS for 900 or 1800 s (association). Dissociation at each studied concentration was carried out in either PBS (1×) or BSA solution (5 or 40 mg/mL) for 1800 s. The $k_{on}$ and $k_{off}$ values were obtained by fitting the association and dissociation data to a 1:1 model algorithm using Octet software. The $K_D$ derived from kinetic fitting was calculated as $k_{off}/k_{on}$.

Hemolytic Assays. One milliliter of fresh blood from healthy human volunteers was collected into 5 mL of PBS solution in the presence of 20 mM EDTA. Red blood cells (RBCs) were then separated by centrifugation at 1000 rpm for 10 min. The RBCs were washed three times with 10 mL of PBS and resuspended in 20 mL of PBS. Diluted RBC suspension (200 µL) was mixed with nanoparticle PBS solutions at serial concentrations (10, 100, and 500 µg/mL) by gentle vortex and incubated at 37° C. After 0.5 h, 4 h, and over night, the mixtures were centrifuged at 1,000 rpm for 5 min. The supernatant free of hemoglobin was determined by measuring the absorbance at 540 nm using a UV-vis spectrometer. Incubations of RBCs with Triton-100 (2%) and PBS were used as the positive and negative controls, respectively. The percent hemolysis of RBCs was calculated using the following formula:

$$RBC\ \text{hemolysis} = \frac{(OD_{sample} - OD_{negative\ control})}{(OD_{positive\ control} - OD_{negative\ control})} \times 100\% \qquad (1)$$

Cell Culture and MTS Assays. The human glioblastoma multiforme cell line U87 and the colon cancer cell line HT-29 were purchased from American Type Culture Collection (ATCC, Manassas, Va., U.S.A.). All cells were cultured in 100 U/mL penicillin G, and 100 µg/mL streptomycin at 37° C. using a humidified 5% CO$_2$ incubator. Various formulations of proteins with different dilutions were added to the plate and then incubated in a humidified 37° C., 5% CO$_2$ incubator. After 4 h incubation, McCoy's 5A medium supplemented with 10% fetal bovine serum (FBS) was added into the above system. After 72 h incubation, a mixture solution composed of CellTiter 96 AQueous MTS, and an electron coupling reagent, PMS, was added to each well according to the manufacturer's instructions. The cell viability was determined by measuring absorbance at 490 nm using a microplate reader (BioTek Synergy 2). Untreated cells served as the control. Results were shown as the average cell viability [100%×($OD_{treat}$−$OD_{blank}$)/($OD_{control}$−$OD_{blank}$)] of triplicate wells. The cells were also treated with blank nanoparticles in PBS at different dilutions and incubated for a total of 72 h to evaluate nanoparticle-related toxicity.

Cellular Uptake. The cellular uptake and intracellular trafficking of the protein-incorporated nanoparticles were determined by fluorescence microscopy. FITC-BSA was used as a model protein. HT-29 and U87 cells were seeded in chamber slide with a density of 5×10$^4$ cells per well in 350 µL of McCoy's 5A and cultured for 24 h. The original medium was replaced with free FITC-BSA and FITC-BSA-loaded nanoparticles at a final FITC concentration of approximately 1.5 µg/mL at 37° C. After a 3 h incubation, the cells were washed three times with cold PBS (1×) and fixed with 4% formaldehyde for 10 min at room temperature, and the cell nuclei was stained with DAPI (blue). The slides were mounted with cover slips and cells were imaged with a NiKON FV1000 laser scanning confocal fluorescence microscope.

Characterization. Proton NMR spectrum was recorded on a Bruker AVANCE 600 MHz spectrometer. MALDI-TOF MS spectrum was recorded on a Bruker REFLEX-III instrument. Dynamic light scattering (DLS) studies were performed using a Zetatrac (Microtrac Inc.) instrument, and the area-based mean particle sizes were presented. Zeta potential measurements were carried out on a Malvern Nano-ZS zetasizer at room temperature. UV-vis spectra were recorded on a Thermo Scientific Nanodrop 2000c spectrophotometer. TEM images were taken on a JEOL JEM-2100 HR instrument operating at a voltage of 200 kV. The samples were prepared by dropping the solutions onto carbon coated grids, and stained by uranyl acetate.

TABLE 1

Properties of the telodendrimers before and after loading of proteins.

| telodendrimer | $M_w$ (Theo.)[a] | $M_w$ (MS)[b] | zeta potential (mV)[c] | $D_h$ (nm)[c] | CMC (μM)[d] | zeta potential (mV) with protein[e] | $D_h$ (nm) with protein[e] | $D_h$ (nm) with protein after storage[f] |
|---|---|---|---|---|---|---|---|---|
| PEG$^{5k}$(Arg-L-C17)$_4$ | 7,940 | 7,941 | −4.6 ± 0.7 | 11 ± 3 | 2.68 | −5.1 ± 0.7 | 10 ± 4 | 11 ± 3 |
| PEG$^{5k}$(Arg-L-CHO)$_4$ | 8,581 | 8,314 | −4.1 ± 0.5 | 27 ± 8 | 1.32 | −4.3 ± 0.3 | 22 ± 7 | 15 ± 5 |
| PEG$^{5k}$(Arg-L-VE)$_4$ | 8,981 | 8,728 | −3.2 ± 1.2 | 25 ± 9 | 1.35 | −4.4 ± 0.3 | 19 ± 9 | 22 ± 8 |
| PEG$^{5k}$(ArgArg-L-C17)$_4$ | 8,565 | 8,599 | −2.4 ± 0.6 | 17 ± 4 | 1.45 | −3.4 ± 0.3 | 13 ± 4 | 14 ± 4 |
| PEG$^{5k}$(ArgArg-L-CHO)$_4$ | 9,206 | 9,231 | −4.0 ± 0.1 | 18 ± 4 | 1.38 | −4.4 ± 0.1 | 12 ± 4 | 15 ± 5 |
| PEG$^{5k}$(ArgArg-L-VE)$_4$ | 9,606 | 9,624 | −1.2 ± 0.8 | 32 ± 13 | 1.14 | −3.0 ± 0.6 | 18 ± 8 | 27 ± 9 |

[a]Theoretical molecular weight.
[b]Acquired by MALDI-TOF MS analysis.
[c]Obtained in PBS at a concentration of 1 mg/mL.
[d]Measured by fluorescent method using nile red as a probe.
[e]Obtained in PBS at a telodendrimer concentration of 1 mg/mL with a BSA/telodendrimer ratio of ⅓ by weight.
[f]Obtained in PBS at a telodendrimer concentration of 1 mg/mL with a BSA/telodendrimer ratio of ⅓ by weight after a storage at 4° C. for 2 months.

TABLE 2

Summary of isothermal titration calorimetry results.

| telodendrimer | protein (equiv)[a] | $K_a$ (M$^{-1}$) | ΔH (kcal · mol$^{-1}$) | ΔS (cal · mol$^{-1}$ · K$^{-1}$) |
|---|---|---|---|---|
| PEG$^{5k}$(ArgArg-L-C17)$_4$ | 0.11 | 1.1 × 10$^6$ | 22 | 100 |
| PEG$^{5k}$(ArgArg-L-CHO)$_4$ | 0.15 | 1.8 × 10$^5$ | −37 | −96 |
| PEG$^{5k}$(ArgArg-L-VE)$_4$ | 0.09 | 3.5 × 10$^5$ | −34 | −84 |

[a]BSA equivalents conjugated with telodendrimers.

TABLE 3

Summary of bio-layer interferometry results.

| telodendrimer | $K_D$ (nM) | $k_{on}$ (M$^{-1}$ · s$^{-1}$) | $k_{off}$ (s$^{-1}$)[b] |
|---|---|---|---|
| PEG$^{5k}$(ArgArg-L-C17)$_4$ | 42 | 1.9 × 10$^4$ (±0.8%) | 8.1 × 10$^{-4}$ (±0.3%) |
| PEG$^{5k}$(ArgArg-L-CHO)$_4$ | 49 | 1.7 × 10$^4$ (±0.7%) | 8.5 × 10$^{-4}$ (±0.3%) |
| PEG$^{5k}$(ArgArg-L-VE)$_4$ | 59 | 7.8 × 10$^3$ (±0.6%) | 4.6 × 10$^{-4}$ (±0.3%) |
| PEG$^{5k}$(Arg-L-CHO)$_4$ | 89 | 7.9 × 10$^3$ (±0.6%) | 7.0 × 10$^{-4}$ (±0.4%) |
| PEG$^{5k}$Arg$_4$AA$_4$[a] | N/A | N/A | N/A |
| PEG$^{5k}$(Arg(Pbf)-L-CHO)$_4$ | 88 | 3.3 × 10$^3$ (±0.6%) | 2.9 × 10$^{-4}$ (±0.4%) |

[a]No obvious association was observed in the telodendrimer concentration range of 75-600 nM.
[b]BSA solution (40 mg/mL) was used as the dissociation buffer.

The invention claimed is:

1. A compound having the following structure:

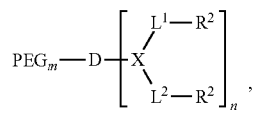

wherein

PEG is optionally present and is a polyethylene glycol moiety, wherein PEG has a molecular weight of 44 Da to 100 kDa;

X is a branched monomer unit;

each $L^1$ is independently optional and is a linker group;

each $L^2$ is independently optional and is a linker group;

D is a dendritic polymer having one or more branched monomer units (X);

$R^2$ is an end group and is independently at each occurrence in the compound selected from the group consisting of positively charged groups, negatively charged groups, hydrophilic groups, and hydrophobic groups, wherein for every group of two $R^2$ groups on the same branched monomer unit, one $R^2$ group of the group the two $R^2$ groups has a positively charged group or negatively charged group and the other $R^2$ group is uncharged;

subscript n is an integer from 1 to 32; and subscript m is an integer from 0 to 32, wherein the positively charged group, when present, is chosen from moieties or derivatives or analogs of arginine, guanidine, amidine, secondary amine, tertiary amine, quaternary amine, or tetrazole, and wherein the compound is a telodendrimer.

2. The compound of claim 1, wherein at each occurrence in the compound the branched monomer unit (X) is independently selected from the group consisting of a diamino carboxylic acid moiety, a dihydroxy carboxylic acid moiety, and a hydroxyl amino carboxylic acid moiety.

3. The compound of claim 2, wherein at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid.

4. The compound of claim 1, wherein the negatively charged group is a moiety or derivative or analog of hydroxyl, carboxyl, phosphate, sulfonate, methanesulfonamide, sulfonamide, or oxalic acid.

5. The compound of claim 1, wherein the positively charged group, when present, is chosen from moieties or derivatives or analogs selected from the group consisting of arginine, guanidine, amidine, secondary amine, tertiary amine, quaternary amine, and tetrazole.

6. A nanocarrier comprising a plurality of compounds of claim 1.

7. The nanocarrier of claim 6, wherein the nanocarrier further comprises one or more charged proteins.

8. The nanocarrier of claim 7, wherein the nanocarrier further comprises a cationic polymer.

9. A compound comprising the following structure: $PEG^{5k}(ArgArg-L-R)_4$, wherein R is

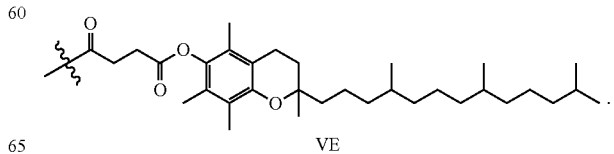

10. The compound of claim 9, comprising: a formula characterized as

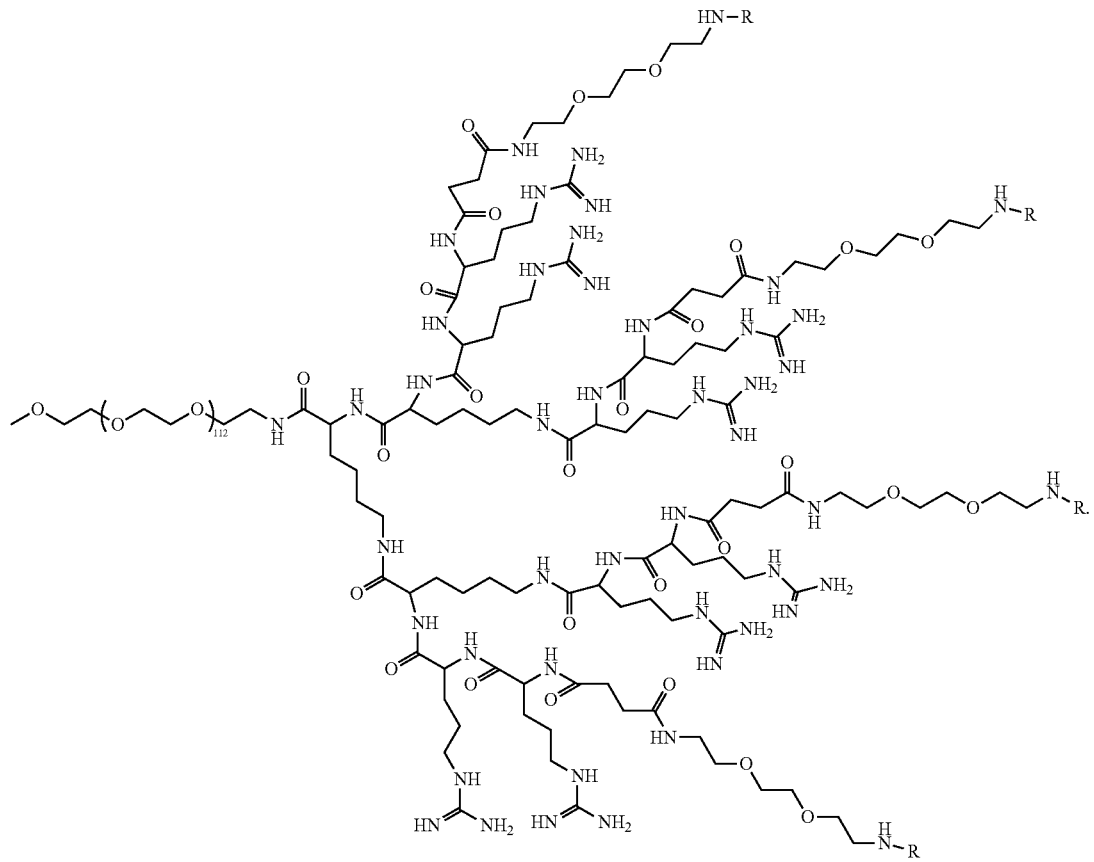

11. A compound having the following structure:

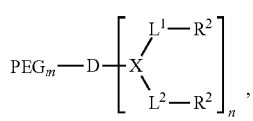

wherein
PEG is present and is a polyethylene glycol moiety, wherein PEG has a molecular weight of 44 Da to 100 kDa;
X is a branched monomer unit;
each $L^1$ is independently optional and is a linker group;
each $L^2$ is independently optional and is a linker group;
D is a dendritic polymer-having one or more branched monomer units (X);
$R^2$ is an end group and is independently at each occurrence in the compound selected from the group consisting of positively charged groups, negatively charged groups, hydrophilic groups, and hydrophobic groups, wherein for every group of two $R^2$ groups on the same branched monomer unit, one $R^2$ group of the group the two $R^2$ groups has a positively charged group or negatively charged group and the other $R^2$ group is uncharged;

subscript n is an integer from 1 to 32; and
subscript m is an integer from 0 to 32, wherein the positively charged group, when present, is chosen from moieties or derivatives or analogs of arginine, guanidine, amidine, secondary amine, tertiary amine, quaternary amine, or tetrazole.

12. The compound of claim 11, wherein at each occurrence in the compound the branched monomer unit (X) is independently selected from the group consisting of a diamino carboxylic acid moiety, a dihydroxy carboxylic acid moiety, and a hydroxyl amino carboxylic acid moiety.

13. The compound of claim 11, wherein at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid.

14. The compound of claim 11, wherein the negatively charged group is a moiety or derivative or analog of hydroxyl, carboxyl, phosphate, sulfonate, methanesulfonamide, sulfonamide, or oxalic acid.

* * * * *